(12) United States Patent
Narayan

(10) Patent No.: US 12,193,728 B2
(45) Date of Patent: Jan. 14, 2025

(54) SYSTEM AND METHOD FOR GUIDING DIRECTION TO AND TREATING TARGETS FOR ABNORMAL BIOLOGICAL RHYTHMS

(71) Applicant: The Board of Trustees of the Leland Stanford Junior University, Palo Alto, CA (US)

(72) Inventor: Sanjiv M. Narayan, Palo Alto, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 328 days.

(21) Appl. No.: 17/180,783

(22) Filed: Feb. 20, 2021

(65) Prior Publication Data

US 2021/0259765 A1   Aug. 26, 2021

Related U.S. Application Data

(60) Provisional application No. 62/979,367, filed on Feb. 20, 2020.

(51) Int. Cl.
*A61B 18/14* (2006.01)
*A61B 18/00* (2006.01)
(Continued)

(52) U.S. Cl.
CPC .......... *A61B 18/1492* (2013.01); *A61B 18/02* (2013.01); *G06N 20/00* (2019.01);
(Continued)

(58) Field of Classification Search
CPC ................ A61B 18/1492; A61B 18/02; A61B 2018/00065; A61B 2018/00095;
(Continued)

(56) References Cited

U.S. PATENT DOCUMENTS 6,231,570 B1   5/2001   Tu et al.
7,171,269 B1   1/2007   Addison et al.
(Continued)

FOREIGN PATENT DOCUMENTS

CN   106066933 A   11/2016
EP   2603138 B1   1/2017
(Continued)

OTHER PUBLICATIONS

Esteva, et al., Dermatologist-level classification of skin cancer with deep neural networks, Nature, Feb. 2, 2017, pp. 115-125, vol. 542.
(Continued)

*Primary Examiner* — Linda C Dvorak
*Assistant Examiner* — Abigail Bock
(74) *Attorney, Agent, or Firm* — Eleanor Musick; Torrey Pines Law Group PC

(57) ABSTRACT

An ablation catheter for treating electrical rhythm disorders includes an array of sensor electrodes to detect electrical signals to determine a location of a target region for treatment. If the catheter is not optimally positioned at the target region, a controller uses the detected signals to guide movement of the catheter towards the target region. Once proper positioning is ascertained, the controller activates ablation components within the catheter to deliver energy to modify tissue at the target region.

25 Claims, 22 Drawing Sheets

(51) Int. Cl.
*A61B 18/02* (2006.01)
*G06N 20/00* (2019.01)

(52) U.S. Cl.
CPC .............. *A61B 2018/00065* (2013.01); *A61B 2018/00095* (2013.01); *A61B 2018/00351* (2013.01); *A61B 2018/00577* (2013.01); *A61B 2018/00898* (2013.01); *A61B 2018/0212* (2013.01); *A61B 2018/025* (2013.01); *A61B 2218/002* (2013.01); *A61B 2562/046* (2013.01)

(58) Field of Classification Search
CPC ........... A61B 2018/00351; A61B 2018/00577; A61B 2018/00898; A61B 2018/0212; A61B 2018/025; A61B 2218/002; A61B 2562/046; G06N 20/00
See application file for complete search history.

(56) References Cited

U.S. PATENT DOCUMENTS

| | | |
|---|---|---|
| 7,850,685 B2 | 12/2010 | Kunis et al. |
| 7,996,074 B2 | 8/2011 | KenKnight et al. |
| 8,287,526 B2* | 10/2012 | Arless ................. A61B 18/02 606/20 |
| 8,538,774 B2 | 9/2013 | Michelson et al. |
| 8,700,140 B2 | 4/2014 | Narayan et al. |
| 8,868,169 B2 | 10/2014 | Narayan et al. |
| 8,876,817 B2 | 11/2014 | Avitall et al. |
| 8,954,339 B2 | 2/2015 | Schaffer |
| 9,050,006 B2 | 6/2015 | Narayan et al. |
| 9,282,910 B2 | 3/2016 | Narayan et al. |
| 9,687,166 B2 | 6/2017 | Subramaniam et al. |
| 9,730,603 B2* | 8/2017 | Laughner ............. A61B 5/6858 |
| 9,757,191 B2 | 9/2017 | Avitall et al. |
| 10,143,374 B2* | 12/2018 | Ruppersberg ........ A61B 5/0006 |
| 11,206,984 B1 | 12/2021 | Boveja et al. |
| 11,540,879 B2 | 1/2023 | Bort et al. |
| 11,564,591 B1 | 1/2023 | Narayan et al. |
| 11,583,346 B2 | 2/2023 | Bort et al. |
| 2002/0095151 A1 | 7/2002 | Dahla et al. |
| 2002/0107511 A1 | 8/2002 | Collins et al. |
| 2003/0204185 A1 | 10/2003 | Sherman et al. |
| 2004/0122709 A1 | 6/2004 | Avinash et al. |
| 2006/0167529 A1 | 7/2006 | Schecter |
| 2008/0281310 A1 | 11/2008 | Dunning et al. |
| 2009/0318749 A1 | 12/2009 | Stolen et al. |
| 2010/0042438 A1 | 2/2010 | Moore et al. |
| 2011/0106074 A1 | 5/2011 | Kunis et al. |
| 2012/0100134 A1 | 4/2012 | Lenz |
| 2012/0123232 A1 | 5/2012 | Najarian et al. |
| 2013/0116681 A1 | 5/2013 | Zhang |
| 2013/0267875 A1* | 10/2013 | Thapliyal ............... A61N 7/022 601/2 |
| 2013/0282084 A1 | 10/2013 | Mathur et al. |
| 2014/0128859 A1 | 5/2014 | Lee |
| 2014/0164784 A1 | 6/2014 | Sinderbrand et al. |
| 2014/0276712 A1 | 9/2014 | Mallin et al. |
| 2015/0042646 A1 | 2/2015 | Comaniciu et al. |
| 2015/0223759 A1* | 8/2015 | Ong ................... A61B 5/14542 600/301 |
| 2016/0157914 A1 | 6/2016 | Avitall et al. |
| 2017/0156791 A1 | 6/2017 | Govari |
| 2017/0164893 A1 | 6/2017 | Narayan et al. |
| 2017/0202619 A1 | 7/2017 | Lim et al. |
| 2017/0354339 A1 | 12/2017 | Zeidan et al. |
| 2018/0110439 A1 | 4/2018 | Grunwald et al. |
| 2018/0214202 A1* | 8/2018 | Howard ................ A61B 34/20 |
| 2019/0099211 A1 | 4/2019 | Altmann et al. |
| 2020/0367957 A1 | 11/2020 | Altmann et al. |
| 2021/0022794 A1* | 1/2021 | Viswanathan ..... A61B 18/1492 |
| 2021/0045805 A1 | 2/2021 | Govari et al. |
| 2021/0059737 A1* | 3/2021 | Babkin .................. A61B 18/02 |
| 2021/0077180 A1 | 3/2021 | Govari et al. |
| 2021/0106249 A1 | 4/2021 | Schmidt et al. |
| 2021/0220047 A1* | 7/2021 | Curran ............... A61B 18/1492 |
| 2022/0338923 A1 | 10/2022 | Bort et al. |
| 2022/0338936 A1 | 10/2022 | Bort et al. |
| 2022/0344025 A1 | 10/2022 | Bort et al. |
| 2023/0049942 A1 | 2/2023 | Narayan et al. |

FOREIGN PATENT DOCUMENTS

| | | |
|---|---|---|
| EP | 2339961 B1 | 3/2018 |
| EP | 3777743 A1 | 2/2021 |
| EP | 3791816 A2 | 3/2021 |
| JP | 6159250 B2 | 7/2017 |
| WO | 2006039694 A2 | 4/2006 |
| WO | 2010042826 A1 | 4/2010 |
| WO | 2013036677 A1 | 3/2013 |
| WO | 2013106557 A1 | 7/2013 |
| WO | 2016033609 A1 | 3/2016 |
| WO | 2019157359 A1 | 8/2019 |
| WO | 2019212833 A1 | 11/2019 |
| WO | 2023018741 A1 | 2/2023 |
| WO | 2023096666 A1 | 6/2023 |

OTHER PUBLICATIONS

LeCun, et al., Gradient-Based Learning Applied to Document Recognition, Proc. of the IEEE, 1998, pp. 1-46.
PCT/US2019/029004 International Search Report & Written Opinion of the International Searching Authority, Sep. 10, 2019, 7 pages.
Rajpurkar, et al., Cardiologist-Level Arrhythmia Detection with Convolutional Neural Networks, Jul. 6, 2017, pp. 1-9.
Alhusseini, M. et al., Machine Learning to Classify Intracardiac Electrical Paterns During Atrial Fibrillation, Arrhythm Electrophysiol., Aug. 2020, pp. 719-729.
Baykaner, T., et al., Machine Learning of Adipose Tissue in Atrial Fibrillation, Heart Rhythm, Dec. 2022, pp. 2042-2043, vol. 19.
Ganesan, P., et al., Quantifying a spectrum of clinical response in atrial tachyarrhythmias using spatiotemporal synchronization of electrograms, European Society of Cardiology, Eurospace 2023, pp. 1-9, vol. 25.
Nussinovitch, U., et al., Ambient Circulation Surrounding an Ablation Catheter Tip Affects Ablation Lesion Characteristics, J. Cardiovasc Electrophysiol., Apr. 2023, pp. 1-18, vol. 34(4).
Rodrigo, M., etal., Atrial Fibrillation signatures on intracardiac electrograms identified by deep learning, Computers in Biology and Medicine, 2022, pp. 1-9.
Roney, C. et al., Predicting Atrial Fibrillation Recurrence by Combining Population Data and Virtual Cohorts of Patient-Specific left Atrial Models, Circ Arrhythm Electrophysiol., Feb. 2022, pp. 94-102.
Tang, S., et al., Machine Learning-Enabled Multimodal Fusion of Intra-Atrial and Body Surface Signals in Prediction of Atrial Fibrillation Ablation Outcomes, Circ. Arrhythm Electrophysiol., Aug. 2022, pp. 500-509.
International Search Report and Written Opinion of the ISA, PCT/US2021/018940, May 4, 2021, 10 pages.
International Search Report and Written Opinion of the ISA, PCT/US2022/039873, Jan. 30, 2023, 11 pages.
International Search Report and Written Opinion of the ISA, PCT/SU2022/029630, Oct. 26, 2022, 23 pages.
Extended European Search Report and Written Opinion, EP 19 796 913.2, Jan. 4, 2022, 11 pages.
Extended European Search Report and Written Opinion, EP 21756920. 1, Jan. 31, 2024, 10 pages.

* cited by examiner

SYSTEM AND METHOD FOR GUIDING DIRECTION TO AND TREATING TARGETS FOR ABNORMAL BIOLOGICAL RHYTHMS

RELATED APPLICATIONS

This application claims the benefit of the priority of U.S. Provisional Application No. 62/979,367, filed Feb. 20, 2020, which is incorporated herein by reference in its entirety.

GOVERNMENT RIGHTS

This invention was made with government support under Grants HL083359 and HL103800 awarded by the National Institutes of Health (NIH). The government has certain rights in the invention.

FIELD OF THE INVENTION

The present invention relates generally to personalized identification and therapy for electrical rhythm disorders, and more particularly to a system and method for facilitating personalized treatment.

BACKGROUND OF THE INVENTION

Medical therapy can be improved by personalization. Accepted therapies that work in general may work poorly or not at all in a significant number of cases. Even in patients in whom a therapy works, there is often a graded response between individuals. Typically, there are few a priori clues that a particular therapy may or may not work in a given patient. "Predictors" of response or failure are often based on observation after the fact, and current forward-looking predictors provide modest incremental benefits.

Current medical strategies explicitly prioritize the majority of individuals with a stated condition, and implicitly neglect the statistical minority. An overlooked but important issue is that this minority of individuals with the same stated diagnosis may respond to a therapy that differs from that used on the majority. While this minority may comprise a substantial number of individuals, they may be difficult to identify (phenotype) because otherwise they may have already been separated from others into a different subcategory.

There is a need to personalize therapy—to identify a priori those patients in whom a therapy is likely to work, those in whom that therapy is less likely to work and, thus, tailor therapy for the individual. To meet these objectives, personalized medicine is increasingly studied.

Personalized medicine is frequently espoused for conditions that result from a genetic cause ("mechanism"), to phenotype individuals then tailor therapies accordingly. Unfortunately, many highly prevalent diseases do not have demonstrable genetic causes. In the heart, while genetic cases can be identified for example in coronary disease due to inherited familial hypercholesterolemia, or the heart rhythm disorder of inherited atrial fibrillation (AF), these cases are the minority. Most heart conditions cases do not have a clear genetic cause and are considered to result from multiple factors (multifactorial). Indeed, recent studies fail to show genetic abnormalities even in conditions traditionally considered genetic, including inherited sudden cardiac arrest in the young, i.e., Sudden Arrhythmic Death Syndrome ("SADS").

Other conditions are partially heritable or have genetic causes with "incomplete penetrance." The causes for variability in disease expression or response to therapy are unknown and occur, for example, with many therapies for atrial fibrillation. Such variability is often ascribed to "environment," and may be represented as the variations in the cellular "proteome" or "metabolome," but may be difficult to identify, is often unproven, and is rarely used to guide therapy.

In normal heart rhythms, the sinus node keeps the heart in sinus rhythm. Heart rhythm disorders are common and significant causes of morbidity and death throughout the world. The most prevalent forms of heart rhythm disorder do not have clear genetic causes.

Malfunction of the electrical system, or abnormal propagation of electrical waves is a proximate cause of rhythm disorders in the heart, brain and other organs that generate electrical impulses ('excitable tissue'). Heart rhythm disorders may be classified as simple or complex. Simple rhythms have a well-defined circuit that is stable over time, as detected by most methods of analysis. Examples include sinus rhythm (SR), rapid activation of the normal sinus node causing inappropriate sinus tachycardia (IST) or sinus node reentry, atrial tachycardia (AT) or flutter (AFL), atrio-ventricular nodal reentry tachycardia (AVNRT) and atrio-ventricular reciprocating tachycardia (AVRT). Complex rhythm disorders have less clear circuits that may change over time such as atrial fibrillation (AF), ventricular fibrillation (VF) or polymorphic ventricular tachycardia (PMVT). Other rhythm disorders may have simple activation patterns yet may be difficult to treat because they are transient, such as premature atrial complexes (PACs) or multiple premature ventricular complexes (PVCs), or difficult to ablate including atypical forms of atrial flutter or ventricular tachycardia (VT).

Treatment of heart rhythm disorders can be difficult, particularly for AF, VF and VT. Pharmacologic therapy for complex rhythm disorder is not optimal, only 40-60% success in the medium to long term. Ablation for heart rhythm disorders is increasingly used and involves maneuvering a sensor/probe to the heart via the blood vessels or directly at surgery and delivering energy to a source region to mitigate or eliminate the rhythm disorder. Ablation is often difficult for complex rhythm disorders because conventional systems to identify and locate a cause (source) are deficient, lacking in accuracy, precision, and/or time efficiency, which hinders attempts to deliver energy to eliminate the disorder. For instance, success of a single ablation procedure for "paroxysmal" AF, considered the simplest form, is only 65% at one and a half years, dropping further over time. For patients with more complex, persistent AF, the single procedure success by the "gold standard" technique is about 40-50% at year one off medications.

Several unmet needs exist which, if addressed may improve the success of therapy. First, why does the same ablation approach work in some patients yet not others, even after multiple attempts? Second, what mechanisms for rhythm disorders are similar or differ between individuals, and can they be identified ahead of time? Current disease classifications are not ideal for this purpose, since pulmonary vein isolation fails in 35-50% of cases of "simple" paroxysmal AF yet works in 40-50% of cases of "advanced" persistent AF, both at 1-2 years.

One proposed mechanism (cause) for AF is localized source regions or drivers (termed rotors, sites of rotational activity, repetitive activity or foci) that may drive surrounding disorganized activity. It is unclear how best to identify said sources. It is unclear why some patients do well after ablation of AF sources, while others do not. It is unclear why some individuals have a small number of source regions even in complex AF, while others have several. It is undefined if source regions relate to structural abnormalities such as low voltage or magnetic resonance imaging abnormalities in some persons but not others.

Electrical rhythm disorders are classified by electrical patterns. This often involves the introduction of a catheter having a plurality of sensors/probes into the heart through blood vessels of the patient. These sensors detect electric activity of the heart (electrograms) at multiple locations, which has been used to identify causes of conditions such as AVRT or AVNRT and define separate therapy even though ECG appearances are similar. For simple arrhythmias such as atrial tachycardia, the source can be identified by tracing activation back to the earliest location, which is then cauterized (ablated) to treat the disorder. This may be challenging even in simple heart rhythm disorders.

Identifying the source or other target region to treat complex rhythm disorders is more challenging. First, signals at each sensor may transition beat-to-beat in shape and number of deflections. When a signal in AF has 5, 7, 11 or more deflections, it is difficult to identify which are local (i.e., under the sensor), which are from neighboring regions (i.e., far-field activity) or noise. Second, the relative paths of activation between neighboring sensor sites may change over time, such as in AF or VF. Overall, this makes it difficult to correctly map activity in a complex arrhythmia to identify its source.

Causes for heart rhythm disorders can been identified by several methods, yet none is perfect. It is difficult to identify a priori which patients do and do not have localized sources. Some sources identified may be false-positives that do not need treatment (even if the sources were validated by optical imaging). Methods to identify sources are cumbersome and time consuming to use, including using unwieldy, low-resolution approaches. Because sources may lie at any location, conventional methods often map the entire chamber with multipolar catheters or non-invasively from the body surface. These types of global mapping systems are difficult to use and have low and variable spatial resolution.

Further, conventional treatment methods for complex arrhythmias often require different tools to map the arrhythmia and distinct tools to deliver therapy, introducing a practical disconnect when switching tools. When swapping out systems used to detect critical regions for systems to treat those regions, registration errors may reduce the accuracy of treating precisely the same site and add time. It is also unclear with conventional approaches which source regions, when detected, are the most important. So, all sources are commonly treated, although some of these sites may not be critical in any given patient, yet this treating of all sources adds time, difficulty and potential risk to the procedure.

SUMMARY OF THE INVENTION

The inventive system and method identify and locate source regions or other target regions to treat biological rhythm disorders using a personalized digital medicine approach. The inventive system uses a probe or catheter to detect electrical signals from biological tissue, and provides navigational guidance towards source or target regions for a rhythm based on the detected electrical signals. The inventive system can then directly treat these regions without moving or replacing the probe or catheter. All steps can be tailored to an individual automatically based on quantified artificial intelligence-based algorithms of how patients with similar data patterns respond to therapy.

The system and method described herein provide a scheme for quantitative personalized therapy via one or a combination of lifestyle changes, medications, electrical or mechanical therapy, surgical or minimally invasive ablation, genetic or stem cell therapy. The invention disclosed herein is related in part to the subject matter of International Application No. PCT/US2019/029004, filed 22 Jul. 2019, the disclosure of which is incorporated herein by reference in its entirety.

One exemplary embodiment uses tools to identify individuals in whom ablation therapy for complex rhythm disorders is likely to succeed. These tools may be non-invasive or invasive. In patients amenable to ablation therapy, another embodiment includes a device to record electrical patterns within the heart and provide directional guidance to move the device in three dimensions within the biological organ towards optimal locations for therapy. Another embodiment provides the ability to deliver therapy directly to tissue at this location.

In some embodiments, the inventive system provides personalized diagnosis of complex rhythm disorders, navigational guidance to target sites of interest for the rhythm disorder, and a "single shot" detecting and therapeutic tool for said rhythm disorders.

An advantage of the invention is its ability to personalize therapy by comparing streams of data from the current individual to streams from other individuals with similar or dissimilar profiles, using a digital taxonomy that can be updated using strategies such as crowd-sourcing.

While the examples described herein are directed to disorders of heart rhythm, mechanical contraction, or heart failure, other exemplary applications of the inventive approach include seizure disorders of the brain, diseases of gastro-intestinal rhythm such as irritable bowel syndrome, and bladder disease including detrusor instability. In general, the inventive scheme is applicable to chaotic disorders in organs, such as atrial fibrillation in the heart or generalized seizures in the brain, as well as simple rhythm disorders. Accordingly, the examples provided herein are not intended to be limiting. The personalization aspect of the invention is suited for disorders which are heterogeneous syndromes rather than a single disease entity.

The invention identifies patients in whom targets for therapy are localized sources for the rhythm disorder, and patients in whom sources are not present. An example of this embodiment is to identify patients with atrial fibrillation who are likely to benefit from pulmonary vein isolation ablation alone. Other patients may require ablation of localized sources for success. Others may require ablation of other targets such as those targeted by Maze surgery. Similarly, the inventive approach can identify patients with ventricular tachycardia in whom ablation will or will not be successful.

Source regions are a subset of targets for a rhythm disorder and are identified as patches or regions of organized activity (a) within chaotic disorders such as atrial fibrillation in the heart, or (b) from which activation emanates to driver organized disorders such as atrial tachycardia or ventricular tachycardia. The inventive scheme uses analytical tools including machine learning to detect organized patches. Sources that lie near regions targeted by standard therapy, such as pulmonary veins in atrial fibrillation, a scar isthmus for ventricular tachycardia or a focal brain lesion for seizure disorders, may not require specific further therapy. This information is conveyed to the operator.

The inventive approach also indicates the most important target regions for the rhythm disorder. Without this information, approaches often include treating all detected targets in atrial fibrillation, involving detection and therapy of multiple sources, tissue regions of scar or complex signals. However, some of these regions may not be critical, and this approach can be time consuming, adds difficulty to the procedure, and may have adverse effects. The invention thus identifies patients with targets that lie within regions already treated by standard therapy, or that are less clear, neither of which require additional therapy.

In one embodiment, the invention quantifies the importance of regions of interest by quantifying the size or area of organized regions or patches within disordered activity such as atrial fibrillation in the heart or generalized tonic/clonic seizures in the brain. A hierarchy of targets, from the most dominant to the least, is conveyed to the operator and can be used for treatment planning.

The inventive approach uniquely detects treatment targets for biological rhythm disorders such as localized sources without the need for wide-area global mapping. Global mapping can be cumbersome, may not cover the entire organ, and typically requires the use of large probes or catheters that are not ideally suited or unable to deliver therapy, thus necessitating use of separate probes for sensing and for therapy. In one embodiment, the inventive system uses a mapping spade that is physically large enough to cover a source region for simple or complex rhythm disorders, or other targets such as channels of viable tissue within fibrotic regions that are small enough to provide high-density recordings.

The mapping tool or spade contains a plurality of electrodes that may number on the order of 4-256 electrodes. The size of each electrode ranges from 0.1 to 4.0 mm, with selection of the size depending at least in part on the nature of the suspected disorder. For complex rhythms such as atrial fibrillation, a typical electrode ranges in size from 0.5-1.0 mm to provide good signal fidelity and detect complex signal types that may be targets for therapy. For ventricular tachycardia, a typical electrode ranges in size from 1-2 mm. For simple rhythms such as accessory pathway mediated tachycardia, a typical electrode size range will be 0.5-1 mm, to discern accessory pathway potentials. Selection of appropriate electrode sizes for other applications will be within the level of skill in the art.

Spacing between electrodes varies in the range of 0.5-5.0 mm. For atrial fibrillation, a typical electrode spacing will be 1-2 mm. For ventricular tachycardia, a typical electrode spacing will be 2-4 mm. When very fine detail must be resolved, a typical electrode spacing will be 0.5-0.75 mm.

The size of the spade is personalized to the number of electrodes and their spacing, as well as to the type of rhythm and the profile of the patient. Personalization is performed using tools such as machine learning calibrated to patients of similar type and data (personalized digital phenotypes, PDP). The spade therapy tool contacts the organ by conforming to its surface at the same plurality of locations where targets or sources were recorded.

Contact can be enhanced using a variety of compliant materials in construction, depending on the intended location within the organ of interest. Nitinol (nickel titanium alloy) is one such material, e.g., 34-36 gauge, that can provide sufficient structural stability and flexibility. This can be used to construct devices for heating ablation, such as radiofrequency or light-emitting diodes, for freezing, such as cryoablation, or non-thermal ablation such as pulsed-field ablation. One embodiment uses a conformable chamber for mapping and cryoablation, in which the therapy device adheres to tissue during energy delivery for rapid, accurate and safe ablation. This can be effective for sources of atrial fibrillation and atrial tachycardias in the heart, and for seizure foci in the brain.

In one embodiment, comprises both detector and treatment elements in the same physical device, eliminating the need to use separate tools for each. This reduces time and complexity, and may also improve accuracy since locations of desired target regions do not have to be stored or registered and then re-found using a separate tool.

In an embodiment, the invention provides navigational guidance for a sensor tool without first collecting data globally using cumbersome large catheters. The invention processes data at the current sensor site and calculates the direction in which to move the sensor to navigate to the source. This is analogous to automobile global positioning systems that use current position to navigate to a desired location, without examining the entire map of the earth. This approach enables higher resolution mapping near the target region than used currently in wide-area or global mapping systems in the heart.

The invention personalizes detection and therapy using personal digital phenotypes (PDP) of health and disease. PDPs implement "personalized medicine" or "precision medicine" digitally, with or without cellular or genomic data. In general, -omic data may be unavailable for many individuals, or may contribute less to diseases of aging or environment. Input data (e.g., data streams from sensors, stored data from the electronic health record, imaging data) are linked to observed labels such as changes in surrogate markers, or elimination of the disease with specific therapy. PDPs then partition inputs into those associated with health and those associated with deviations (possible disease) for that individual. Thus, the invention does not cater just to the statistical majority of individuals.

PDPs can combine data streams from various sensors, medical or consumer machines separately or in combination (e.g., networked). Data streams may come from specialized equipment such as imaging systems, or from novel wearable sensors, or from multiple people for crowd-sourced population data. Data from pre-existing systems may include data from multiple hospitals in a large digital registry of de-identified data, contributing diverse patients, practice patterns and outcome data from different therapies. Such approaches may involve blockchain technology to ensure data security, traceable logs of data transactions, and data access across multiple physical storage systems.

PDPs indicate the relevance of biological and clinical data for the rhythm disorder in that individual, which may be unclear to experts, using systems and methods trained on previously labeled datasets in which a specific therapy was or was not successful. This enables the identification of individuals with and without treatable forms of the disorder, such as predicting the locations of sources for a biological rhythm disorder, helping to guide navigation to said source, predicting the type and size of said source, and the likely response to therapy personalized to that individual.

PDPs are created from a digital taxonomy of patients with a given disease or state of health. The taxonomy is constructed from multiple data streams and stratified by favorable or unfavorable outcome. Input data can be simple, such as heart rate, weight and other readily accessible data, stored elements of the electronic health record, and/or complex or sophisticated data which may change dynamically over time (e.g. proteomics and biomarkers) or may not change over time (e.g. genetic data). Other phenotypes may be clinical labels not tracked by a biomarker, or those with loose statistical definitions such as race or ethnic susceptibility. The more detailed and broad, i.e., the "richer," the population data elements, the more comprehensive the digital taxonomy.

Personal digital phenotypes (PDPs) are quantified pathophysiologic networks, representing indices from signal processing, associative algorithms, data clusters including those from unsupervised machine learning, and supervised networks trained by labeled events in similar and dissimilar individuals. Data are partitioned into data labeled as 'healthful vs disease', or 'responsive to therapy vs non-responsive' analyzed by one or more of supervised machine learning, neural networks, unsupervised machine learning, cluster analysis, correlation analyses, logistic regression analyses, decision trees, time domain analyses, frequency domain analyses, trigonometric transformations, and logarithmic transformations.

The patient's tissue may be heart, nerves that supply regions of the heart, regions of the brain that control the nerves, blood vessels that supply regions of the heart, and tissues adjacent to the heart. In some embodiments, the disease may be a heart rhythm disorder comprising one or more of atrial fibrillation, ventricular fibrillation, atrial tachycardia, atrial flutter, polymorphic or monomorphic ventricular tachycardia, ventricular flutter, or other electrical disturbance within the heart.

PDP-based analysis may decipher patterns of heart rhythm disorders that are difficult to understand by experts. This is particularly true of complex disorders which may include rotational circuits, focal circuits, repetitive patterns, partial rotational or focal circuits, "random" activity, electrical propagation around areas of scar, or specific anatomical sites in an individual. These patterns are difficult to sort out. The digital taxonomy links specific patterns with success or failure of drug therapy, ablation, maze surgery or other therapies for patients of a given PDP. PDPs for the current patient, based on her/his electrical, structural, and clinical data, are 'fit' to the taxonomy to identify tailored targets for therapy. This personalized diagnosis, or identification of targets for therapy, is novel and based on integration of data across biological scales.

PDPs for heart rhythm may include data streams of invasive recordings of electrical activity (electrograms), blood flow and pressure (hemodynamics), wall tension (cardiac contractility and relaxation), and related indices. More detailed data includes three-dimensional anatomical and structural abnormalities. Clinical data can be extracted from history and physical examination, indices of pathophysiological comorbidities, blood and tissue biomarkers, and genetic and cellular makeup of an individual. Noninvasively, sensors may record the electrocardiogram, cutaneous measures of nerve activity, and skin reflectance. Other types of sensed signals that may be used will be apparent to one of skill in the art.

For complex heart rhythm disorders, inflammation is a likely contributor yet is often not included in patient phenotyping. Inflammation may cause some arrhythmias after surgery or other conditions such as myocarditis. The link of obesity with atrial fibrillation may operate through inflammation in pericardial fat, in turn due to reactive oxygen species. Inflammatory findings may have significance which is undefined in any given person at one point or over time, or between people. The "inflammosome" may measure the impact of inflammation from various pathological insults at the cellular or tissue level, yet is not commonly done, may not assess circadian fluctuations, have unclear relationships to inflammation for the entire body, and may differ between individuals. It is thus unclear how to establish "nomograms" of normal or abnormal states.

Biomarkers of inflammation are one data stream. A personalized state of inflammation may be detected by inflammatory cells in the inflamed organ system, or in body fluids such as the blood, urine or cerebrospinal fluid. Byproducts of inflammation can be detected by elevated concentrations of biomarkers and cytokines such as interleukin-6, nerve growth factor, matrix metalloproteinases. Conversely, several physiological markers are abnormal in inflammation (so called "acute phase reactants"). Inflammation causes, in addition to elevated white cell counts, abnormalities in red cell count, in hemoglobin concentration, and in a myriad of acute phase reactants such as C-reactive protein, erythrocyte sedimentation rate or white cell counts. In the heart, it is well known that serum troponin, a marker of cardiac cell destruction, is an acute phase reactant whose levels fall with inflammation ('inverse acute phase reactant').

Arrhythmias in the subgroup of patients with inflammatory causes, may be targeted using anti-inflammatory therapy including immunosuppression using agents such as tacrolimus, a hitherto unrecognized form of therapy for complex arrhythmias such as atrial fibrillation. Other immunosuppression therapy such as steroids or non-steroidal agents, or cell therapy may be effective. One rationale is that patients who receive immunosuppressive agents after heart transplant rarely develop AF. While benefit is attributed to surgical isolation of the pulmonary veins during transplantation, such isolation in other populations provides <50-70% freedom from AF. The use of immunosuppression for complex rhythm disorders including AF has rarely been used. Digital taxonomies and PDPs in the invention will identify individuals with inflammatory mediated arrhythmias in whom anti-inflammatory therapy including immunosuppression may be useful.

For other organ systems, sensed signals from measurable body systems may include the central and peripheral nervous system, or the electroencephalogram (EEG) measured on the scalp, invasive electrode recordings or peripheral sensors. Measurements may also include the respiratory system, skeletal muscles and skin, any indexes of electrical signals, hemodynamics, clinical factors, nerve signals, genetic profile, biomarkers of metabolic status, and patient movement. Other input data elements may come from imaging, nuclear, genetic, laboratory, or other sources, and may also be sensed as a stream (i.e., transmitted to the system), or input as values at specific points in time.

In general, sensors may be in physical contact with the patient's body and the sensor data stream is acquired by one of wired or wireless transmission. The sensor may be one or more of an electrode, an optical sensor, a piezoelectric sensor, an acoustic sensor, an electrical resistance sensor, a thermal sensor, an accelerometer, a pressure sensor, a flow sensor, and an electrochemical sensor.

Personalized therapy may include modifying at least a portion of the patient's tissue by one or more of ablation by energy delivery via contact devices, energy delivery by noncontact devices, electrical therapy, thermal therapy, mechanical therapy, delivery of drug therapy, delivery of immunosuppression, delivery of stem cell therapy, and delivery of gene therapy. The method may further include generating updated personal historical data with the PDP, the classified one or more qualitative disease classifications, the personalized intervention, and an intervention outcome.

In one aspect, the inventive system includes a processor and a memory storing instructions that, when executed by the processor, performs operations including detecting bodily signals associated with one or more bodily functions at one or more sensors associated with the human body, processing the bodily signals to create one or more sensed signatures, processing the signatures using the digital object to determine an effector response, delivering one or more effector responses to control a bodily task and monitoring said response.

In another aspect of the invention, an ablation catheter for treating electrical rhythm disorders includes an array of sensor electrodes to detect electrical signals to determine a location of a target region for treatment. If the catheter is not optimally positioned at the target region, a controller uses the detected signals to guide movement of the catheter towards the target region. Once proper positioning is ascertained, the controller activates ablation components within the catheter to deliver energy to modify tissue at the target region.

In summary, the present invention can identify individuals amenable to therapy for complex rhythm disorders, provides directional guidance in three dimensions to move a novel sensor device towards optimal locations for therapy, and provide the ability to deliver therapy directly to tissue at this location. An embodiment is thus a system providing personalized diagnosis of complex rhythm disorders and a 'single shot' sensor/therapy tool. Some embodiments, which are not intended to be limiting, include cardiac applications in heart rhythm disorders, in coronary artery disease and in heart failure.

In one aspect of the invention, a system for treating a heart rhythm disorder includes a catheter configured to be placed in contact with a tissue surface, the catheter comprising a flexible body having a contact surface; an array of sensor electrodes arranged within the flexible body, each sensor electrode having a conductive surface substantially flush with the contact surface, each sensor electrode configured to detect electrical signals from the tissue surface; and one or more treatment elements configured to deliver energy to the tissue surface. Each conductor of a plurality of conductors has a distal end connected to one of a sensor electrode and the one or more treatment element. A controller in communication with proximal ends of the plurality of conductors includes a processor configured to: receive the detected electrical signals; determine a location of a target region of a heart rhythm disorder; determine whether the catheter is optimally positioned at the target region, and, if not optimally positioned, to compute directionality to the target region and generate movement instructions to move the catheter toward the target region; and after determining that the catheter is optimally positioned, generate treatment signals to activate the one or more treatment elements to modify tissue in the target region. In some embodiments, the flexible layer is generally planar and has a shape selected from a group consisting of a rectangle, an ellipse, and an annulus. An elongated hollow shaft having a distal end, a proximal end, and a length, is provided with the catheter is disposed at the distal end, the controller is disposed at the proximal end, and so that the plurality of conductors is retained within and extends the length the shaft, wherein the distal end of the shaft is manipulable from the proximal end. A shaft motor may be configured to steer the distal end of the shaft in response to movement instructions generated by the controller.

A sheath slidably disposed on the shaft has an interior volume configured to retain the catheter in a folded condition until the catheter is deployed by sliding the sheath away from the distal end of the shaft.

In some embodiments, the catheter may further include irrigant pores formed in the flexible body, the irrigant pores in fluid communication with an irrigant source associated with the controller, wherein the irrigant source is configured to deliver irrigant through the irrigant pores to tissue at the target region in conjunction with activation of the array of treatment elements.

In some embodiments the one or more treatment elements comprise an array of ablation electrodes, and wherein a subset of the plurality of conductors connected to the one or more treatment elements are electrical conductors configured to deliver electromagnetic energy to each ablation electrode. The array of sensor electrodes and the array of ablation electrodes may be uniformly distributed around the contact surface, or the array of ablation electrodes may be evenly interspersed among the array of sensor electrodes.

The processor may be further configured to determine a size of the target region based on the detected electrical signals, identify one or more ablation electrodes of the array of ablation electrodes based on at least the size and the location of the target region; and activate the identified ablation electrodes.

The processor may determine the location of the target region by generating a directionality map of heart rhythms based on the detected electrical signals, the directionality map describing pathways of heart rhythms, generating a guidance direction in which to move the flexible body towards the target region, and integrating the directionality map to determine the location of the target region. The directionality map can be generated by applying a trained machine learning model to the electrical signals, wherein the machine learning model is trained on training examples comprising electrical signals of a human heart and known target regions of the heart rhythm disorder.

In some embodiments, each ablation electrode is configured to emit a distinct waveform. The controller can be configured to separately address one or more subsets of ablation electrodes of the array, and wherein the treatment signals comprise a first signal to a first subset of ablation electrodes to emit a first waveform and a second signal to a second subset of ablation electrodes to emit a second waveform. The array of sensor electrodes comprises at least four electrodes. In some embodiments, the sensor electrodes can be configured to deliver ablation energy so that the one or more treatment elements comprise the array of sensor electrodes.

In certain embodiments, the one or more treatment elements comprise one or more coolant chambers formed within the flexible body and configured for retaining a coolant, and wherein the plurality of conductors comprises a subset of conductors configured to direct a coolant fluid from a coolant source to the one or more coolant chambers to deliver freezing energy to tissue at the target region. The flexible body may have a thermally conductive material incorporated therein to enhance conduction of freezing energy to tissue in contact with the contact surface. Alternatively, the one or more treatment elements may be an array of cryoablation loci formed within the flexible body, and wherein the plurality of conductors comprises a subset of conductors configured to direct a coolant fluid from a coolant source to the cryoablation loci in response to treatment signals from the controller to deliver freezing energy to tissue at the target region. In still other embodiments, the one or more treatment elements may be an array of targeting fiducials distributed within the flexible body where the targeting fiducials are configured for guiding delivery of ablation energy from one or more external ablation energy sources.

In still another aspect of the invention, a method for treating a heart rhythm disorder includes detecting electrical signals of a heart using the array of sensor electrodes; generating a directionality map describing pathways of heart rhythms based on the detected electrical signals; integrating the directionality map to determine one of: (i) a location of a target region of the heart rhythm disorder in the directionality map, and (ii) a guidance direction to the target region of the heart rhythm disorder outside the directionality map; determining whether the flexible body is optimally positioned at the target region according to the directionality map; and responsive to determining optimal positioning, activating the one or more treatment elements of the system to deliver energy to modify tissue at the determined location of the target region. Generating the directionality map may involve applying a trained machine learning model to the detected electrical signals, wherein the machine learning model is trained on training examples comprising electrical signals of a human heart and known locations of one or more target regions of a heart rhythm disorder.

In some embodiments, the method may further include, responsive to determining the guidance direction to the target region outside the directionality map, steering the device to a subsequent position in the guidance direction to the target region. Further, the method may also involve detecting subsequent electrical signals of the heart with the plurality of sensing electrodes after steering the device to the subsequent position; generating a subsequent directionality map describing pathways of heart rhythms based on the subsequent electrical signals; integrating the subsequent directionality map to determine one of: (i) the location of a target region of the heart rhythm disorder in the subsequent directionality map, and (ii) a subsequent guidance direction to the target region of the heart rhythm disorder outside the subsequent directionality map; and responsive to determining the subsequent guidance direction to the source region outside the directionality map, steering the flexible body to a third position in the subsequent guidance direction to the target region. Additionally, the method may include, responsive to determining the direction of the target region outside the directionality map, providing a notification on an electronic display to move the device in the direction of the target region. Other approaches may include one or more of, responsive to determining the location of the target region, identifying the one or more ablation components within a threshold proximity to the location of the target region, and determining a size of the target region based on the directionality map, wherein identifying the one or more ablation components is further based on at least the size of the target region.

In still other embodiments, the method may include, responsive to determining that the heart rhythm disorder persists: generating a subsequent directionality map describing pathways of heart rhythms based on the subsequent electrical signals; integrating the subsequent directionality map to determine one of: a location of a second target region of the heart rhythm disorder in the subsequent directionality map, and a guidance direction to the second target region of the heart rhythm disorder outside the subsequent directionality map; and responsive to determining the location of the second target region, instructing one or more ablation components of a plurality of ablation components on the device to modify tissue at the second target region at the determined location of the second target region.

BRIEF DESCRIPTION OF THE DRAWINGS

Some embodiments are illustrated by way of example and not limitation in the figures of the accompanying drawings in which.

DETAILED DESCRIPTION OF EXEMPLARY EMBODIMENTS

Figure 1:
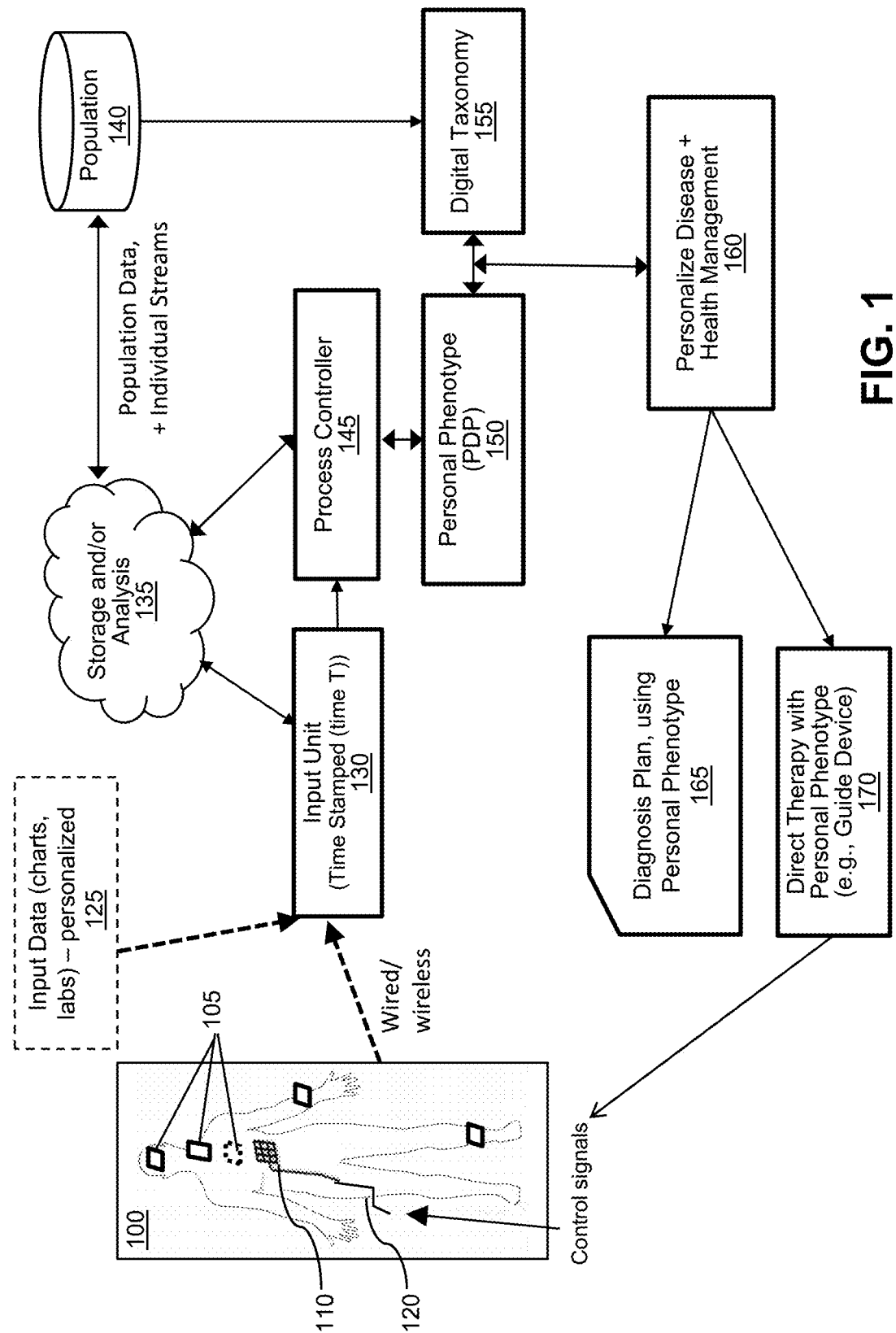
FIG. 1 is a block diagram depicting the use of personal digital phenotypes (PDP) for clinical purposes in an individual, for comparison against a digital taxonomy to enable personalized diagnosis and deliver personalized therapy, in accordance with one or more embodiments.

For the purposes of this disclosure, the following definitions apply:

"Ablation energy" refers to energy used to modify tissue. The tissue being modified may correspond to a source region or other target region for an electrical rhythm disorder. Modification of the tissue affects one or more electrical rhythms generated at the source region. The intended effect in providing ablation energy to the target region is to treat an electrical rhythm disorder. Ablation energy includes electromagnetic energy (e.g., in the form of radio frequency waves administered by ablation electrodes), freezing energy (e.g., removal of heat from a tissue with a coolant, generally a rapid removal or rapid cooling), some other form of energy capable of modifying tissue.

"Associative learning" means the process of linking input data with a measurable physiology or clinical outcome. Associative learning may be iterative, enabling associations to be modified ("learned") based upon patterns of change between input and measured output (physiological or clinical endpoints).

"Biological signal" is a signal is produced by the body and can reflect one or more bodily systems. For instance, the heart rate reflects cardiac function, autonomic tone and other factors. See also non-biological signal.

"Biometric signals" mean signals that provide metrics of human characteristics. Biometric identifiers can be physiological or behavioral. Physiological biometrics include, but are not limited to DNA, fingerprints or palm prints, mouth swabs, tissue or urine samples, retinal images, facial recognition, geometry of the hand or foot, recognition of the iris or odor/scent of an individual. It can also be applied to signals such as vital signs, the ECG, the EEG, EMG, and so on. Behavioral biometrics include patterns such as gait during walking or typing rhythm. Embodiments of the invention use dynamic patterns of combined physiological and behavioral biometrics over time, which adapt to changes in the individual and are thus robust to forgery from prior "versions" of a person's signature.

"Body" means the physical structure of a single-celled organism, a multi-celled organism, viruses, and prions. Organisms include animals (such as, but not limited to, humans and other mammals), plants, bacteria, etc.

"Consumer device" means a device that is available directly to a consumer without a medical prescription. Historically, such devices typically were not regulated by a medical regulatory agency or body, such as the U.S. Food and Drug Administration or similar regulatory bodies in other countries, however, more recently, some devices are FDA cleared. A Consumer device may include hardware, software, or a combination thereof. It is typically not a medical device, the latter being defined as an instrument, apparatus, implement, machine, contrivance, implant, in vitro reagent, or other similar or related article, including a component part, or accessory, which is intended for use in the diagnosis of disease or other conditions, or in the cure, mitigation, treatment, or prevention of disease, in man or other animals. The definition of a medical device excludes medical decision support software.

"Effector" is a means of performing a task, such as a physical appliance, prosthesis, mechanical or electronic device. A physical appliance may enhance a bodily function, such as a device to move a limb or move the diaphragm to enhance breathing during sleep or a splint to keep the airway open during sleep, or one or more signals to stimulate a bodily function, such as electrical stimulation of the phrenic nerve to enhance breathing during sleep, or an artificial prosthesis such as a cybernetic limb or implanted circuit for the peripheral or central nervous system.

"Data streams" or "stream(s) of data" mean biological data sensed by one or more sensors that can provide real-time or near-real-time information on the biological process being sensed. Sensors in the heart may provide streams comprising the electrocardiogram (ECG), pulse rate, pulse waveform and hence cardiac hemodynamics. Other data streams may include cardiac acoustics, including analysis of heart sounds, murmurs and sophisticated analyses of hemodynamics related to the heart. Lung function may be sensed as chest movement, auscultatory sounds and nerve firing associated with breathing. Gastrointestinal disease may be sensed as sounds (borborygmi), movement on the abdominal wall, and electrical signals related to smooth muscle activity of the gut. Central and peripheral nervous system activity may be sensed as nerve activity on the scalp (electroencephalogram, EEG), remote from the scalp but still reflecting the EEG, and from peripheral nerve firing.

"Demographics", as used herein, means personal information which may include, but is not limited to, age, gender, family history of disease, ethnicity, and presence of comorbidities and which may be clinically relevant.

"Digital taxonomy" means a partition of different states of disease or health based on quantitative indices. Traditional disease classifications are qualitative, such as "atrial fibrillation is more common in the older individuals, those with heart comorbidities such as valvular lesions or heart failure, those with metabolic syndrome". A digital taxonomy is quantitative, describing an individual's health or risk for a specific disease in terms of quantifiable primary and secondary data elements (data vectors). The likelihood that a disease entity $D_n$ is present in a specific individual is approximated by the probability $p(D_n)$:

$$p(D_n) = \sum_{i=1}^{m} \frac{(k_n p(V_{n,i}))}{k_n}$$

Where m is the number of available data input types, n is the disease being considered, and $p(V_{n,i})$ is the probability that data vector $V_{n,i}$ contributes to disease n for input i, and $k_n$ is a weighting constant for disease n. These elements are integrated in the digital taxonomy, which computes specific probabilities that a specific data input contributes to disease. Probabilities can be obtained from population data, in which a specific person is matched to most-similar individuals in that population. The probability can also be obtained directly from this specific individual alone, at times of health (self-reported or adjudicated) and at times of disease (self-reported or adjudicated). These calculations can be performed by traditional estimating equations but may also by statistical techniques and machine learning. A digital taxonomy represents a disease entity stochastically by the aggregate of abnormalities in multiple related data inputs. This process is dynamic, since the equation reflecting disease will change with additional data inputs, when data changes, and if the state of health or disease are updated. The digital taxonomy is well suited to analyze massive amounts of data from wearable devices in an individual, or massive amounts of data from several individual as a crowd-sourced paradigm.

"Historical data" means stored data, which may include reports from medical imaging, e.g., magnetic resonance imaging (MRI), computed tomography (CT), radiological, or other scans of an organ, data from genetic testing analyses (e.g., presence of one or more genomic variants), previously-obtained ECG reports, pathology, cytology, and other laboratory reports, as well as clinical demographics such as age, gender, family history of disease, and presence of comorbidities. Historical data may further include additional personal historical details that could be relevant to generating the PDP, for example, mental illness, employment in a high-stress profession, number of pregnancies (in women), engaging in high-risk behaviors such as smoking, drug or alcohol abuse, etc.

"Input data" or "data input(s)" means data not directly sensed by a physical component of the system, but data that is utilized by the processing unit in conjunction with sensed data to generate the PDP and digital taxonomy. Input data from a data source may include streams of data detected using other systems, for example, an external ECG or EEG system, clinical, laboratory, pathology, chemical, or other data, or data from a medical imaging device, which data is transmitted to the processing unit.

"Index individual" means a patient or target of a study or evaluation for whom a personal digital phenotype may be generated.

"Machine learning" means a series of analytic methods and algorithms that can learn from and make predictions on data by building a model rather than following static programming instructions. Machine learning is often classified as a branch of artificial intelligence and focuses on the development of computer programs that can change when exposed to new data. In the current invention, machine learning is one tool used to create the digital network linking sensed data with tasks in each individual. Mathematically, some forms of machine learning can be approximated by statistical approaches. Machine learning techniques include supervised learning, transfer learning, unsupervised learning, or reinforcement learning. Several other classifications may exist, but mostly embody the following concepts:

"Unsupervised Machine learning" includes methods such as cluster analysis that may be used to identify internal links between data, potentially such as the link between clinical data (diagnosis of atrial fibrillation), family history, data from physical examination (irregularly irregular pulse), data from sensors, electrical data (irregular atrial signals on the ECG), structural imaging data (enlarged left atria), biomarkers, genetic and tissue data as available.

"Supervised Machine Learning" includes methods that can classify a series of related or seemingly unrelated inputs into one or more output classes without explicitly modeling inputs, i.e., without assuming a potentially incorrect ("biased") mechanistic hypothesis.

"Reinforcement learning" is a form of machine learning related to psychology, which focuses on how software agents take actions in a specific environment to maximize cumulative reward. Reinforcement learning is often used in game theory, operations research, swarm intelligence and genetic algorithms and has other names such as approximate dynamic programming. One implementation in machine learning is via formulation as a Markov Decision Process (MDP). Reinforcement learning differs from supervised machine learning in that it does not require matched inputs and labeled outputs, and actions that result in sub-optimal rewards are not explicitly corrected (unlike supervised learning which may correct suboptimal rewards via e.g., back propagation algorithms in a perceptron).

"Medical device" means an instrument, apparatus, implement, machine, contrivance, implant, in vitro reagent, or other similar or related article, including a component part, or accessory, which is intended for use in the diagnosis of disease or other conditions, or in the cure, mitigation, treatment, or prevention of disease, in man or other animals.

"Neural networks" means self-learning networks of interconnected nodes modeled loosely after the human brain that can be used to recognize patterns. Artificial neural networks can be combined with heuristics, deterministic rules and detailed databases.

"Personal digital phenotype" ("PDP") is a digital representation of health or disease in an individual, which may or may not include cellular, genomic or other -omic data, calibrated to observed response to therapy for an individual. The PDP for an individual is matched to those most similar to this individual from a digital taxonomy of data from a large group. PDP's thus enable personalized medicine without catering just to a statistical majority of individuals. Data elements used to create the PDP may represent the individual's health state, weighted by their likely contribution to disease or health for an individual of similar age, gender and comorbidities. PDPs are matched by algorithmic analyses which take into account the calculated or documented probability of impact on health or disease. This may use deterministic algorithms or machine learning. For example, a heart rhythm phenotype will primarily consider heart rate and electrographic signals (surface ECG and intracardiac). Higher mathematical weighting will be given to these data elements. Data streams from other (indirect) organ systems may include changes in breathing rate with heart rate (i.e., lung sensors), changes in nerve firing with heart rate (i.e., nerve function). Other data elements include abnormal cardiac ejection fraction, location and presence of structural abnormalities of the heart. Historical data including age, gender and family history may also impact the overall digital personal phenotype.

"Population data" used herein is a determinant of the accuracy of the inventive approach. If the index individual is very different from the reference population then the digital taxonomy may not adequately represent this individual. In this case, data will be primarily derived from prior data in the individual ideally at times of adjudicated health and adjudicated illness. If the reference population is broad but has other limitations, such as not being well phenotyped or not having well-labeled data elements, again a taxonomy will not be useful. Thus, the ideal data set comprises data streams that are well labeled, and comprise individuals that are like the index individual, that can be partitioned to create a digital taxonomy. Simply providing 'large' or 'big' data is not sufficient.

"Sensors" include devices that can detect biological signals from the body of an individual. A sensor may be in direct contact with the body or may be remote. When applied to a group of individuals, sensors may represent all or part of a defined population. Electromagnetic sensors can sense electromagnetic signals relating to the electromyogram (EMG), electroencephalogram (EEG), electrocardiogram (ECG), nerve firing or other emitter. The term "sensor", especially when describing certain cardiac applications of the invention in which electrical information is detected, may be used interchangeably with "electrode", "electrode catheter", or "catheter." Electrical sensors can also detect bioimpedance, such as conductance across the skin that decreases when the person perspires, which may occur during times of sympathetic nervous system predominance. Sensors can also detect other chemical changes via current flows. Sensors also include devices that detect temperature, such as a thermistor or other thermal detector. Sensors can detect light such as changes in the color of reflected light form pulsatile heart activity (photoplesthysmography), changes in peripheral oxygenation (e.g., cyanosis, anemia, vasodilation on the skin). Sensors can detect sound via a microphone. This can be used to sense sounds from the heart, lungs or other organs. Sensors can detect other vibrations or movement via piezoelectric elements. Sensors can detect chemicals directly, using specialized sensors for hormones, drugs, bacteria and other elements which are typically transduced on the device to an electrical signal. Examples include motion sensing of chest wall movement from a breath or heartbeat, chest wall vibrations from certain types of breath (e.g., a loud obstructive breathing sound) or heart sound (e.g., a so-called "thrill" in the medical literature). Breath sensors can detect movement of the chest wall, abdomen or other body parts associated with ventilation, or acoustic data (sound) associated with breaths, or oxygenation associated with breathing. Chemical sensors can detect chemical signals on the skin or other membranes that reflect body chemistry such as oxygenation and deoxygenation, metabolic acidosis, stress or other states that will be familiar to those skilled in the biochemistry arts. Sensors can also detect images using a camera or lens requiring contact from the fingerprint or other body part, or sense movement from specific muscles, or sense iris dilation or oscillations from photosensors in a contact lens. Positional sensors can identify position of body parts and changes over time (including gait) or contact sensing of the position of certain body parts at one point in time or over time (e.g., a facial droop, a facial tick or other idiosyncratic movement). In exemplary embodiments of the inventive system, multiple sensors may be used in communication with a central computing device or which may form a network linked via BLUETOOTH®, WiFi™, or other protocol to form an internet of things (IoT) of biological sensors.

"Signals" include electronic, electromagnetic, digital or other information that can be sensed or acquired. Sensed signals are detected unaltered from their natural form (i.e., recorded) with no transformation. Sensed signals are typically biological signals. Sensed signals can be detected by humans (e.g., sound, visual, temperature) but also machines such as microphones, auditory recorders, cameras, thermometers). Acquired signals are detected in a transformed state, such as an ECG recording. Such signals may be biological, since cardiac bioelectricity generates the ECG, or non-biological signals, e.g., vibration sensed after application of sonic or ultrasonic energy, or a haptic signal transduced from a sensed electrical, sonic or other signal. Signals may be sensed via physical contact with a sensor.

"Smart data" means application-specific information acquired from sources that can be used to identify and/or act upon normal or abnormal function in an application. Smart data is thus different from the term "big data". "Smart data" is tailored to the individual as well as being tailored to address the specific task or application—such as to maintain health and alertness or detect and treat disease such as sleep disordered breathing. Tailoring is based on knowledge of what systems may impact the task in question. Such knowledge may be based on physiology, engineering, or other principles. In contrast, "big data" is often focused on extremely large datasets for the goal of identifying statistical patterns or trends without an individually-tailored link. In machine learning parlance, smart data may result from supervised learning of datasets to a known output, while big data simply speaks to the volume of data without necessarily implying any knowledge of significance of specific datasets.

"Sources" for a heart rhythm disorder are used herein to indicate targets for therapy. In the biological literature, an electrical source or electrical driver indicates a focus from which electrical waves emanate outwards, or a reentrant, rotational or rotor-like circuit from which activation emanates. These electrical sources drive the rhythm, such as focal atrial tachycardia, reentry in ventricular tachycardia or atrial flutter. Sources may also drive atrial fibrillation or ventricular flutter or ventricular fibrillation. In the clinical literature, different definitions can be applied, and other targets can be identified that are effective targets for therapy for a heart rhythm disorder. This includes small channels of viable tissue within fibrosis or scar regions of low voltage, regions of complex signals, regions of high frequency or rate of activation (including high dominant frequency). Other electrical targets include regions of conduction slowing, where contour lines of activation ("isochrones") crowd which can be detected during sinus rhythm or during more rapid rates including during pacing.

Other biological terms take their standard definitions, such as heart failure, tidal volume, sleep apnea, obesity and so on.

The following description and accompanying figures provide examples of applications of the inventive system and method for creating personal digital phenotypes (PDP) of health and disease, compared to digital taxonomies, to enable personalized strategies to detect regions of interest for biological rhythm disorders and to treat such regions of interest. The examples described herein are intended to be illustrative only. As will be evident to those of skill in the art, additional variations and combinations may be formed employing the inventive principles disclosed herein.

FIG. 1 illustrates an exemplary system to define personal digital phenotypes (PDP), compare them to a digital taxonomy to personalize the determination or health or disease for an individual, including identification of regions of interest for electrical rhythm disorders, then to deliver personalized therapy to such regions. The input/output (I/O) data 100 includes input signals relating to an individual that have been generated by one or more sensors 105 that may be placed external and/or internal to the body. Therapy devices 110 may be inserted temporarily, such as a treatment catheter, or may be implanted. Implanted devices may be inserted expressly to develop/maintain the PDP, to provide health maintenance, or to provide continual therapy. Additional inputs 125 include clinical data, patient history, physical data, and/or data from electronic medical record systems. Devices may communicate by an Internet of Things (IoT), with time-stamped data being sent to the input unit 130 via connected or wireless means. The data may be communicated continuously, near-continuously, real-time, near-real-time or some other format or combination of time-acquired signals.

Several types of sensors may be used, including photosensors, piezoelectric, acoustic, electrical resistance, thermal, accelerometers, pressure, flow, electrochemical, or other sensor types may be used to measure chemical, light, skin activity/moisture levels, pressure, movement, and other parameters relevant to development of the PDP. Selection of appropriate sensors will be apparent to those of skill in the art. Sensors can be interchangeable or fixed in each embodiment. Selection of appropriate component values (resistors, capacitors, etc.) and circuit performance characteristics, as well as addition of supporting components/circuitry (filters, amplifiers, etc.), will be within the level of skill in the art and are not described herein.

In this exemplary implementation of the system, signals are sensed from the heart and may comprise several types. Heart electrical activity can be sensed directly using sensors that may be placed on the heart and either in contact or not, sensors near other body regions (e.g., esophagus, bronchi and airways, mediastinum), on the body surface, or not touching the body, e.g., magnetocardiography, which senses magnetic fields generated by heart electrical activity. Sensors may also measure cardiac motion or presence of ischemic regions by detecting cardiac motion or the movement of blood through it. Cardiac motion can be sensed using non-electrical devices e.g., echocardiogram or ultrasound, from movement on regions of the body from cardiac motion (ballistic cardiography), from electrical impedance change due to alterations in heart chamber volumes. Blood flow can be detected using known methods such as Doppler echocardiography, 4D-flow MRI, or imaging methods that tag a carrier such as red cells. In various embodiments, these sensors can be used separately or in different combinations, and further these separate or different combinations can also be used in combination with sensors inserted into the patient's heart. Signals may be sensed without physical contact with a sensor. Examples of such methods include sensing a heartbeat from emitted electromagnetic fields from the magnetocardiogram (MCG), or from infrared signatures of cardiac motion. Other noninvasive sensed signals may include auditory breath sounds or heart sounds from a sensitive external microphone. Signals from one or a combination of the described sensors are sent via wired or wireless communication to input unit 130.

Nerve activity is another sensed signal that may be used in the invention, with indices such as rate and periodicity of firing, periodicity during the day and between days, types and patterns of nerve firing, and spatial distribution of these measures. In one embodiment, non-invasive recordings are made from skin patches, but other embodiments could use the electroneurogram (ENG) where an electrode is plunged into the skin to record from nearby neural tissue. Invasive approaches may be suitable for inpatient care but less suited for continuous recordings or consumer applications. Sensors can record from different regional nerves if placed in different regions, e.g., electrodes on the chest may measure nerve activity related to the heart or its nerves, electrodes on the neck or head may measure neural signals including those controlling the heart, or other locations familiar to one skilled in the art.

Lung (pulmonary) function activity is another type of sensed signal, and may vary independently of the heart, or as a result of alterations in the heart. This can be measured by sensors of breath sound, chest wall movement, oxygenation, electrical activity of the phrenic nerve or other sensors.

A therapy tool or effector 110 enables maintenance of health or treatment of disease. This may comprise an electrical stimulator, a thermal stimulator, an optical stimulator, a chemical release device (such as for pharmacological therapy such as an infusion pump), or other stimulator. In one embodiment, this is an ablation catheter to treat heart rhythm disorders, passed via vascular access labeled as 120.

Input data 125 are used for personalization and to reference the index individual to population data represented as the disease taxonomy. Input data 125 may include demographics, laboratory, chemistry, and image data. For example, some data inputs for a person may include "static" stored data, such as date-of-birth (age), gender and race. Input data may also include near-real-time data such as patient movement from a separate device (e.g., a treadmill, motion sensor in a building), patient ECG or cardiac information from separate device (e.g., hospital telemetry, ICU bed monitors), breath sensors, time-lapse or time-series data from a separate device (e.g., periodic counts of blood sugar from a glucometer), or other data input. Input data can also include indexes of familial tendency for disease (Mendelian or non-Mendelian), identifiable genetic loci, variations in weight, or susceptibility to toxins such as tobacco or alcohol. Input data are sent via wired or wireless connection to input unit 130, with time-stamps.

The input unit 130 is the data hub, which may be a physical device or a cloud-based interface for multiple digital data streams transmitted to it. Data are time-stamped and may be kept separate as real-time (streaming) or stored (historical).

Conventional cloud-based computing/storage 135 may optionally be used to store data in addition, or as back-up, to that stored on devices in 105 or 130, and/or to perform processing of the data. Raw data and analysis results saved or generated in cloud-based computing/storage may be separately communicated to external servers connected via the Internet. For example, independent recipients may include a research facility, clinical trial administrator, or other recipient authorized by the patient.

A population database 140 provides a reference for data from this index individual and may include stored data from a population, time-varying streamed data, optional streams which could be crowd-sourced.

The process controller 145 is programmed to execute algorithms that include deterministic formulae as well as neural networks (or other learning machines) and other distributed representations to create a personal digital phenotype (PDP) 150 which is compared to a digital taxonomy 155, classifying data from prior timepoints for the index individual based on population database 140. In one embodiment, machine learning is used to process input data, develop and learn classifications linking complex physiological and clinical inputs to outcome at a patient-level (i.e., develop PDPs), compare these to quantitative traits in a relevant population (a digital taxonomy of health or disease), to prospectively design "optimal" or "personalized" therapy based on specific individual characteristics relative to prior observations in that individual, prior observations in a comparator population, or mathematically inferred predictions.

The comparison between PDP 150 and digital taxonomy 155 identifies and/or tracks the patient's status, i.e., health or disease. This is done by computing deviations from normal in the index individual compared to pre-specified "tolerance limits" and comparing to different populations. In an embodiment, this is accomplished by sensing data streams from sensors 105 or repeatedly updated data. Data may be input during periods of adjudicated "health" for that organ system in that person, or during periods of adjudicated "disease". Accumulated data assists future learning to validate PDPs. Different states may be detected for altering conditions or grades of health or disease (for instance, exercise versus rest) between individuals. This approach differs from current medical practice, in which a "population" range for "normal" and "disease" is applied across multiple patients with little scope to tailor them to the individual. It is this aspect of the inventive approach that provides "personalized medicine" or "precision medicine".

The status identified through the comparison between PDP 150 and digital taxonomy leads to personalize disease and health management 160, which is then communicated to a diagnose and reporting unit 165 or to guide therapy 170. The diagnosis/report unit 165 can be a smartphone app, a dedicated device, or an existing medical device. Briefly referring to FIG. 3, a custom-designed smartphone app 470 can show the site of termination from digitally acquired personal data from an imaging/mapping system. The sample display panel can show the personal streaming data of an AF map created by freely-available online methods playing in a smartphone app. The display panel can provide interactive input with the physician to assist in identifying the critical site for personalized therapy.

In one embodiment for use in heart rhythm disorders, the therapy unit controls electrical interventions (pacing) or destructive energy (ablation). The effector device 110 shown in FIG. 1 can be activated to ablate tissue to treat the biological disorder in a way that is tailored to personal phenotypes. In alternative embodiments, the therapy unit may deliver anti-arrhythmic drugs or anti-inflammatory drugs by an infusion pump, or gene or stem cell therapy. In another embodiment, therapy can be mechanical constraint can be delivered, to ameliorate stretch which can trigger arrhythmias.

Figure 2:
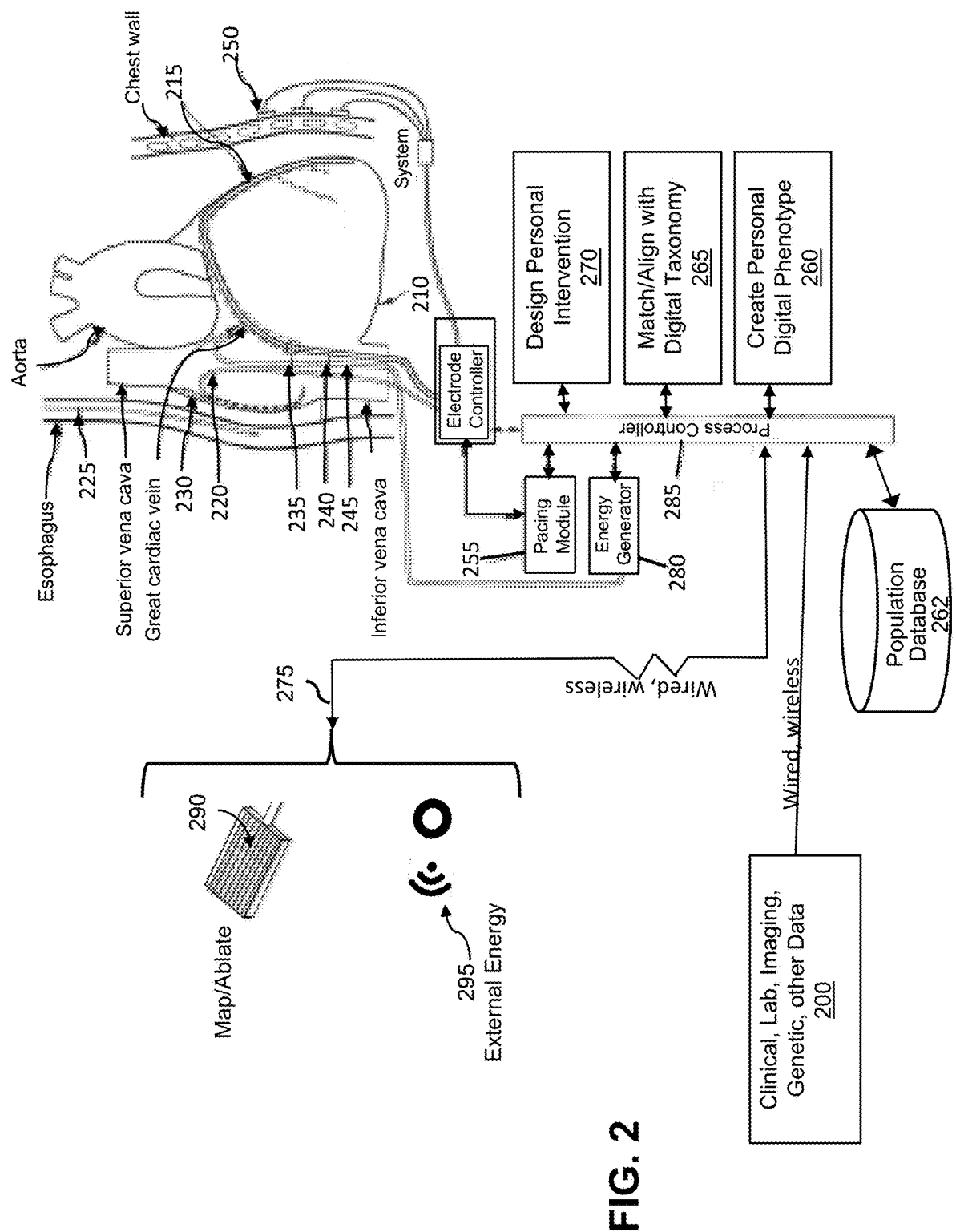
FIG. 2 illustrates use of personal digital phenotypes in the inventive system for the heart, integrating streamed data from the heart or other organs with input data, with outputs designed to diagnose or treat regions of the heart, in accordance with one or more embodiments.

FIG. 2 diagrammatically illustrates an exemplary system that uses personal digital phenotypes (PDPs) for an embodiment for treatment of heart rhythm disorders. Sensed or stored data 200 may include clinical, laboratory, genetic, or other data. Examples of data may include markers of abnormal inflammatory or immunological states of the body, and biological markers of atrial fibrillation or ventricular fibrillation. Direct measures of inflammatory/immunological equilibrium include, but are not limited to, counts of inflammatory cells or concentrations of cytokines in body fluids or in an affected organ. Indirect measures of inflammatory/immunological equilibrium represent the protean impact of inflammation on various organ systems abnormalities in static and diurnal measures of body temperature, body fluid composition, heart rhythm, nerve firing rates, and the encephalogram. Additional data may include detection of abnormal neural control of the heart and body, enabling modulation of such states to maintain, enhance or correct biological rhythms including atrial fibrillation or ventricular fibrillation.

Input data are evaluated iteratively, compared to normal and abnormal values for that individual as well as to populations, and directing interventions and therapy to maintain normal equilibrium. In this context, "sensing" signals goes beyond traditional collection of raw signals from a detection device, and may include data generated from other test procedures, e.g., clinical, laboratory, chemical, etc. As shown in FIG. 2, data 200 may be generated by devices that sense electrical signals, for example, ECG or bioimpedance sensors, combined with a transmitter for communicating the detected signals to process controller 285 by wired or wireless transmission. Other repositories or repository of streamed or input data obtained from clinical systems, hospital databases, hospital devices, or laboratory equipment may also interface with process controller 285.

The heart 210 can be measured in many ways including ECG electrodes applied to the body surface 250. Electrical or electromagnetic signal sensors such as electrode catheters in the esophagus 225, electrodes in the right atrium 230, in the atrial septum or left atrium 220, or via the great cardiac vein to the coronary sinus (electrodes 235, 240, 245), to the anterior cardiac vein (electrode 215) that accesses the left or right ventricle, or directly to any of these chambers. Sensors 215-245 may also detect activation from other regions of the heart.

Cardiac sensors may be external or internal. In some embodiments, one or more of the sensors may be external to the patient's heart. For example, sensors 250 detect cardiac activation via the patient's surface (e.g., electrocardiogram—ECG). Sensors (not shown) may detect cardiac activation remotely without contact with the patient (e.g., magnetocardiogram). As another example, some sensors may also derive cardiac activation information from cardiac motion of a non-electrical sensing device (e.g., echocardiogram, Doppler signals of blood flow, red cell tagged scans). Such sensors can be classified as "external sensors" to distinguish them from catheters and electrodes that are inserted into the patient's body, into or near the heart (or other organ), i.e., "internal sensors." In various embodiments, a variety of external sensors may be used separately or in different combinations. Further, these separate or different combinations of external sensors can also be used in combination with one or more internal sensors.

Process controller 285 accepts sensed and input data. In some embodiments, process controller 285 is configured to analyze unipolar signals; in other embodiments, it analyzes bipolar signals. Process controller 285 uses these sensed data streams to create a personal digital phenotype (PDP) for the individual. This is compared to a digital taxonomy of relevant previously stored data 265, i.e., the arrhythmia. Process controller 285 may have access to population data in population database 262 (also shown in FIG. 1 as database 140) to create the digital taxonomy. An intervention is then designed to diagnose or treat that individual based on her/his personal digital phenotypes 270.

In some embodiments, process controller 285 analyzes input electrical data to generate map(s) representing source(s) or other target(s) of the heart rhythm disorder which can then be displayed on an output device. Population database 262 can be used to store intermediate data. Population data 262 can support or aid signal analysis and can store maps of potential target regions or source locations for other individuals with known personal digital phenotypes as part of the digital taxonomy.

Internally, process controller 285 typically comprises a digital signal processor. It may also include a graphical or other processing unit to execute machine learning algorithms or other computations of PDPs to compare against the digital taxonomy to guide therapy. Other elements may include traditional computing machines, cloud computing, biological computing, or biological-artificial (cybernetic) devices. Referring briefly to FIG. 1, the functions corresponding to input unit 130 and process controller 145 would be among the computing operations executed within process controller 285.

Process controller 285 is programmed to implement functional modules to generate personalized digital phenotypes of cardiac (rhythm) in the individual (PDP module 260, which corresponds to element 150 in FIG. 1), match or align the PDP with digital taxonomy (taxonomy module 265, corresponding to step 155 in FIG. 1) using data from population database 262, to design personalized interventions (design module 270) and guide delivery of interventions 275.

Personalized therapy designed in module 270 then delivered at delivery element 275. Delivery element 275 may employ several effector devices such as a sense/ablate multielectrode catheter 290 or an external energy source 295. Other therapy devices may include direct electrical outputs, piezoelectrical devices, visual/infrared or other stimulatory systems, nerve stimulating electrodes or even virtualized data such as avatars in a virtual world interface or elements in a large database that can be queried, as well as other effector elements evident to those skilled in the art.

In the illustrative embodiment, therapy can include pacing. For example, instructions generated in module 270 cause the process controller 285 to pace from pacing module 255. Pacing can be applied through electrodes 250, 215, 230-245, 290 or 295. Therapy can be ablation using energy generated by energy generator 280 to modify tissue. Internal electrodes (e.g., 215, 230-245), a dedicated ablation catheter 290 or external energy source 295 can ablate from energy generator 280. Other forms of energy include, e.g., heating, cooling, ultrasound, laser using appropriate devices controlled by the process controller 285 and other modules. Therapy is personalized by delivery to tissue subtending an electrical and/or structural target determined by PDPs. Other therapy units may deliver anti-arrhythmic drugs using an infusion pump, anti-inflammatory therapy (since inflammation may be a proximate cause of arrhythmias including fibrillation), gene or stem cell therapy. In another embodiment, therapy to deliver mechanical constraint can be delivered, to ameliorate stretch which can trigger arrhythmias. Therapy using external energy sources 295 can enable a fully non-invasive therapy in which critical targets for arrhythmia are identified then treated without invasive strategies.

Figure 3:
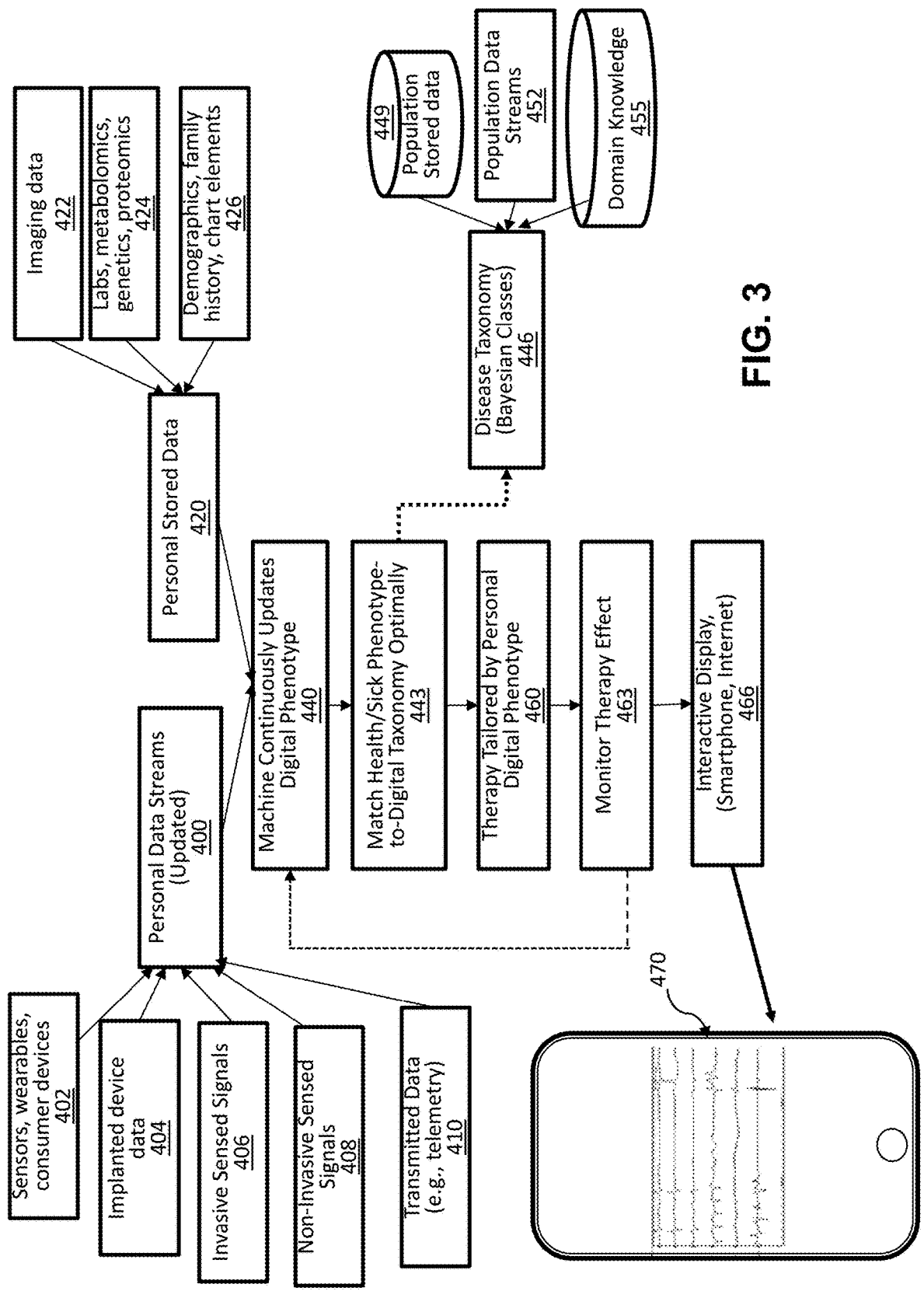
FIG. 3 illustrates general use of personal digital phenotypes, to make a diagnosis, deliver therapy and track/display therapy response for an individual, in accordance with one or more embodiments.

FIG. 3 summarizes an exemplary workflow using PDPs to guide and monitor therapy. Two forms of input are used: personal data streams 400, which can be updated over time, and personal stored data 420. Data streams 400 may include sensed data from novel or existing sensors 402, such as from wearable devices or consumer products, implanted devices 404, invasive sensed signals 406 from existing or dedicated devices including minimally invasive products such as a skin, nasal, corneal, buccal, anal or auditory probe, from non-invasive sensors 408, which may provide data including motion, and temperature from infrared probes, and from transmitted data 410, such as telemetry from existing medical equipment.

Personal stored data 420 may include static data such as imaging data 422, ideally including detailed coordinates of regions of scar, fibrosis, ischemia, reduced contractile function and potential border zone tissue, laboratory values 424 including serum biochemistry but also genetic, proteomic, and metabolomic data (when available); demographic data 426 and elements from the patient history such as presence of diabetes mellitus or hypertension, left atrial size from echocardiography. Additional personal stored data may include outcome data such as subjective symptoms of whether a patient feels well or not, e.g., "healthy" or "less healthy". Outcome data may also include objective data such as acute endpoints of a therapy such as resolution of fever by an antibiotic or, in an embodiment, termination of atrial fibrillation by ablation. Objective evidence may also include chronic endpoints such as absence of infection or lack of atrial fibrillation recurrence on long-term follow-up.

The inventive approach may also use combinations of population data including population stored data 449, population data streams 452, and domain knowledge 455 to define disease taxonomy 446 to identify health and illness, to partition data classes based on health-state, and to compare population classes with the individual.

Step 440 continuously updates personal digital phenotypes from the data streams 400 and stored data 420. This can be done periodically at pre-determined timepoints or continuously. Step 443 performs a comparison of the personal digital phenotype to externally-determined digital disease taxonomy 446, generated from one or more of population stored data 449, population data streams 452, and domain knowledge 455. These steps are detailed further in FIG. 5.

In step 460, therapy is tailored to the personal digital phenotype, and in step 463 the effect of therapy is monitored iteratively using data streams in the context of already stored data back in step 440. According to the inventive approach, phenotypes are based on the ground truth (label) of whether a patient is ill or not, how ill they are, and how best to treat them to maintain health or treat illness. These clinically- and biologically-relevant operations are included at steps 426, 446-455. The invention acquires novel data in steps 402-410 to create personalized phenotypes, using data types that may not always correspond to data types in stored data in that individual (420-426) or in a comparator population 446-455. Such data types are actively acquired by the system so that personal phenotypes can better guide therapy and include data types including electrical information or heart structure.

Finally, an interactive interface to report data is provided in step 466. Display 470 provides one example of the many types of data that can be displayed via an application on a computer or mobile device. (In the illustrated example, a smart phone is shown.) An app implementation has been created for an APPLE® iPhone® written in Swift via Xcode. The image 470 shows sample maps of the arrhythmia with ablation targets, and may additionally include one or more of a 3-D heart image, numerical coordinates, text descriptions, and quantitative scores. The invention displays features of personal digital phenotypes for each individual, with some indication of personalized management and therapy decisions. Step 466 generates a smartphone display 470 of these data, with an illustration as a smartphone app.

Figure 4:
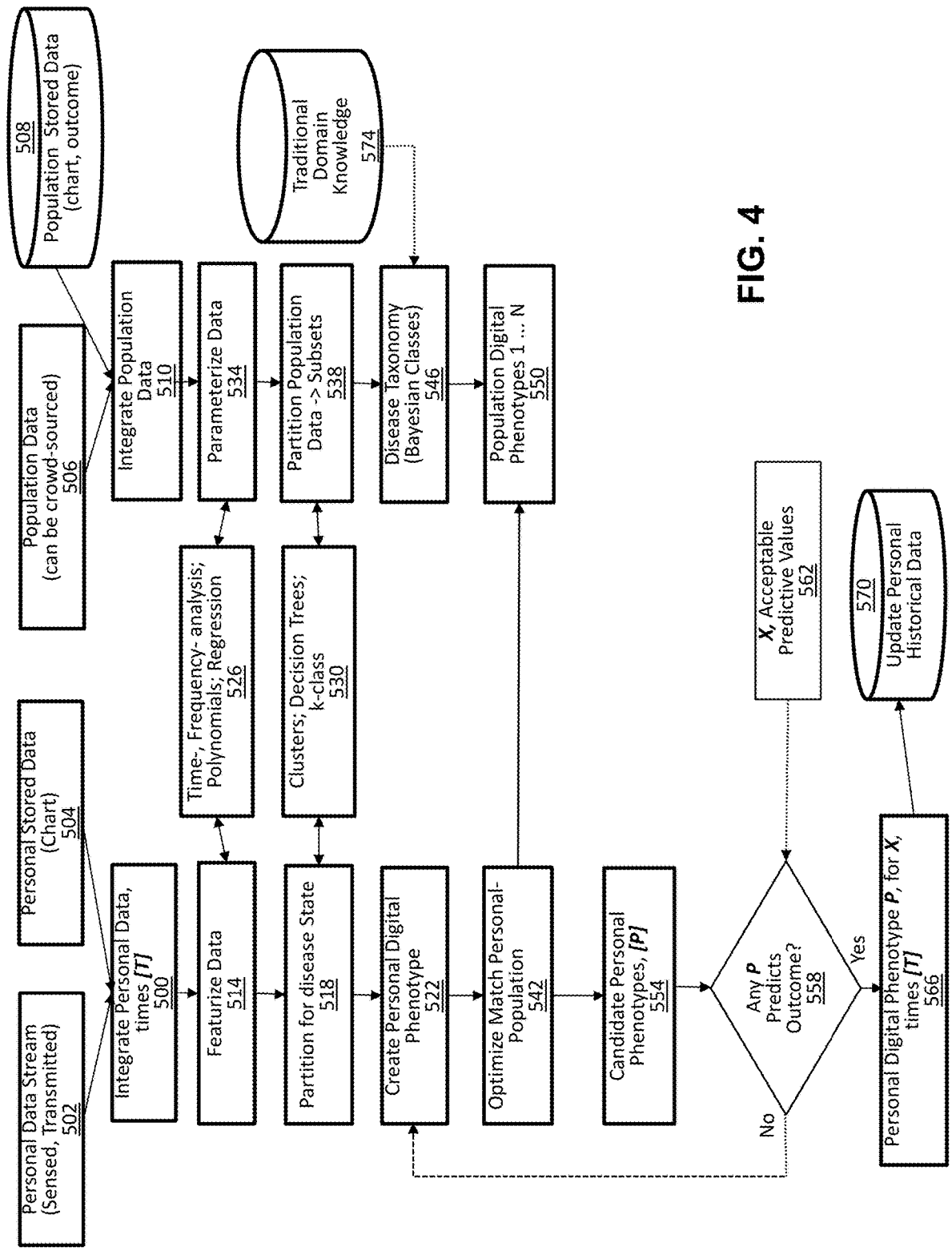
FIG. 4 is a flow diagram illustrating creation of personal digital phenotypes compared to digital taxonomies, in accordance with one or more embodiments.

FIG. 4 provides a more detailed workflow to create PDPs and the digital taxonomy, and to compare them. Step 500 takes personal data at time vectors [T] comprising one or more timepoints. This includes data streams 502 (corresponding to step 400 in FIG. 3) and personal stored data from a chart 504 similar to personal stored data 420 in FIG. 3. This data includes measures of biological or clinical significance such as acute or chronic outcomes.

Population data streams 506 (block 452 in FIG. 3) are designed to make use of increasingly available datasets. Such streams may include data from individuals with similar or different phenotypes relative to the index individual. To provide a few examples, this data may include telemetry data from patients in an intensive care ward, individuals using a similar wearable device, or soldiers in the field being monitored for various vital signs.

Data from a stored population database 508 (database 449 in FIG. 3) are incorporated at a granular level based on similar digital phenotypes. This differs from the approach of using traditional statistical associations that tend to be weak, such as the significant association between AF and obesity which fails to account for thin individuals who develop AF or obese individuals who do not. Other granular-level patient features may be common between such different patients, such as heart disease or hypertension in patients with AF who may be thin or obese. Similarly, atrial scar on imaging is associated with AF, yet many individuals with AF have minimal scar while some without AF have considerable scar. The numerical matching of patients based on PDP features enhances the ability of the invention to tailor therapy for an individual based on known outcomes in similar patients. Statistical associations are also performed using multivariate analyses.

Population data from database 508 are integrated in step 510 (similar to step 446 in FIG. 3) including indices of biological or clinical significance such as acute or chronic outcomes which serve as a reference for diagnostic or treatment utility. The first step is to featurize the data in step 514 to address the curse of dimensionality in machine learning. Feature reduction and feature extraction techniques are well known in the art and may vary depending on the type of learning machine that is used, or may be implemented using different types or combinations of learning machines or other algorithms. Possible operations for feature extraction in step 526 include time domain mathematical operations including principal component analyses, averaging, integration, area analysis and correlations. Frequency domain analyses include Fourier analyses, wavelet transforms, and time-frequency analyses of fundamental frequencies, harmonics or other frequency components. Polynomial fitting can also be used to represent data as polynomial coefficients. Other generic featurization steps can be used, using widely available libraries such as TSFresh (Time Series FeatuRe Extraction). In parallel, population data are parameterized in step 534 using similar or different operations.

Step 518 partitions data into classes that represent a digital 'disease phenotype' in an individual, or a digital 'disease taxonomy' in a population. The goal is to better segregate data—clinical data, but also granular invasive data points and lab tests—into partitions of individuals who may appear similar but have different outcomes from a given therapy (successful versus unsuccessful). Mathematically, this is done by constructing 'hyperplanes' in k-parameter space that separate patients who have one outcome from those who do not. For the embodiment of arrhythmias, for instance, it remains unclear why 'paroxysmal' AF in two patients with similar profiles may respond completely differently to medications or pulmonary vein ablation. Personal phenotypes code observations from multiple patients to crowd-sourced partitions ("digital taxonomy") of why AF in some patients but not others reflects source or driver regions, structural abnormalities, neural components and metabolic comorbidities including obesity. These factors are not predicted by the traditional taxonomy of 'paroxysmal' or 'persistent' AF. Using PDPs, inferential methods including statistics and machine learning can be used to compare data to reference populations to infer best management.

Step 530 partitions the data as a classification approach. Partitioning can be performed by many techniques known in the art including, but not limited to, cluster analysis and other types of unsupervised learning, or supervised learning methods including support vector machines (SVM), logistic regression, naïve Bayes, decision trees, or other approaches. This partitioning is done for personal data (step 518) and in parallel population data (step 538). It should be noted that the partitioning techniques used may differ for each step.

Cluster analysis, a known unsupervised learning technique, may be used in step 530 to group unlabeled data (e.g., data streams from multiple sensors, input data, other) into a collection of items that are "similar" to one cluster but dissimilar from others. This can occur even without obvious natural groupings, which is often true in these applications since typical phenotypes rarely include clinical data, imaging and continuous data streams. Clustering is a powerful tool in this invention, but since the final cluster pattern depends on the initial cluster, any ambiguity in identifying the initial cluster patterns could lead to bias. The result of the clustering is validated later in step 558.

Step 546 creates a disease taxonomy from population data using mathematical models to integrate data streams and stored data from the population (database 508), data reduction schemes (step 534) and data partitions (step 538). Data from domain knowledge database 574 is incorporated to filter mathematical relationships. For example, mathematical weighting can be minimized for breast cancer in men, which is rare, or for AF in young children, which is rare, while raising mathematical weighting for aging in men with coronary disease, which is common. Such traditional domain knowledge is available from epidemiological data and population statistics, may also be available from stored population data, and is easily translated to mathematical weightings.

Step 550 creates population digital phenotypes from the disease taxonomy. In other words, the population digital phenotypes correspond to partitions of data that form self-consistent disease classes from quantitative data. These may be clinically obvious, or clinically obscure—e.g., the link between low magnesium levels and atrial fibrillation in some studies. These partitions are each expressed statistically with confidence intervals and will be used for comparisons against personal digital phenotypes.

Step 522 creates a prototype personal digital phenotypes using personal disease partitions from step 518 as a base. Step 542 compares the personal digital phenotype (PDP) to find a best match population digital phenotype. Candidate personal phenotypes are given by a matrix of vectors [P] in step 554. This comprises multiple data elements, data types, some ordinal, some vectorial, and some time dependent.

In some embodiments, supervised learning is used to refine digital phenotypes to predict defined outcomes. This involves feature selection, choice of network architecture, and appropriate data for training and testing.

Features will be identified and "tuned" for machine learning to avoid overfitting (i.e., poor generalization to future unseen inputs) by deliberately creating sparse input "vectors." The invention eliminates redundant features and maximize diversity of input features to comprehensively span the underlying input data.

In one embodiment, features are grouped into three types: (a) traditional clinical variables (demographics, comorbidities, biomarkers); (b) electrical signals (12-lead ECG and intracardiac signals, of which signal processed parameters can separate AF phenotypes; and (c) imaging data including but not limited to 2-D echocardiogram images (atrial geometry), 3-D CT data (geometry), 3-D MRI data (fibrotic areas, geometry), and 3-D electroanatomic shells of voltage and complex electrogram distribution generated at EP study. Clusters (unsupervised learning) can be used for data reduction and can be used as additional input features. To understand the significance of features, filtering and regularization are used. The inventive approach eliminates variables not associated with response classes in training. One approach uses the least absolute shrinkage and selection operator (LASSO) that combines advantages of filter and wrapper methods to minimize prediction errors and includes variables that contribute to regression analyses in the final model.

Missing data in each feature group will be treated by inserting (inputting) the: a) median value; b) predicted value using multiple imputation (a technique from statistics); c) expected value of that data-type from the literature; and d) constant signifying missing data. Each approach will be compared during training of various network models.

Formatting of input images and signals. The invention will format each 3-D MRI, CT or pseudocolored atrial electroanatomic image (denoting anatomy, distribution of specific types of electrogram, e.g., voltage) as 3-D matrices. Time-series data (12-lead ECG, bipolar coronary sinus electrograms, unipolar intracardiac electrograms) will be processed prior to entering the final network, using feature extraction, cluster analysis and pre-processing networks.

The outcomes used to train the phenotype will vary with each application. For the embodiment of heart rhythm disorders, several outcomes may be used to train phenotype. One outcome may be high voltage versus low voltage (such as <0.1 mV) electrogram signals; phenotypes associated with high voltage signals may have higher treatment outcomes. Another potential outcome is the presence of clean spatial maps of AF, showing consistent rotor or focal sources/drivers; these sites may be effective treatment targets. Another desirable outcome is AF termination by drug therapy or ablation, or long-term success from drug therapy or ablation. Both can be determined retrospectively in the reference population to form the digital taxonomy, and then used to identify personal phenotypes that match.

In one embodiment, supervised learning, typically implemented as an artificial neural network ("ANN"), is used to represent the diverse input data and data streams for the individual person and population. ANNs typically comprise three elements. First, a connection pattern between different layers of nodes (artificial neurons), forming networks of variable number of layers each containing multiple nodes per layer. Implementations can be as simple as the perceptron, adaptive linear networks, or many other designs including deep learning networks. The actual network design can be adaptive to the specific task and complexity of the data partitions Second, connection weights between nodes can be varied and updated according to multiple learning rules. Third, the activation function: determining how each weighted input is converted to its outputs. Typically, the activation function $f(x)$ is a composite of other functions $g(x)$, which can, in turn, be expressed as a composite of other functions. A non-linear weighted sum may be used, i.e., $f(x)=K(\Sigma_i w_i g_i(x))$, where K (the activation function) may be sigmoidal, hyperbolic or other function.

A variety of connection patterns, weight and mathematical activation functions can be selected, and a variety of updating functions are possible for any embodiment. Specific forms are optimal for different disease states and tasks. For example, the machine for detecting abnormal heart rate during known atrial fibrillation would be less complex than the machine for identifying the site for ablation in atrial fibrillation, for predicting the onset of atrial fibrillation, for predicting an exacerbation of heart failure or for predicting the onset of coronary ischemia.

Alternative forms of learning include supervised and unsupervised methods including linear logistic regression, support vector machines, decision trees in "if-then-else" statements, random forests and k-nearest neighbor analyses. Such formulations can be applied independently, or as part of machine learning to augment or create boundaries between desired decisions such as the presence (or absence) of sources for atrial fibrillation or other associations linking input data with clinical or physiological outcome for an individual. Several other forms of machine learning can be applied, and will be apparent to an individual skilled in the art.

Various connection patterns, weighting, node activation function and updating schemes can be selected, and specific forms are optimal for different applications depending on the data inputs. For instance, imaging inputs and continuous data series (e.g., electrogram signals) may be represented by different networks, optimized in an embodiment with substantial training data, to each dataset in a given reference population. Thus, depending on the application, the invention can be tailored to best represent EEG data, cardiac and respiratory signatures, weight, skin impedance, respiratory rate and cardiac output. Recurrent neural networks are a data structure which enable analysis of how the network achieves its trained conclusions. Manually engineered scalar features (e.g., clinical data elements) can be incorporated using fully connected layers. Featurized time series (i.e., 12-lead ECGs or so-called 'electrograms' from inside the heart) are processed via convolutional neural networks. Standard techniques of dropout, batch normalization, and hyperparameter tuning are used to avoid overfitting.

A feature of machine learning approaches is that they do not need a priori knowledge of the specifics of human pathophysiology, but instead learn patterns of sensed signals and input data in health and deviations in disease. Thus, they are well suited for personalized medicine where current mechanistic hypotheses may be suboptimal.

Step 558 determines which candidate phenotype(s) can be validated, i.e., which predicts any hard outcome measure. For AF, this may be sites where ablation terminated AF. For coronary disease, this may be clinical constellations that predict critical stenosis of epicardial coronary vessels, i.e., an advanced coronary risk score. By extension, such candidates can be defined for non-heart diseases. If a match is not achieved, either the process of creating the PDP 522 is repeated or the acceptable tolerances X (block 562) are widened. If a match is achieved within acceptable tolerances (vector X), the candidate becomes the Personal Digital Phenotype P within tolerances X at times Tin step 566. The phenotype is then used to update the personal historical data for that individual in database 570, against labeled outcomes used to validate the phenotype. This step is used to validate clusters defined in preceding steps as well as for supervised training.

Figure 5:
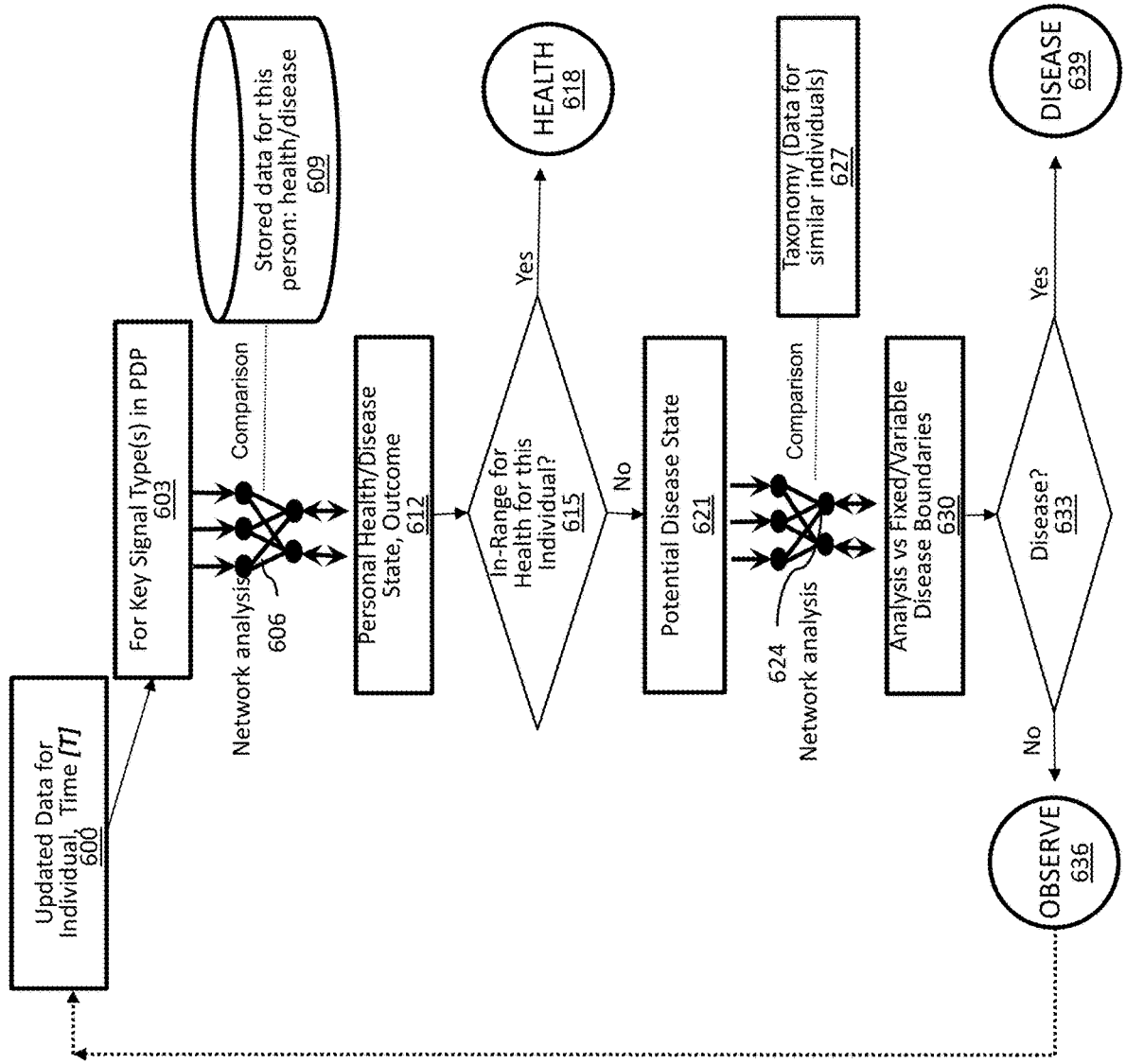
FIG. 5 illustrates how personal digital phenotypes are compared to stored normal values for an individual, or to population values, to indicate health or disease, in accordance with one or more embodiments.

FIG. 5 illustrates how personal digital phenotypes define the interface between health and disease. Step 600 takes each PDP at time T' and examines the key signal types in the phenotype 603. Mathematical and network analysis 606 are used to identify abnormalities, compared first to stored personal phenotypes in database 609, e.g., data from adjudicated times when the individual was feeling well, or feeling unwell (symptoms), or had objective evidence for disease, e.g., an AF episode or not. Step 612 generates a portrait of personal health or disease based on this analysis.

Step 615 then determines if the portrait from step 612 represents health 618 or not, for the individual, within accepted tolerances. If the result is "out-of-range" for healthfulness in the individual, the individual may have entered a potential disease state in step 621, and mathematical and network analysis 624 is performed and compared to population disease taxonomy 627 to determine if the abnormality for the individual falls into "out-of-healthful range" for the population as well. On comparison against population fixed and variable definitions of abnormal, defined statistically (step 630), the invention now asks if disease is present in step 633. If "yes," then disease 639 is declared; If not, in observe step 636, the patient continues under careful surveillance. In either case, the process will be repeated for continued monitoring.

Figure 6:
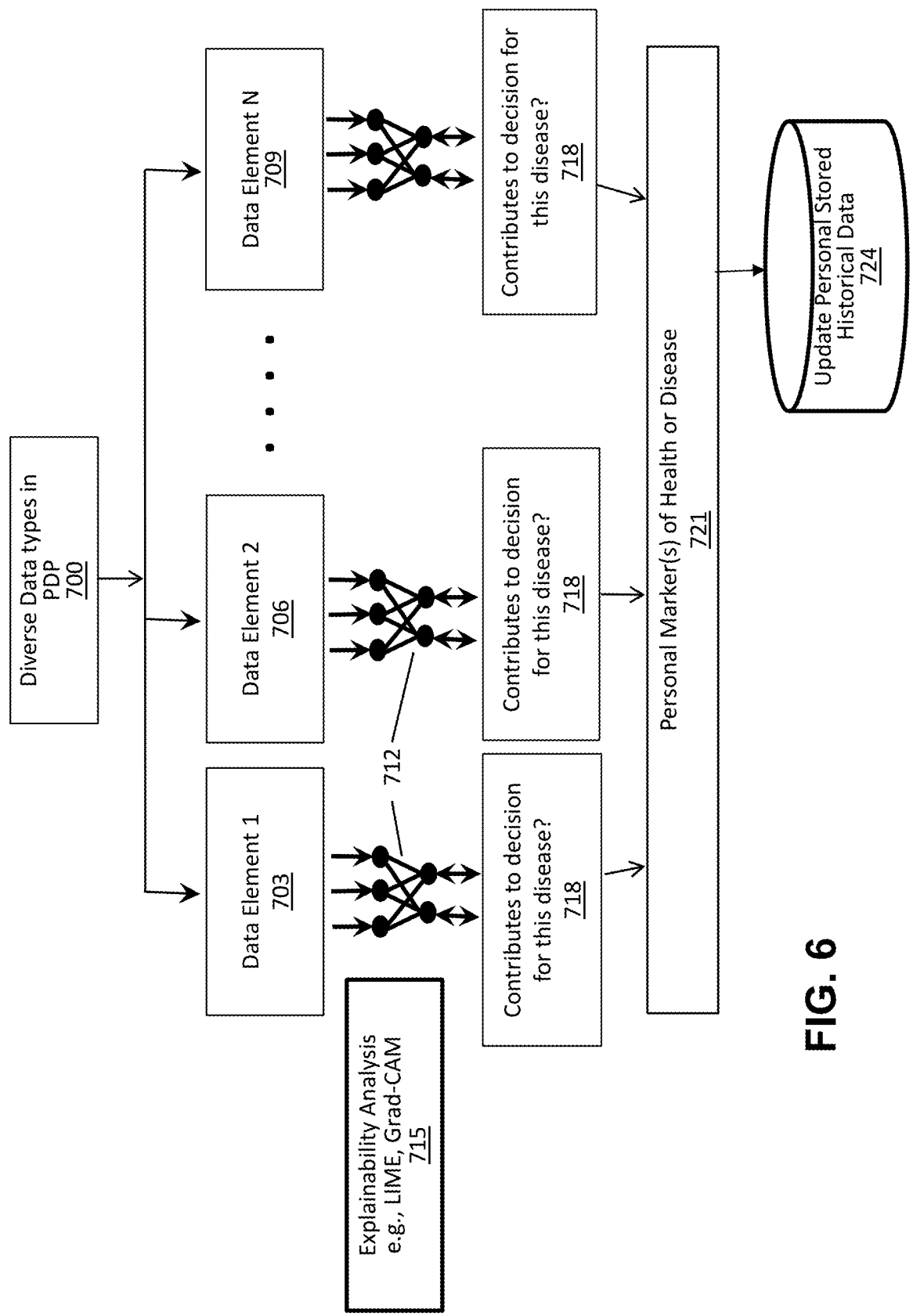
FIG. 6 summarizes the process flow for explaining which data elements are critical for demarcating health or disease in the personal digital phenotype, in accordance with one or more embodiments.

FIG. 6 outlines the explainability analyses for the inventive method, which aims to identify data components that are most relevant for a specific disease or facet of health. This enables a 'disease-specific PDP'. Explainability also addresses a criticism that several data science techniques including machine learning can be a "black box". Several approaches for explainability are used, including expert domain knowledge to featurize data and techniques such as LIME and Grad-CAM as described below. Step 700 analyzes diverse data types in the PDP. Steps 703, 706 . . . 709 consider each data element in turn (input data or data streams), to determine which contributes to decision making for that disease process or facet of health in steps 712. Several approaches (step 715) can be used to determine which component(s) dominated or otherwise contributed to the classification of "disease" versus "health".

Several explainability (or interpretability) techniques can be used, which will be familiar to one skilled in the art. One includes the use of attention layers in recurrent neural networks. Alternatively, Local Interpretable Model-agnostic Explanations (LIME) can be used to explain predictions by approximating an interpretable model. LIME can be used for 1-dimensional data such as the ECG or electrical signals from within the heart (electrograms), numeric features or images. Another approach is Gradient-weighted Class Activation Mapping (Grad-CAM), which identifies the most critical nodes as the largest weight multiplied by backpropagated pooled gradient downstream to the final convolutional layer. Another embodiment specifies features that should or should not be part of the model including spatial domains in images (e.g., size of an atrial driver region, or ventricular conduction velocity, or spatial extent of fibrosis in the human heart) enabling tailored interpretation to domain electrophysiological "concepts" to ensure that models do not converge on irrelevant concepts. An example of this is the Testing with Concept Activation Vectors (TCAV) approach. This can examine specific features that should or should not be part of the model (e.g., size of AF driver regions), enabling the invention to tailor explainability to accepted "concepts". As another example, prediction of an AF outcome (e.g., success or failure of ablation) can be tested by an interpretable model, e.g., presence of fibrosis near the right atrium. This approach attempts to ensure that numerical models are relevant to predictions, and models do not converge on irrelevant concepts. Explainable features predicting outcome will thus be identified quantitatively. Clinical rationale can subsequently be added 574 via domain knowledge, e.g., the determination that obesity predicts negative outcome from ablation or drug therapy, while hair color predicting positive outcome may not. Data on populations in whom class IC anti-arrhythmic drug (AAD) may be used can also be included.

A feature of the digital taxonomy is to code discordant cases, i.e., where the neural network fails to predict actual outcome. For instance, in a patient with failed ablation therapy whose profile includes atrial scar on MRI, the invention will be trained to link the locations of scar, with locations of ablation lesions, with outcome. One potential output from the trained network is that ablation that misses regions of scar may produce poor outcome. Domain knowledge (physiological interpretation) is used to provide plausibility for any trained network, to ensure mathematically that implausible (or impossible) links are not constructed, and hence revise the network. This combined mechanistic/machine learning approach is a novel strength of the invention that is often omitted from machine learning systems that do not check data representations against known domain knowledge. Errors to be avoided include adversarial examples; in image recognition, applications in which changing one pixel can alter the classification from "cat" to "dog". The present invention prevents such trained networks from being developed in this medical space where errors must be minimized.

Accordingly, the inventive approach directed to developing, testing and revising increasingly interpretable data structures. Models will combine statistical analyses with expert interpretation of case failures/successes. Simple statistical tests and linear models may help to identify correlations between different variables in a system but may not be able to capture underlying complexity and nonlinearity of these studied complex clinical problems. Decision trees such as CART may allow greater interpretability of the importance of each extracted feature from layers of the network. Inputs to decision trees will be extracted features from the images and time series signals.

Another approach in this invention is termed "network clamping." In step 715, from a trained baseline "health" version of the network, inputs are deranged singly or in batches and the network 712 is rerun to identify which abnormal input combination causes the network to most closely recapitulate the "disease state."

These steps are evaluated in steps 718 to identify the constellation of data elements that contribute to deciding on the presence or progression of a specific disease or facet of health, i.e., most relevant to this process in step 721. This "disease-specific PDP" is used for each specific embodiment and is updated in the personal database 724.

Figure 7:
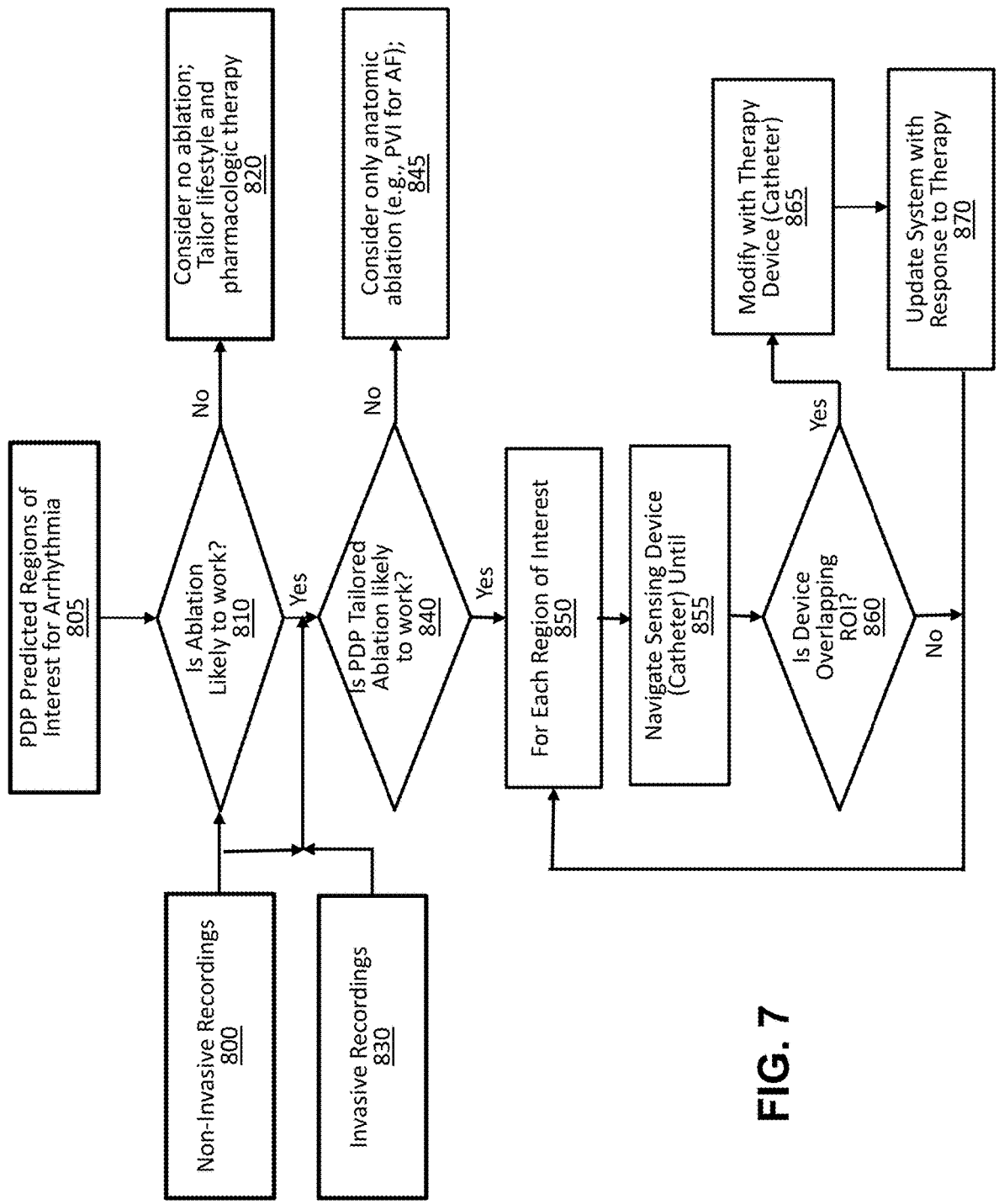
FIG. 7 is a flow chart to manage complex arrhythmias based on PDPs, in accordance with one or more embodiments.

FIG. 7 illustrates an exemplary workflow for using PDP to manage and treat atrial fibrillation. Steps 800, 810 and 820 make up the first triage level, which personalizes for a specific patient. Steps 830-870 personalize AF mapping, map interpretation and ablation.

Step 800 inputs non-invasive signals for AF. These may comprise ECG data from the standard 12-lead ECG, body surface potential mapping (also known as ECG imaging, ECGI) which may use up to 200 body surface leads, magnetocardiography (MCG) non-invasive structural imaging and other features that can be obtained prior to invasive study. Step 810 compares these non-invasive data to elements of the PDP pertinent to this arrhythmia in this individual, i.e. the 'arrhythmia PDP' step 805 determined as outlined in FIG. 6. Step 820 outputs the decision from this analysis.

Step 800 provides an option for disease prediction, in which the inventive technique identifies phenotypes who do not manifest AF but who may be at risk due to specific patterns of structural abnormality marked by low voltage or potentially abnormal on delayed enhanced magnetic resonance imaging. In this case, the invention provides for AF prediction. Ideal input data in this case may comprise granular imaging data showing MRI abnormalities, or granular data on regions of low voltage to enable non-invasive detection of structural risk profiles by the network to provide prognosis, or potentially targets for therapy. Treatment may include ablation to connect these regions of scar or fibrosis.

Outputs of step 820 are determined quantitatively in an individual by the non-invasive data from step 800, the disease-specific PDP (here, for arrhythmia) and the digital taxonomy. For the specific embodiment of AF therapy, outputs comprise lifestyle changes, drug therapy and ablation. The inventive system quantitatively assigns scores to each output using steps outlined above in the sequences shown in FIGS. 4, 5. The lifestyle change output is assigned a higher score in a patient with remediable factors such as high body mass index, poorly treated diabetes, sedentary lifestyle and excessive alcohol consumption, etc. The output of pharmacological therapy will be assigned a higher score in a patient of older age, without heart failure and with prior failed AF ablations. These features are based on epidemiological data, of which several other features are known to those skilled in the art, tailored by the PDP and digital taxonomy for AF. For example, if non-invasive data show critical AF regions near the pulmonary veins or in other regions amenable to ablation, then ablation is assigned a higher score. If the PDP suggests a good candidate (low BMI, paroxysmal AF, no prior ablation) yet non-invasive data show no critical regions near PVs or in other regions amenable to ablation from the digital taxonomy, then ablation is assigned a lower score.

If step 810 identifies that ablation is likely to work, invasive recordings in step 830 are engaged. Here the first step is to acquire data from inside the heart, which is typically performed during AF using invasive catheters, such as the catheters described below. Alternatively, non-invasive data 800 could also be used to provide these data. Step 840 determines what type of ablation is likely to work. If PDP-tailored ablation to specific source regions of interest is not assigned a high score, in step 845 the invention increases the score for considering anatomic ablation alone. This would include pulmonary vein isolation, and, rarely, other anatomical targets including posterior left atrial wall isolation, or in specific patients mitral, roof, intercaval or other lines tailored by the PDP.

If PDP-tailored ablation is determined in step 840 to have probability for success above a pre-determined threshold, steps 850-870 are followed to guide and deliver therapy.

Step 850 considers each region of interest in turn. The PDP-based analysis of electrical signals focuses on identifying regions of interest that may be drivers with rotational or focal activity, regions of low voltage suggesting scar, or other regions of interest. The size of these regions is also identified from intracardiac (with or without non-invasive) recordings to tailor the size of the mapping tool and therapy tool appropriately.

In some embodiments, the regions are identified one after the other from a small mapping catheter that provides high resolution recordings. In step 855, the signals from the sensing tool (AF mapping catheter) are analyzed to determine a direction in which to move towards a target region of interest (for instance, towards a source).

Step 860 determines if the AF mapping catheter is overlying a critical region of interest. The catheter size is important to assess proper positioning and is selected using the PDP to tailor the procedure to the expected size(s) for the patient. If the mapping catheter does not overlie the critical region, the process is followed to guide navigation.

In step 865, if the mapping tool overlays a critical region, this region is now targeted for therapy. In some embodiments, the mapping catheter also includes the ability to deliver ablation energy so that this is done seamlessly. In other embodiments, a separate ablation tool will need to be deployed.

Step 870 assesses the response to therapy, particularly if the region of interest has been eliminated. If not, therapy is repeated.

The process returns to step 850, navigating to and ablating regions of interest until they are all eliminated. The total number of regions treated is determined in real-time by the electrical signals obtained from steps 800 and/or, 830 along with the expected number of regions based on the PDP.

In another embodiment, all regions of interest are identified simultaneously using global mapping from a basket catheter or inverse solution methods, and navigation is applied only to the treatment tool rather than the wide-area mapping catheter.

Figure 8:
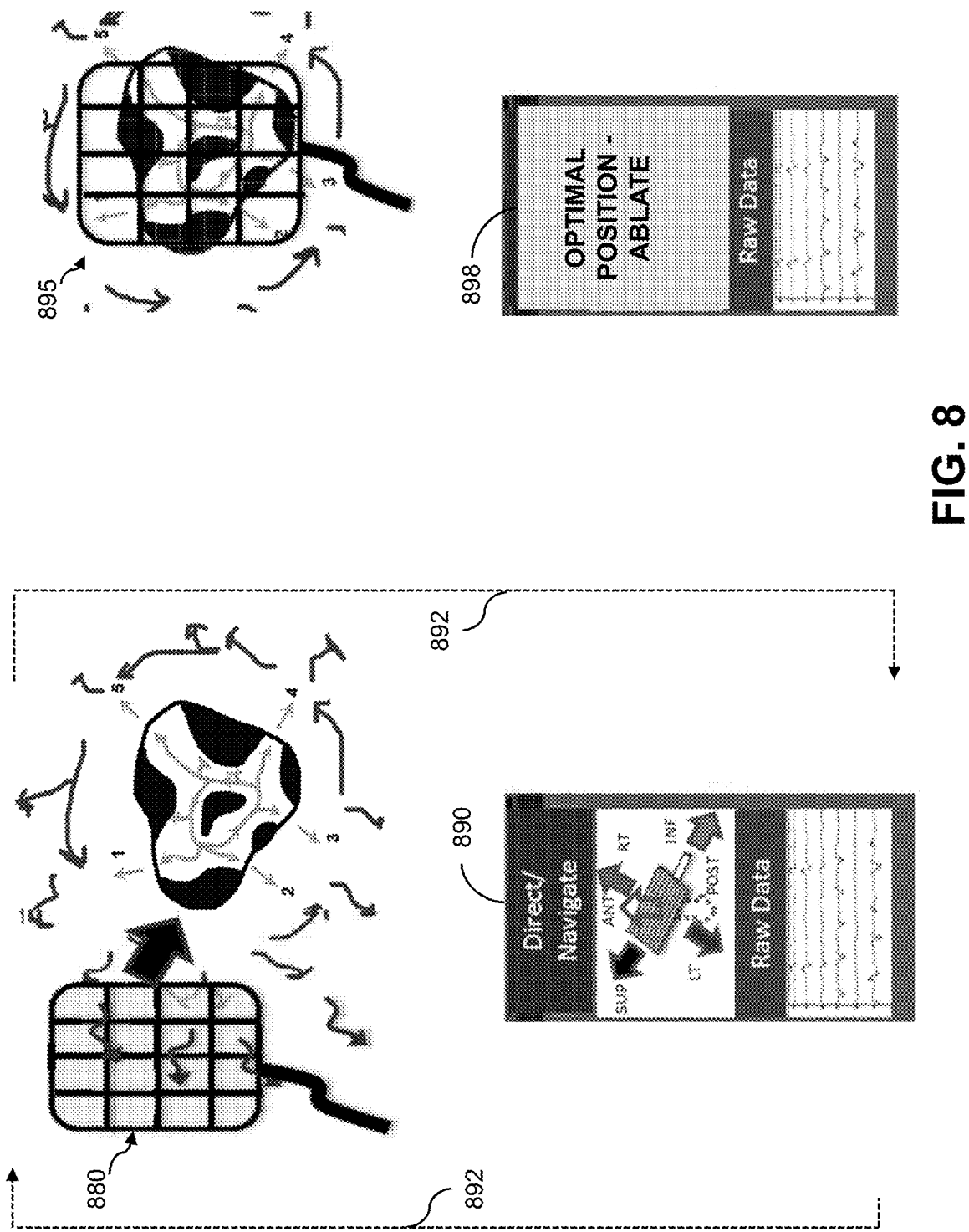
FIG. 8 illustrates an embodiment of the system to map heart arrhythmias, with a display unit of sensed signals, indicating directional guidance for the sensor to move towards a source region of interest, and to indicate when this region has been reached, in accordance with one or more embodiments.

FIG. 8 summarizes personalized therapy for an embodiment of ablation therapy. On the left side of the figure, sensing tool (mapping catheter) 880 is shown some distance from a region of interest. The system analyzes the electrical waves to determine if the mapping catheter overlays the region of interest, and in this case determines that it does not. The system then provides navigation information to direct the catheter towards the closest region of interest. This can be displayed on a portable display 890, such as a repurposed smartphone or a smartphone app, or on a dedicated medical display unit. Each of the display units will include appropriate data security and privacy safeguards in place. The navigation process is iterated, indicated by arrows 892. On the right side of the figure, the mapping tool 895 is shown to overlay the region of interest. This is termed the "treatment position". Display 898 now indicates "Optimal position, ablate". Ablation can now be performed if the mapping catheter includes an ablation tool. If not, a separate ablation catheter can be inserted. The process is repeated until the operator determines that sufficient regions of interest have been treated. The number of regions to be treated will be determined by the PDP for patients of this type relative to the location and size of regions.

Figure 9:
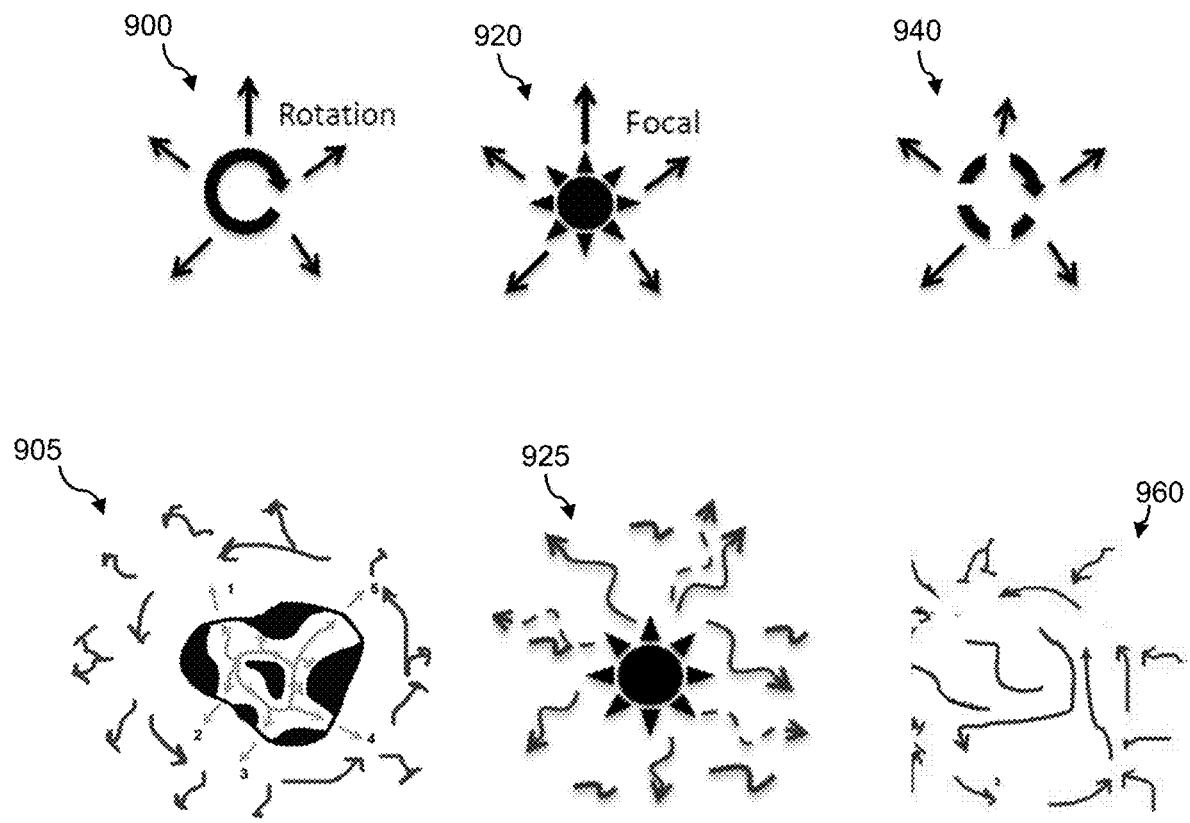
FIG. 9 shows sample regions of interest (ROI) which may be targets for therapy for rhythm disorders.

FIG. 9 diagrammatically illustrates several types of regions of interest (ROI) for heart rhythm disorders that can be identified and classified by the invention. These patterns cover the majority of electrical rhythms. ROI 900 indicates rotational activation without fibrillation, which may be seen in micro-reentry from a focal site. ROI 905 corresponds to rotational activation within fibrillation, which may be seen during atrial fibrillation or ventricular fibrillation. It can be detected using the procedures described herein for directionality analysis. ROI 920 represents focal activation without fibrillation and may be seen in focal tachycardia or extra beats from the atrium or ventricle. Focal activation in the midst of fibrillation (ROI 925) may be seen during atrial fibrillation or ventricular fibrillation and can be detected using directionality analysis. Some activation patterns may not show classical electrical rotations (rotors) or focal sources. In this case, atypical patterns (ROI 940) may still be targets for therapy, such as partial rotations or repetitive activations which may be found in patients with specific comorbidities, e.g., with advanced disease, near sites of low voltage or abnormalities on delayed enhancement magnetic resonance imaging. Such target patterns may be identified as low voltage zones, or viable channels of tissue within regions of low or borderline voltage. When such patterns are found, the inventive system will suggest navigation towards this detected target type. Note that ROIs 900, 920 and 940 cover small regions of tissue and can be covered by a small mapping tool, while ROIs 905 and 925 cover larger regions of tissue (in fibrillation) and may require larger sensing tools. ROI 960 represents disordered activity with no clear pattern. If ROI 960 is identified, no specific navigational guidance is provided and the system recommends systematic mapping until another region of interest can be detected.

Figure 10:
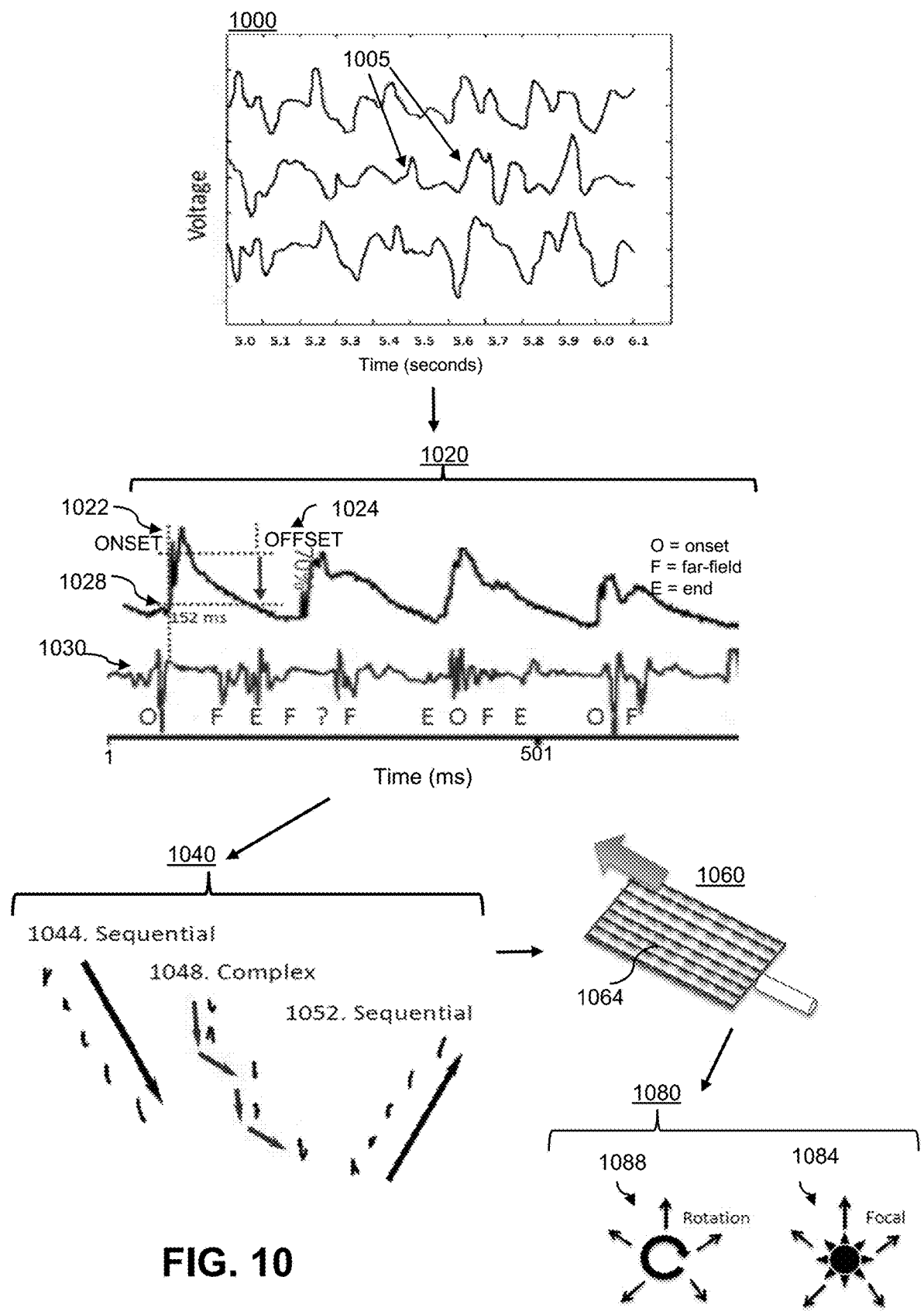
FIG. 10 provides an overview of directional guidance in the invention towards a target region of interest for rhythm disorders using sensed data in that individual, in accordance with one or more embodiments.

FIG. 10 provides an overview of an exemplary directionality analysis sequence. In step 1000, complex electrograms (unipolar signals) in AF are obtained. Note that the onsets and offsets 1005 of signals in complex arrhythmias are often unclear and components may include activation, recovery (repolarization), noise or other features. The inventive approach uses numerical methods calibrated to monophasic action potentials (MAPs) in step 1020. MAPs provide one of the few methods to identify actual activation time (onset) and recovery time (offset) in complex rhythms in the human heart. Phase 0 (1022) of the MAP indicates onset time, and phase 3 (1024) of the MAP indicates the offset time during any electrical rhythm in the tissue. MAP onsets of successive beats are typically separated by a duration of 100 ms to 250 ms in atrial fibrillation or ventricular fibrillation, and 200-500 ms for atrial tachycardia, atrial flutter or ventricular tachycardia. Conversely, traditional electrical signals 1030 in a complex rhythm disorder often include multiple deflections from which it can be difficult to discern activation onsets (depolarization) or offsets (repolarization). Such signals are traditionally analyzed using features such as a sharp inflection point or high slope of depolarization. However, signal 1030 shows that such rules often incorrectly label deflections of unclear significance as activation onset. The inventive approach employs analytical techniques such as machine learning to identify activation onset and offset times from electrograms, calibrated to the ground-truth annotated in MAP recordings, indicated as line 1028. The analytical tool employed in the inventive method is thus able to distinguish onsets ("O"), offsets (also referred to as ends, "E") and other far-field noise components ("F") from traditional noisy electrograms, e.g., signal 1030, when MAPs are no longer present.

For any given array of electrodes, the trained system can accurately identify activation onset and offset, making it possible to accurately map activation paths in step 1040, even in the case of complex rhythms. The array of electrodes measures electrical signals from electrodes over the array. These electrogram comprise many features including noise. The machine learning model is applied to each electrogram to identify the onset and offset times for each cycle (or beat), and far-field noise. Analysis results in a sequence of accurate activation (onset and offset) times at each electrode. These activation times can be described as an activation front defined by:

$$\Phi(x, y, t^*) = \begin{cases} 1, & \text{if } t^* \in \tau_{xy} \\ 0, & \text{otherwise} \end{cases}$$

in which the activation front Φ is assigned '1' if there is an activation time event at that point (x,y) at rescaled time t*, and is otherwise assigned '0'. Streamlines are used to track the flow of activation fronts in time, using spatial gradients over the entire electrode array to infer directions of subsequent motion. Within step 1040, different paths may be generated, including for example, sequential activation paths 1044 and 1052, which travel in opposite directions, and complex path 1048, which is not sequential.

Analysis of propagation flow in step 1060 provides information on directionality. The direction of electrical flow in the rhythm can be calculated across a multi-sensor array tool 1064. Retracing the direction of the electrical flow provides a path towards the source of the rhythm disorder, if detected, or other electrical target. In step 1080, the type of source is determined, for example, focal sources 1084 and rotating sources 1088, to identify the location from which activation emanates outwards, even during complex fibrillatory rhythms, and the direction in which the path would lead. Obtaining this result does not require global mapping of the entire chamber, which is often not possible and even when possible provides low resolution mapping. The inventive approach of mapping flow of conduction over time can be applied to complex rhythms such as fibrillation, which can be difficult to interpret by standard vector analysis due to the fact that waves tend to change rapidly in space and time.

Figure 11A:
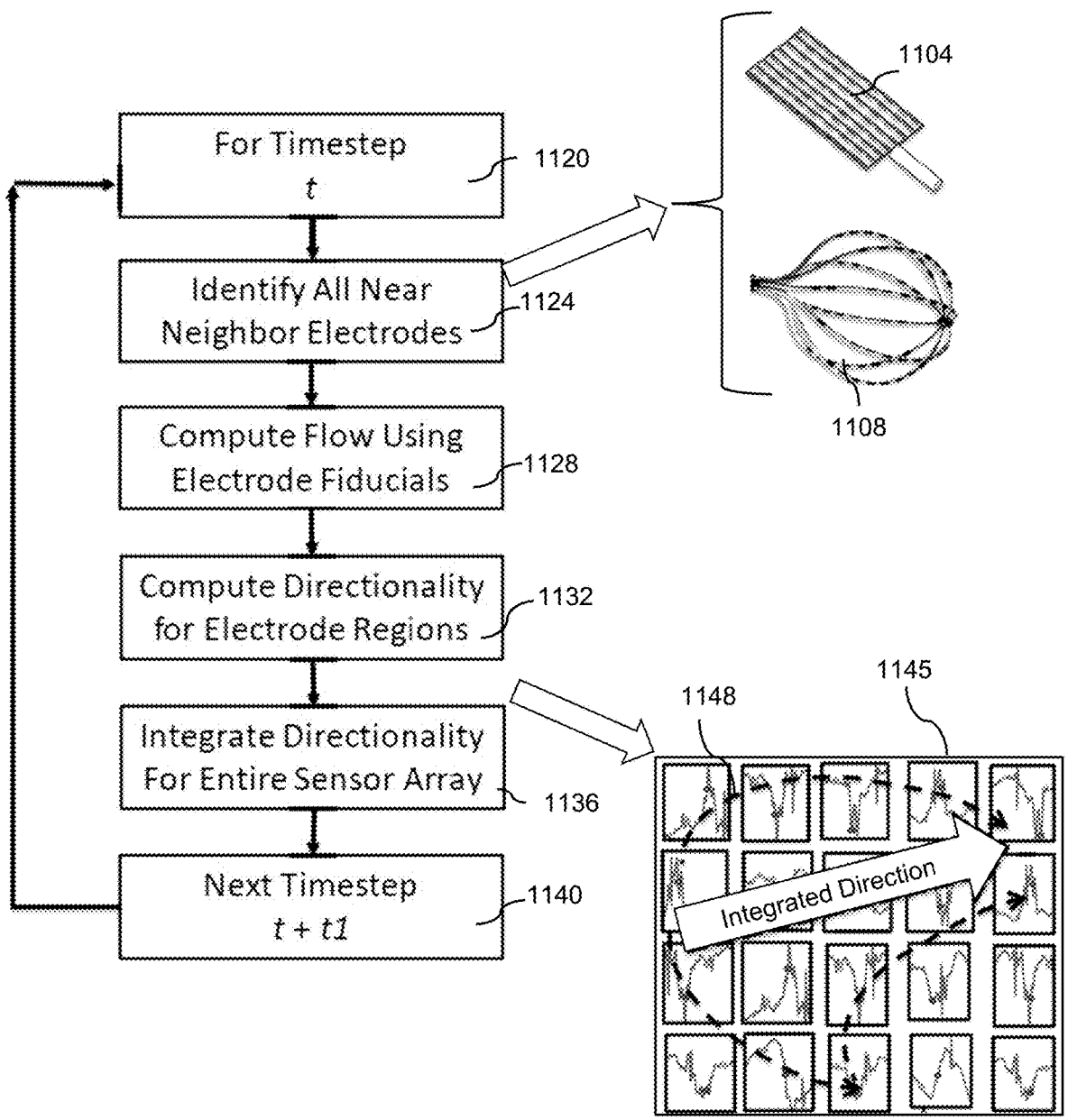
FIG. 11A is a flow diagram showing steps for directionality analysis in accordance with one or more embodiments.

FIG. 11A illustrates the steps within a sequence for directional guidance. The algorithm flow starts at timestep 1120, beginning at 1. Neighboring electrodes are identified in step 1124 as physically adjacent, with known electrode spacings. Sensing devices with neighboring electrodes can take many forms. A few examples shown in the figure include a multipole device 1104—a high resolution multipolar spade catheter, and a basket device 1108—a multipolar basket catheter. Other multi-electrode devices are known; selection of appropriate sensors with known electrode spacings will be apparent to those in the art. In step 1128, flow is computed using electrode signals integrated over the timestep/(shown previously in FIG. 10). First, the system spatially interpolates the wavefront Φ by electrodes at known spacing on the array. For each point i along this interpolated wavefront Φ at time 1, the system searches within a circle for the point j at the next time step with the most similar gradient. The system infers that the activation wavefront has traveled from point i to point j in this time and marks this flow with an instantaneous flow vector (propagation over time). Step 1132 repeats computation of flow (directionality) across regions of the electrode array to generate multiple electrograms over windows of 150 ms to create a collection of electrograms. As an illustrative example, array 1145 is shown, with the window arranged in a pattern corresponding to the positions of the electrodes in a multi-electrode catheter. Directionality is integrated in step 1136 over the entire available number of electrodes on the array to determine the average direction of electrical flow, indicated by the large arrow labeled "Integrated Direction". The dashed lines 1148 indicate flows used to determine the average direction, which is capable of describing complex spatiotemporally changing fibrillation. Guiding the sensor in reverse from the average direction will move closer to the nearest source region or other target region. This approach improves upon the accuracy that can be obtained when using a single electrode, which historically has not been able to find critical regions of interest for fibrillation. The timestep is incremented (+t₁) in step 1140 and the process is repeated for one or more later timesteps for either a predetermined number of timesteps or continuously until terminated by the user.

Figure 11B:
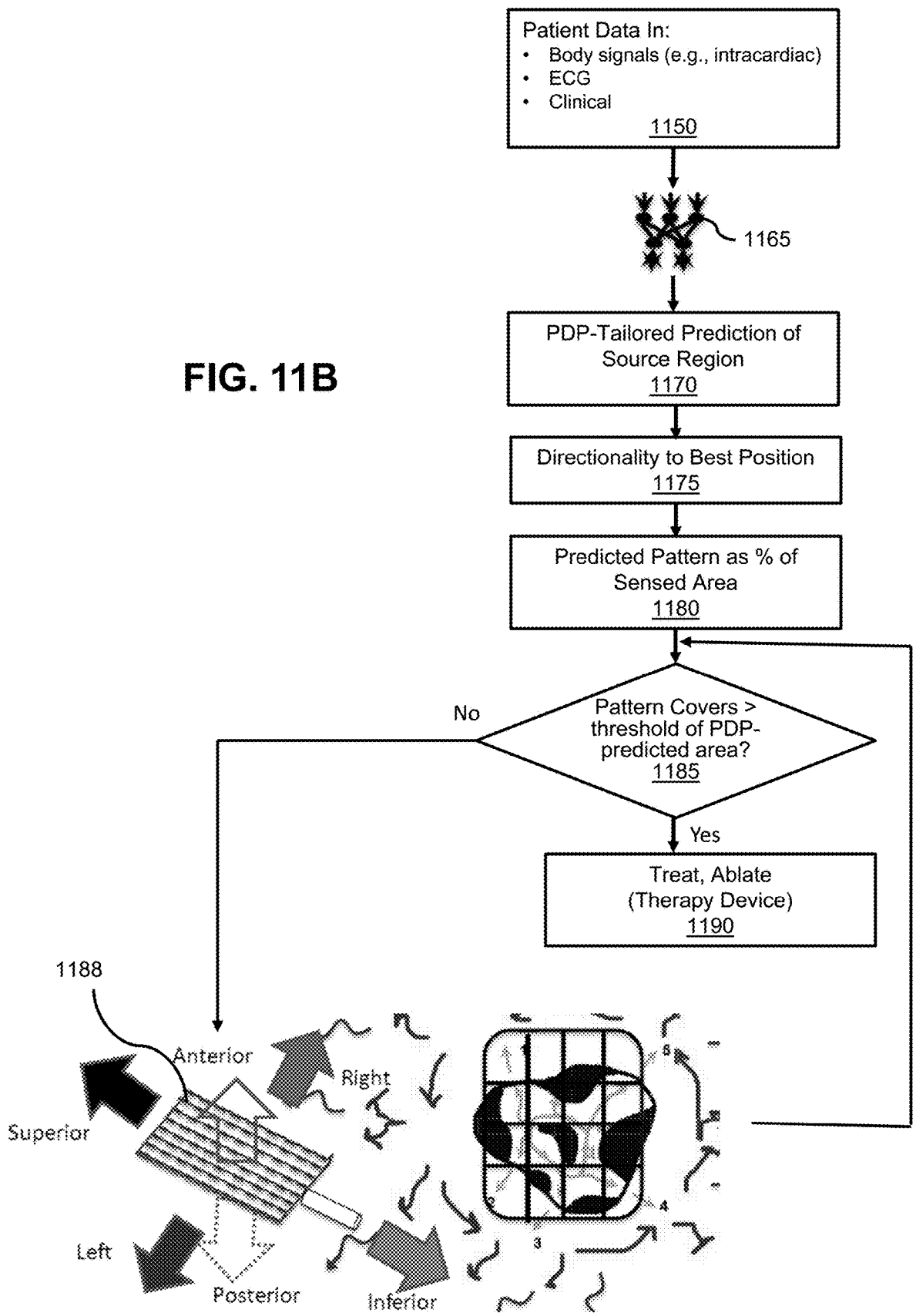
FIG. 11B is a flow diagram showing steps for directionality analysis and treatment in accordance with one or more embodiments.

FIG. 11B provides an overview of the process flow for identification of possible arrhythmias. In step 1150, patient data including body signals, e.g., intracardiac signals, are integrated with ECG data and clinical variables such as age, gender. In step 1165, multiple mathematical approaches can be used to integrate the patient data signals, including correlation coefficients from multivariate regression or supervised machine learning models such as convolutional neural networks (CNN) or support vector machines (SVM) trained to a specific output label of AF termination or long-term outcome during algorithmic development. In step 1170, the integrated signals are input into the PDP-based arrhythmia predictions to estimate a source region. In step 1175, directionality analysis is used to guide the ablation catheter to the target region of interest, for example, a source for the arrhythmia. The ablation catheter is then analyzed to determine a ratio (percentage) of the number of electrodes that are covered by the region of interest in step 1180. This is achieved by determining the area of the sensor that covers the predicted region of interest. In step 1185, a determination is made as to whether the area ratio exceeds a predicted ratio. If so, the therapy is applied at this site in step 1190. If not, in step 1188, the catheter is guided toward a direction, e.g., right, left, anterior, etc. using the available controls, to move the catheter toward a position until it meet or exceed the predicted ratio in step 1185.

Candidates for AF ablation targets include mathematical combinations of electrogram features plus comorbidities (e.g., body mass index, diabetes, hypertension), demographics (e.g., age, gender, prior ablation or not) and, if available, genetic, metabolic and biomarker information. Novel electrogram targets analyze beyond 'traditional' targets. For instance, studies have suggested that targets such as repetitive patterns, or transient rotations or focal patterns, or interrupted rotational or focal patterns, may be critical to maintaining arrhythmia in some individuals. This embodiment of the invention defines these electrogram features, by determining in individual patients which may be related to favorable outcomes. This then becomes a numerical classification within the digital taxonomy as data from more individuals is labeled and accumulated.

Depending on the patient, therapy targets may be rotational or focal sources/drivers, or other electrical target—regardless of structure. Intermediate phenotypes may be present in phenotypes in specific individuals (electrical and structural, which may dynamically change with e.g., changes in health status). Again, multiple forms of electrical pattern may colocalize with such structural elements, and the invention will store electrical signals associated with these sites to update the personal and population databases. Therapy may include destruction of tissue by surgical or minimally invasive ablation, to modulate via electrical pacing or mechanical pacing, or using gene, stem cell, or drug therapy. Medications may include class I agents to decrease atrial conduction velocity, or class III agents to prolong refractoriness. AF ablation may not just eliminate tissue, but target areas bordering fibrosis or areas of electrical vulnerability. Therapy can also be directed to related tissue to these regions, their nerve supply, or other modulating biological systems.

Figure 12:
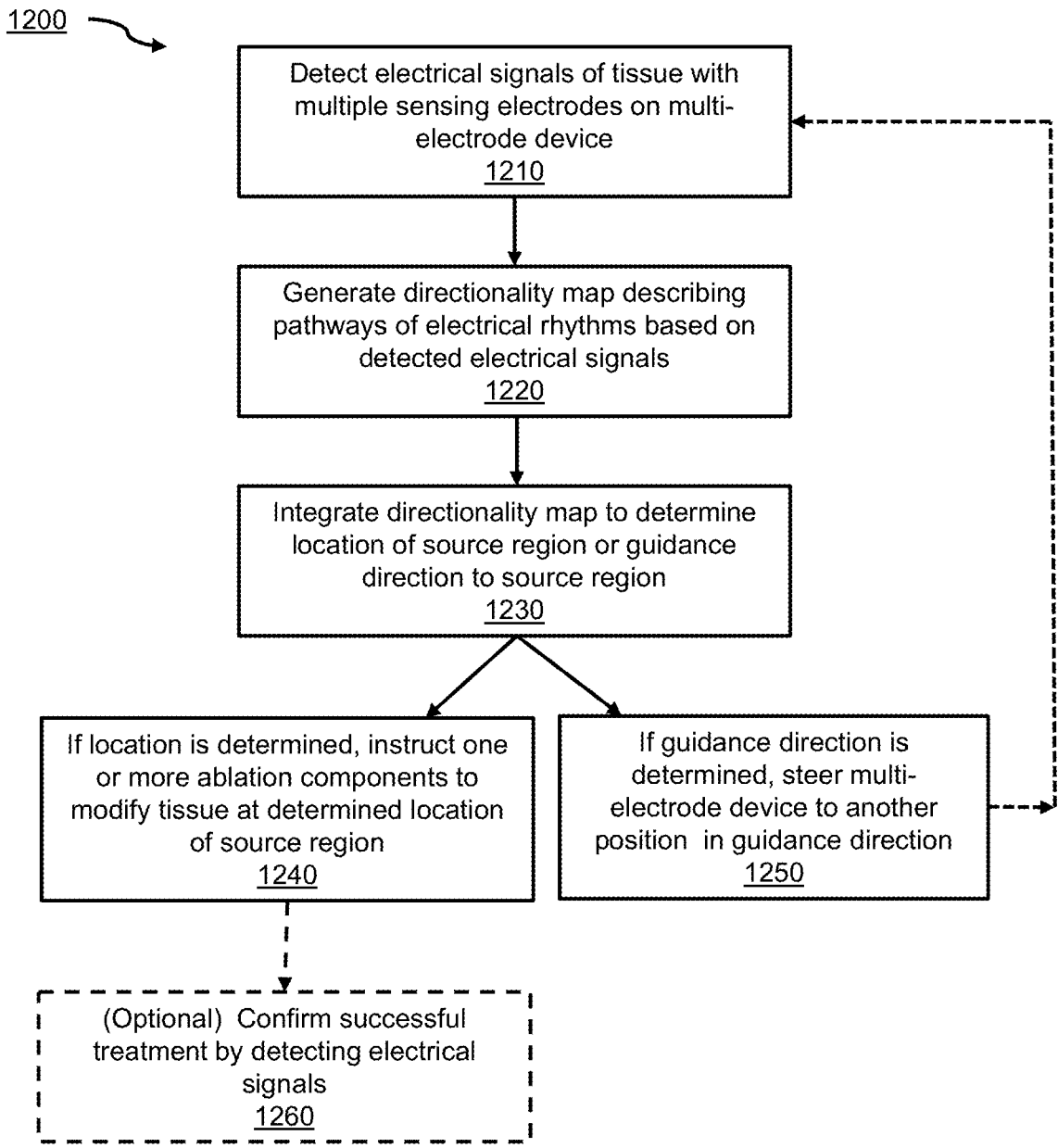
FIG. 12 is a flowchart illustrating a process of treating an electrical rhythm disorder in accordance with one or more embodiments.

FIG. 12 is a flowchart illustrating a process 1200 of treating an electrical rhythm disorder in accordance with one or more embodiments. The process 1200 is performed using a device for sensing and treating electrical rhythm disorders. In some embodiments, the device is an ablation catheter such as those described below with reference to FIGS. 13-19, a basket catheter, e.g., basket catheter 1108 in FIG. 11A, or other multi-electrode catheter. The ablation catheter is configured to perform both sensing of electrical signals of a tissue and treatment of electrical rhythm disorders with ablation energy. The ablation catheter may provide ablation energy in one or multiple forms, e.g., electromagnetic energy, freezing energy, etc.

In step 1210, the device detects a plurality of signals of a tissue using a plurality of sensing electrodes on an ablation catheter. In step 1220, the detected electrical signals from the electrodes are used to generate a directionality map that describes pathways of electrical rhythms. The directionality map may be generated by inputting the detected electrical signals into a trained machine learning model. In some embodiments, a supervised training approach is used in which the learning machine will have been trained on training examples comprising electrical signals of a human heart and known locations of one or more source or other target regions of a heart rhythm disorder.

In step 1230, the directionality map is integrated to determine one of: (a) a location of a source or other target region of the heart rhythm disorder in the directionality map, and (b) a guidance direction to the source or other target region of the heart rhythm disorder that lies outside of the directionality map.

If the model was successful in determining the location of the source or other target region, i.e., the directionality map is substantially aligned with the target, in step 1240, one or more ablation components on the catheter is activated to modify tissue at the determined target location. The number of ablation components to be activated may be based on a threshold proximity to the location of the source region for use to deliver the ablation energy. The directionality map may be used to determine a size of the target region to be ablated and to select the appropriate combination of ablation components to be used to modify the determined size of the target. In some embodiments, the ablation electrodes may be configured to generate electromagnetic waves that modify tissue at the target. The ablation energy applied to the electrodes can be modulated to generate a distinct waveform. Selection of a particular ablation waveform along with other ablation signal characteristics will generally be within the level of skill in the art of the medical practitioner. Selection may be assisted by look-up tables or guided by knowledge gained through the use of a machine learning model trained on data obtained from population data. The device may further vent irrigant from one or more irrigation pores on the device onto the tissue to prevent overheating of surrounding tissue or other portions of tissue not intended to be modified.

Irrigation of the electrode grid may be adjusted according to the number of electrodes, their size and inter-electrode spacing and anticipated power delivery and heat generated during use. The primary goal of the irrigant is to cool tissue and limit heat rise during energy delivery. Cooling allows increased power delivery without approaching temperature levels that could vaporize tissue or blood with gas formation, or form char or clot. Irrigant also directly flushes small clots or clumps of char before they can aggregate. Irrigation thus improves safety by reducing the likelihood of these problems. Appropriate irrigants may include saline that has similar osmolarity to plasma (i.e., "normal saline"), half of that osmolarity ("half-normal"), higher than that osmolarity ("supernormal"). Alternatives include dextrose (glucose) solutions or other electrolyte solutions familiar to those skilled in the art. The flow rate of irrigant is typically in the range of 2-50 ml/min over the catheter during ablation. Increasing the rate will increase cooling and enable greater power delivery, while reducing flow will lead to greater heating. A typical flow rate range for the inventive devices and methods is 5-10 ml/min for the atrium of the heart, and 15-30 ml/min for treating the ventricle of the heart.

In still other embodiments, the ablation components may be a plurality of cryoablation chambers configured to fill with an appropriate coolant. When the outer surface of a coolant-filled chamber is brought into contact with tissue, it can rapidly cool the target regions for the heart rhythm disorder. Coolants that can be used in the cryoablation embodiments include nitrous oxide ($N_2O$), with a boiling point of $-89°$ C., carbon dioxide ($CO_2$), with a boiling point of $-79°$ C., and liquid nitrogen ($N_2$), with a boiling point of −188° C. Other refrigerants that may be used will be apparent to those of skill in the art. Cardiac and nerve tissue typically die at about −100° C., and so lower temperatures may ensure more complete tissue ablation. The drawbacks of very low temperatures, such as liquid nitrogen, are the technical difficulties of keeping the irrigant refrigerated, and risks of unintended damage to surrounding regions, including structures adjacent to the heart.

In step 1230, if the process has not determined the actual target location but has determined a guidance direction to the target outside of the directionality map, in step 1250 the catheter is steered toward a subsequent position along the guidance direction. Once the catheter has been moved to the next position, step 1210 is repeated to detect subsequent electrical signals of the tissue with the plurality of sensing electrodes. Steps 1220 and 1230 are repeated to successively determine the guidance direction. If the location is not yet determined in step 1230, with the catheter continues to be steered incrementally towards the source or other target region in step 1250 until an indication is provided that the target has been located. In some embodiments, the catheter positioning will be controlled by a physician, in which case the system may provide some form of notification, e.g., a visual display on a display device, an audible tone, or a combination thereof, to indicate to the physician where to move the catheter to follow the guidance direction toward the target.

The inventive system may be used to confirm whether the electrical rhythm disorder has been successfully treated. Successful treatment entails correction of the electrical rhythms and elimination of target regions that would affect the electrical rhythms. In optional step 1260, the system may be used to detect electrical signals within the treated area using the plurality of sensing electrodes after ablation of the source or target region. Upon confirmation of success, the procedure may be terminated by the physician, or automatically by the system based on confirmation that there are no further indicators of the heart rhythm disorder. The system may be used to determine whether the heart rhythm disorder persists based on the subsequent electrical signals. If the disorder persists, steps 1210-1250 can be repeated to locate a second source or target region that may be contributing to the persistent disorder. In some cases, if ablation was not successful in treating the target, the disorder may be determined to persist based on subsequently captured electrical signals. The system can be used to apply additional ablation energy to the same region to ensure successful treatment.

Figure 13:
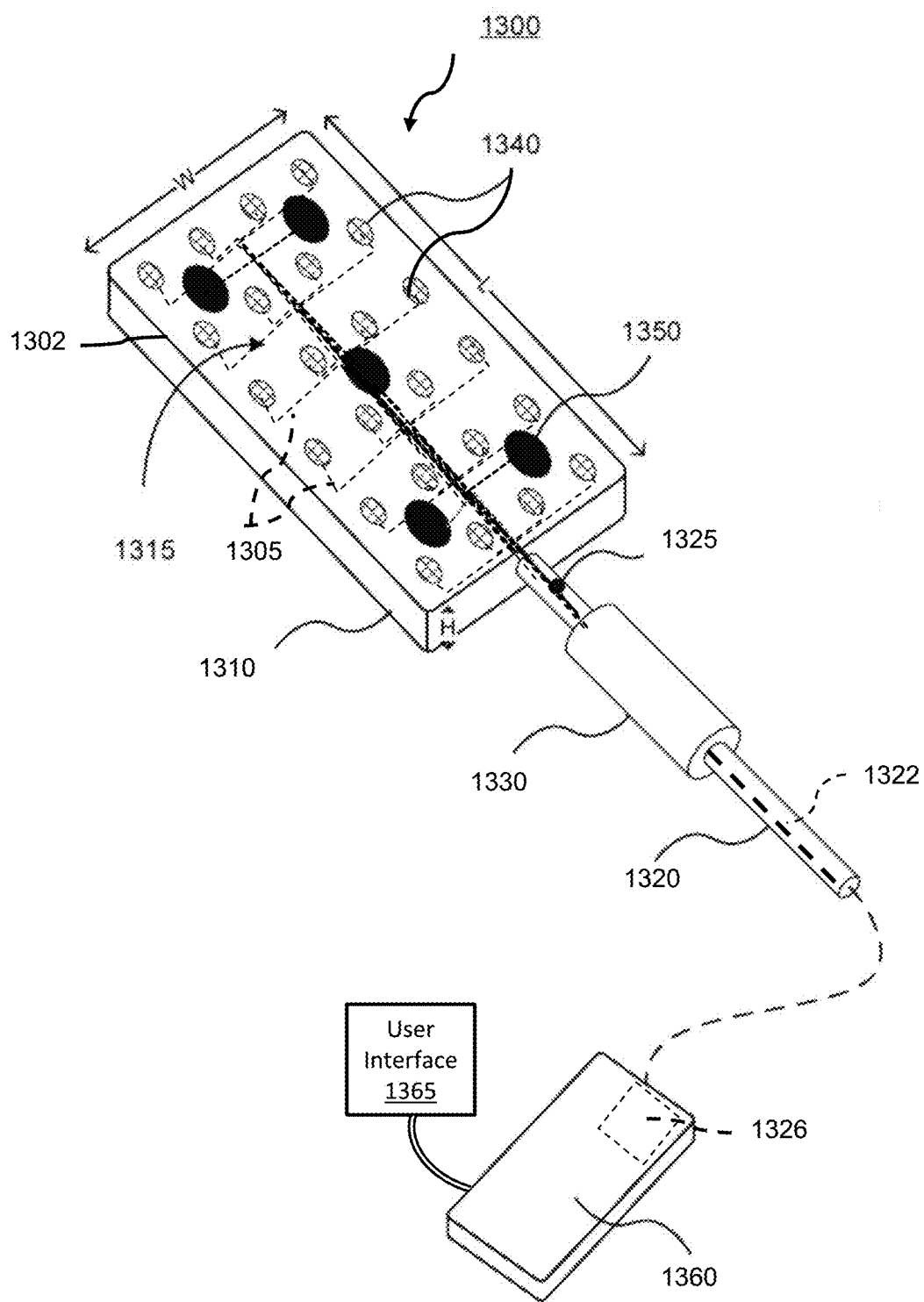
FIG. 13 illustrates an exemplary ablation catheter for treating electrical rhythm disorders in accordance with one or more embodiments.

FIG. 13 illustrates an embodiment of an ablation catheter 1300 for treating electrical rhythm disorders. Ablation catheter 1300 combines sensing functionality and therapy delivery functionality in one tool which includes a spade 1310, shaft 1320, and controller 1360. Spade 1310 includes a thin flexible body 1302 that supports an array of sensing electrodes 1340 for guiding the ablation catheter 1300 to one or more source or other target regions. In most embodiments, body 1302 also supports one or more ablation components 1350 configured for delivery of a tissue-modifying energy (e.g., electromagnetic or thermal), as will be described in further detail below with reference to FIG. 13-. Body 1302 is generally planar in its relaxed (non-deployed) condition, formed of a resilient material that is sufficiently flexible to collapse and fold the body into a retention volume as well as conform the catheter's contact surface to the adjacent tissue surface once deployed. Spade 1310 may further include components such as one or more irrigation pores for directing irrigant to the surrounding tissue or imaging. The proximal end of spade 1310 is coupled to shaft 1320, which is steerable by controller 1360. Shaft 1320 houses wiring to the various electrodes on the spade 1310 along with channels for supplying fluids to the spade 1310, e.g., coolant, irrigant, etc. Shaft 1320 extends concentrically through a sheath 1330 that has an inner volume configured to retain spade 1310 when folded. Shaft 1320 may also include one or more contact sensors 1325 for sensing whether the spade 1310 is in contact with tissue. The controller 1360 is coupled to the proximal end of shaft 1320. The spade 1310 may attach to shaft 1320 at any point around its perimeter. In other words, it need not be symmetrically aligned with the spade centerline as illustrated but may be offset from the center.

Controller 1360 is configured to receive and analyze electrical signals detected by the sensing electrodes 1340 to determine a location and/or guidance direction to a source or other target region for the arrhythmia. Controller 1360 provides control signals to the shaft 1320 to direct movement of spade 1310 in the guidance direction towards the target region. Controller 1360 provides signals to ablation components 1350 to modify the tissue at the target region. In some embodiments, the functions of the various components of ablation catheter 1300 may be otherwise distributed amongst the components. In additional embodiments, ablation catheter 1300 includes additional or fewer components than those listed herein.

Spade 1310 is positioned to contact tissue to treat electrical rhythm disorders. Typical spade dimensions are 5 mm-50 mm in width (W), 5 mm-50 mm in length (L) and 1 mm-5 mm in thickness (H). In a common embodiment for the heart, dimensions are 25 mm wide, 30 mm long and 2 mm thick. In some embodiments, the spade body 1302 is formed from a thin, flexible polymer such as silicone, polydimethylsiloxane (PDMS), or similar biocompatible polymer to allow the spade to be easily collapsed or folded into the inner volume of sheath 1330. An exemplary fabrication process would involve a liquid polymer being introduced into a mold with the wires 1305, electrodes 1340, 1350 and other components pre-arranged in the mold. The mold and liquid are then exposed to appropriate conditions (e.g., heat, atmosphere, light, etc.) to cure the polymer material to the desired finish and flexibility. While the wires may be pre-formed for layout within the mold, in some embodiments, the wires 1305 may be interconnects formed using a conductive paste or film that is printed or deposited using known patterning techniques, e.g., thick film, thin film, inkjet, or other printing method, into channels in the polymer material to electrically connect to the electrodes. To provide a little more detail, the electrodes and ablation components positioned within the mold, then a first layer of polymer would be added to the mold leaving the connectors on the backs of the components exposed and partially or fully cured. Next, the interconnect would be patterned on top of the first polymer layer. Standard bonding methods can then be used to connect the printed wires to wires that extend the length of shaft 1320 to connect with controller 1360. A second polymer layer would then be formed to complete and seal the spade structure. The material should be sufficiently durable to tolerate multiple transitions between folding and deployed. The polymer material should preferably be appropriate for heating by radiofrequency energy delivery. In other embodiments, spade 1310 may be fabricated from a combination or composite of different materials, or from the same material that has been treated differently to impart different characteristics, for example, varying degrees of flexibility. In some embodiments, the thickness of spade 1310 may vary along its length or at different areas of the spade.

Sensing electrodes 1340 are arranged in an array within body 1302 so that they are flush with or protrude slightly from contact surface 1315. The electrodes in the array may be arranged in any number of patterns. For example, sensing electrodes 1340 may be arranged evenly in a simple rectangular grid as illustrated in FIG. 13, or other arrangements (e.g., distribution and/or density) may be used. The number of sensing electrodes 1340 may range from 4 to 256 electrodes.

The size and spacing of the sensing electrodes determine the catheter's resolution. The electrode sizes may range from 0.1 mm to 4.0 mm, with selection of electrode size depending on the application. For example, small sized sensing electrodes that are spaced closely would achieve a high resolution, however, there are tradeoffs with both small and large electrodes. The smallest practical electrode size is able to integrate small regions but may be prone to artifacts (e.g., movement artifacts), while the largest electrode size is able to integrate over wider regions but may lose small amplitude signals. For complex rhythms such as atrial fibrillation, a typical sensing electrode may range in size from 0.5 to 1.0 mm to provide good signal fidelity and detect complex signal types that may be targets for therapy. For ventricular tachycardia, a typical sensing electrode may range in size from 1 to 2 mm. For simple rhythms such as accessory pathway mediated tachycardia, a typical electrode size range may be 0.5 to 1 mm to discern accessory pathway potentials. Selection of appropriate sensing electrode sizes will be within the level of skill in the art. In some embodiments, a spade may include a number of differently sized sensing electrodes arranged in groups or at specific locations on the spade. The sensing electrodes 1340 may also be in a variety of different shapes, e.g., oval, round, square, rectangular, etc.

Spacing between sensing electrodes 1340 (measured from the edge to edge) can vary in the range of 0.5-5.0 mm. For atrial fibrillation, a typical sensing electrode spacing will be 1 to 2 mm. For ventricular tachycardia, a typical electrode spacing will be 2 to 4 mm. When very fine detail must be resolved, a typical sensing electrode spacing will be 0.5 to 0.75 mm. In some embodiments, different spacings can be used for different groupings of electrodes or at different locations on the space body.

In the embodiment shown in FIG. 13, ablation components 1350 are ablation electrodes arranged in an array within spade body 1302 so that they are flush with or protrude slightly from contact surface 1315. The number of ablation electrodes 1350 may be on the order of 4 to 36 but will depend on the size of the spade. The size of each ablation electrode ranges from 0.5 to 4.0 mm. For complex rhythms such as atrial fibrillation, a typical ablation electrode ranges in size from 0.5 to 2.0 mm. For ventricular tachycardia, a typical ablation electrode ranges in size from 2.0 to 3.0 mm. For simple rhythms such as accessory pathway mediated tachycardia, a typical ablation electrode size range will be 0.5 to 1.0 mm. In some embodiments, a spade may include a number of differently sized ablation electrodes arranged in groups or at specific locations on the spade. The ablation electrodes 1350 may also be different shapes, e.g., oval, round, square, rectangular, etc.

The spacing between ablation electrodes 1350 (measured from the edge to edge) can vary in the range of 0.5-10.0 mm. For atrial fibrillation typical ablation electrode spacing will be 2.0 to 3.0 mm. For ventricular tachycardia, a typical ablation electrode spacing will be 3.0 to 6.0 mm. Typically, the density of ablation electrodes will be lower than the density for sensing electrodes. In some applications, however, the density could be higher for ablation electrodes, depending on the rhythm and chamber in question.

When the ablation catheter 1300 is ready to be positioned in an individual, the spade 1310 will be in its folded configuration, retained within the interior volume of sheath 1330 to facilitate insertion into the individual's body, e.g., via vascular access. Once ablation catheter 1300 has been guided to the appropriate location, spade 1310 will be released from sheath 1330 to begin the process of detection and/or treatment as described above. The flexibility of spade body 1302 allows spade 1310 to substantially conform to the topography of the tissue surface. Optionally, during fabrication, additional fine gauge spring wires may have been placed near the spade perimeter to facilitate unfurling of the spade once released from the sheath. These spring wires are not be so rigid that they stiffen the spade; they merely enhance resilience to the unfolded, i.e., relaxed, configuration. In some embodiments, spade 1310 may further include a thermoelectric resistant material, for example by embedding such a material within the polymer material used to form the body or forming a composite with the body material. Incorporation of electrically-resistive material in the spade body can be beneficial to maintaining high fidelity in the electrical signals detected by the sensing electrodes 1340. Incorporation of thermally conductive material(s) can be useful when modifying the tissue, i.e., electromagnetic ablation, cryoablation, etc., to help diffuse or disperse the energy/liquid to avoid concentrated delivery immediately at the location of the ablation component. It should be noted that while ablation catheter 1300 is described herein as a "spade", it may also be referred to as a paddle, a grid, an array, a matrix, or a mesh.

As noted above, spade 1310 is formed of a thin, flexible, conformable material, so that contact surface 1315 contacts and conforms to the tissue. While the shape of spade 1310 is depicted as rectangular in FIG. 13, this is intended to be illustrative only and other shapes may be used. Potential variations may include cutting or rounding the corners of the spade to make it easier to pull (or push) the flexible material into the sheath volume. A few examples of other shapes are provided in FIG. 14A and discussed in more detail below. Selection of other shapes that may facilitate folding/unfolding or other functions of the catheter will be readily apparent to those of skill in the art. The size of spade 1310 also affects its functionality. For example, a larger spade 1310, though having the advantage of covering a greater surface area, would represent a bulkier volume and, therefore, could be more challenging to deploy and/or extract. A bulkier volume would correspond to an increased cross-sectional surface area of the ablation catheter at maximum width, thus increasing the opening and pathway dimension required for insertion into the individual's body. The spade size can be individualized by the PDP based on the predicted size of regions of interest for the individual with known clinical profile. An exemplary dimensional range for cardiac arrhythmia applications is on the order of 1.5 cm×1.5 cm to 3 cm×3 cm (W×L). The spade thickness should be sufficient to support the array of sensors against the contours of the tissue, while being flexible enough to be collapsed and folded into the sheath. An exemplary thickness range would be on the order of 0.10 mm to 4.0 mm but may vary depending on the components and features incorporated into the device. In one embodiment, a range of 0.75 mm to 1.0 mm will be sufficiently flexible to conform to the cardiac chamber while providing enough support for the electrode material. In another embodiment, a range of 2-3 mm will provide greater structural stability for use outside the heart, such as for cardiac surgical applications, or for the ventricle, which has a greater range of contractile motion.

Shaft 1320 is an elongated hollow cylinder or tube formed of semi-rigid material with a distal end coupled to spade 1310 and a proximal end coupled to controller 1360. The hollow center of shaft 1320 encloses one or more bundles 1322 of wires that provide electrical connection to the catheter electrodes, steering wires for manipulating the catheter, and, if applicable, liquid tubing, all of which should extend the full length of the shaft to provide communication between spade 1310 and controller 1360. Shaft 1320 is formed and/or coated to provide a low friction biocompatible outer surface to facilitate insertion and removal of the catheter and to reduce risk of damage to the insertion pathway. The interior surface of the hollow catheter may also have a low friction coating to allow free movement of the wire and tubing bundles 1322 within the center of the shaft. Appropriate shafts and shaft materials are known in the art and are widely available commercially. Shaft 1320 is steerable by controller 1360 to manipulate the spade 1310. Shaft 1320 should be of sufficient length to extend from an entry point in the individual to the tissue to be evaluated/treated. For example, for treatment of cardiac arrhythmias, ablation catheter 1300 will be inserted through an opening in the individual's leg or groin and guided through the femoral artery to the heart. Thus, shaft 1320 should be sufficiently long to extend the full length from the entry point to the individual's heart. The shaft's partial rigidity protects the components housed within the center of the shaft and helps to prevent deflections in the shaft that could affect the movement of spade 1310.

A contact sensor 1325 may be located on the distal end of the shaft to allow detection of proper contact of the contact surface of spade 1310 with the tissue surface. In other embodiments, the contact sensor 1325 may be located elsewhere on the ablation catheter 1300, e.g., at some point on contact surface 1315. A number of different of sensor types may be used for contact sensor 1325. For example, contact sensor 1325 can be a sensor configured to measure force applied to the force sensor. Sufficient contact with the tissue surface may be found when the force sensor detects force above a threshold, e.g., 0.25 Pascals. Another type of sensor that may be used is a proximity sensor capable of measuring distance to another surface via capacitive sensing. The change in capacitance is used to calculate the distance between the tissue surface and the capacitor in the proximity sensor. Sufficient contact with the tissue surface may be found if the measured distance is within a threshold distance, e.g., 0.1 millimeters.

Sheath 1330 is a rigid hollow generally cylindrical body configured to retain the spade 1310 in a collapsed or folded configuration. For simplicity, sheath 1330 is illustrated as a standard cylinder with its base at a right angle to the side, however, in practical applications, the sheath body may be beveled, rounded or tapered so that its outer surface is smooth and edge-free, minimizing angular components that might catch on features along the insertion/extraction pathway. For example, an ovoid or partially-ovoid shape might be used. Sheath 1330 is concentrically retained around shaft 1320 and is configured to slide longitudinally along shaft 1320 to pull back from the shaft's distal end to release spade 1310. Specifically, in its initial position, sheath 1330 retains and covers spade 1310 in a folded configuration to allow the catheter to be guided to the tissue. Once the catheter is in place at the tissue, sheath 1330 is moved away from the shaft's distal end to a second position, releasing spade 1310 and allowing it resile into its unfolded configuration. Sheath 1330 may be connected to controller 1360 via one or more wires that guide the sheath between the first position and the second position. In one embodiment, these wires may be activated by a micromotor 1326 within the controller. In some embodiments, sheath 1330 may be displaced using a micromotor built into the shaft and/or sheath that is connected electronically to controller 1360 by wires that extend through the shaft to the controller.

Different organs may have different size recommendations, which may be smaller in the brain or for neural mapping for instance and generally will vary for a given application and/or biological chamber. For example, it may be important for ablation in the heart to encircle a region such as scar, while sensing may be a more uniform grid. As another example, it may be important for ablation in the brain to be denser and focused to allow deep but narrow penetration, while sensing may cover in a broader area. Another constraint on the number of sensing electrodes in a catheter is the size of the bundle 1322 of wires that can be fit into the shaft. In the example illustrated in FIG. 13, 24 sensing electrodes 1340 are arranged in a rectangular grid.

When the sensing electrodes 1340 are in contact with the tissue, they are capable of detecting electrical signals of the tissue. Various types of electrodes may be implemented for the sensing electrodes 1340. Electrodes can be constructed from semiconducting or conductive materials capable of detecting electrical signals from the tissue surface. Sensing electrodes 1340 may be individually addressable by the controller and/or may be arranged in custom patterns tailored to expected characteristics of arrhythmia regions of interest. Multiple electrodes can be formed within one or more continuous sheets of conducting substance, e.g., one or more sensor chips, each with multiple sensors, or discrete sensors can be individually placed within the spade body 1302. Other types of sensors can be included in the catheter, for example, to measure heat (infrared), mechanical motion (piezoelectric or other sensors), chemical composition, or other indices that may have diagnostic value. The circuitry supporting the sensing electrodes 1340 is preferably durable and shock resistant to withstand the energy and pressure that can occur during ablation. The electrical signals may be in the form of an electrogram measuring electric potentials of the tissue. The electrical signals may at least partially pertain to electrical rhythms of the tissue. The placement of the sensing electrodes 1340 is used to create a mapping of electrical signals useful for analyzing a location or a guidance direction to a source or other target region of an electrical rhythm disorder, e.g., according to the principles described with reference to FIGS. 11A & 11B.

Still referring to FIG. 13, one or more ablation components 1350 deliver ablation energy to the tissue or aid in delivery of the ablation energy to the tissue. In one or more embodiments, ablation components 1350 are disposed within contact surface 1315 of spade 1310. As illustrated, one possible arrangement involve five ablation components are arranged with one component at the center and two components each at the distal and proximal sides of the contact surface. This pattern is an example only—other variations, e.g., with different spacings or patterns, and different numbers of elements, may be used to tailor the ablation treatment corresponding to the determined size and/or shape of a source or other target region. Activation of one or more of ablation components 1350 is controlled by controller 1360, allowing each ablation component to be selectively controlled to provide an amount of ablation energy selected from a range of ablation energy.

In some embodiments, ablation components 1350 are ablation electrodes that contact the tissue to deliver electromagnetic energy as the ablation energy. Ablation electrodes typically have larger contact areas than do sensing electrodes 1340 to deliver sufficient electromagnetic energy to the surface. The electromagnetic energy may include radio frequency electromagnetic waves or may include other frequencies of electromagnetic waves. Additional features and variations to the inventive catheters are described below with reference to FIGS. 14A-FIG. 19.

Controller 1360 analyzes the electrical signals received from sensing electrodes 1340 to determine a location or a guidance direction to a source or other target region. Knowledge of the physical position of each sensing electrode 1340 on spade 1310 allows the controller to determine the location of the electrical signals corresponding to each sensing electrode 1340 in relation to the others. Controller 1360 uses the steps shown in FIGS. 11A, 11B and 12 to determine one of a location and a guidance direction to the source or other target region, then generates signals causing shaft 1320 to move spade 1310 toward the target. Upon confirming arrival at the target (e.g., steps 1185, 1230), controller 1360 instructs delivery of ablation energy to the tissue (steps 1190, 1240). Controller 1360 may further interact with other components of the device, i.e., contact sensor 1325, to verify appropriate tissue contact, and if contact is deemed insufficient, may instruct movement of shaft 1320 to properly position spade 1310 for sufficient contact with the tissue. Following the sequences shown in FIGS. 11A, 11B and 12, controller 1360 may continue sensing and treating other detected target regions, if any, until all have been considered for treatment.

In one or more embodiments, ablation catheter 1300 may operate semi-autonomously. In these embodiments, the controller 1360 performs the operations of locating the source or other target region, moving spade 1310 to the target, treating the target region by modifying the tissue with ablation components 1350, and concluding the procedure upon confirmation of successful treatment. In these embodiments, minimal intervention by a physician would be required to operate the ablation catheter 1300.

In other embodiments, the ablation catheter 1300 is operated by a physician. Controller 1360 detects and determines the location and/or the guidance direction to the source or other target region, then generates one or more indicators (e.g., visual and/or audio) of the location and/or the guidance direction to the physician. Controller 1360 connects the catheter to the energy source, to an input system and to a visual display system. The controller may also connect to a motor 1326 that can directly move or assist movement of the catheter. In one embodiment, the physician may physically manipulate the shaft 1320 to move spade 1310 in the indicated direction. In other embodiments, the physician may direct movement of shaft 1320 via a user interface 1365 in communication with the controller (and motor 1326), allowing the physician to control movement of the spade 1310. Examples of user interfaces that can be included in embodiments include a handle, joystick, mouse, or trackball on a computer. In an alternative embodiment, the operator which can be the treating physician, can use a virtual, augmented, or mixed reality headset or virtual, augmented, or mixed reality goggles to guide movement of the sensing or treatment tool.

Figure 14A:
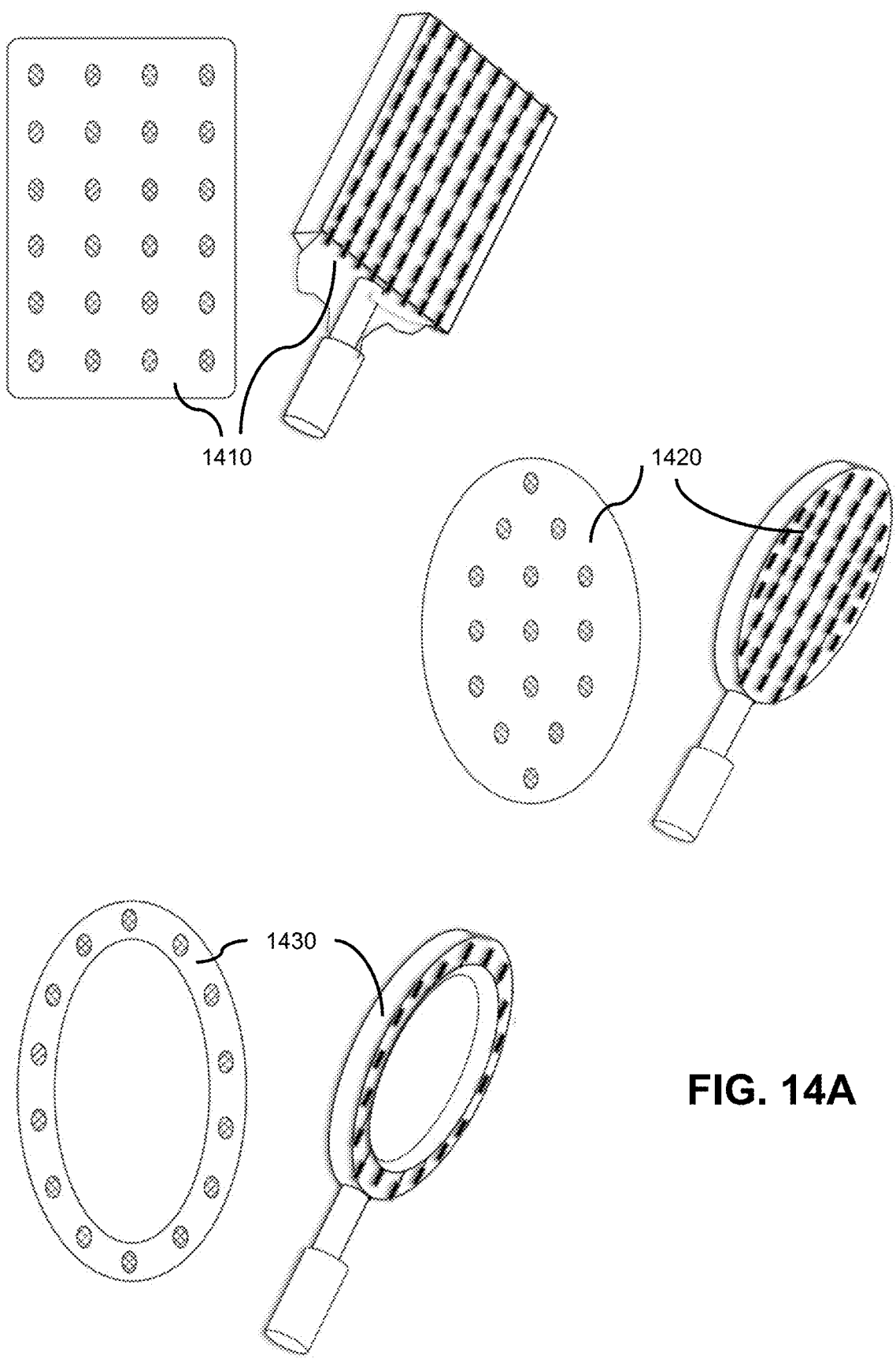
FIG. 14A illustrates examples of alternative spade configurations.

FIG. 14A illustrates three examples of alternative spade configurations. Spade 1410 is rectangular in shape with rounded corners, allowing for implementation of a rectangular grid of sensing electrodes. This configuration may provide stability in large planar structures such as the posterior wall of the left atrium. Spade 1420 is elliptical in shape, which may facilitate positioning of the device near extreme curvatures such as near the pulmonary veins but includes fewer electrodes near its periphery. Spade 1430 is annular with sensing electrodes arranged in a ring. This configuration may be most effective to "isolate" a region of interest without necessarily ablating it entirely, e.g., to minimize energy delivery and avoid damage to sensitive structures at the center of the region. These illustrated spade configurations are provided as examples only. As will be apparent to those of skill in the art, other shapes and aspect ratios may be used to tailor the catheter to the specific needs of the individual.

Figure 14B:
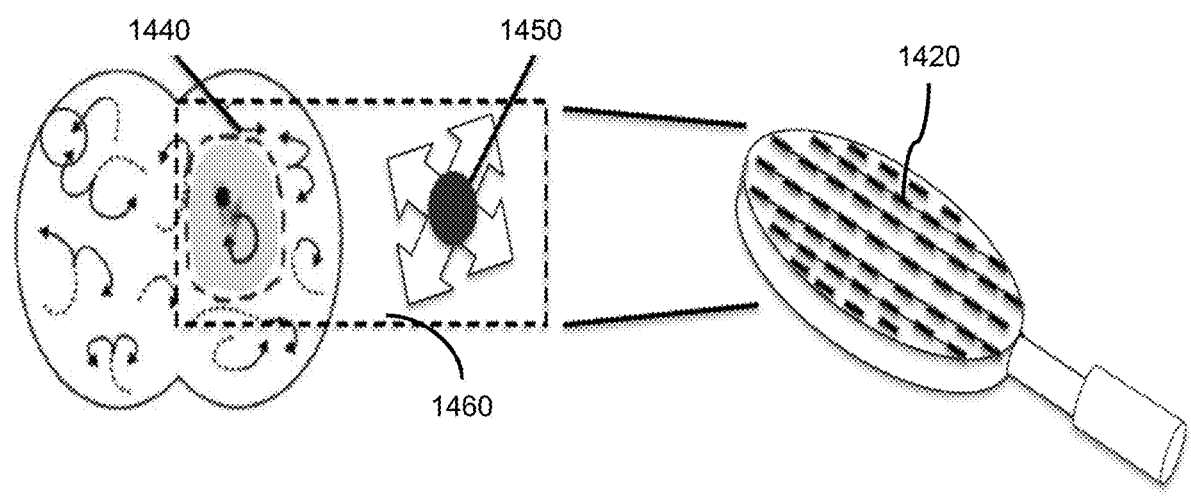
FIG. 14B illustrates tailoring of the spade configuration to source or other target regions in electrical rhythm disorders.

FIG. 14B provides one example of tailoring the spade configuration to source or other target regions in electrical rhythm disorders. The example illustrated is for atrial fibrillation, which may be sustained by regions of interest of sizes that are not points, but rather cover a "large domain" 1440. Alternatively, area 1450 represents regions of interest that may be focal regions with centrifugal propagation of activation, but may also be rotational, partial rotations, repetitive sites and other patterns of the types illustrated in FIG. 9. Area 1460 (within the dashed lines) depicts the approximate "domain size", or region of tissue which must be targeted to treat the biological rhythm disorder. As illustrated, this is the domain size of the desired target region which may exhibit low voltage, be an anatomical region of interest, or a localized source (focal, rotational, rotor, partial reentry, repetitive site in FIG. 9) for atrial fibrillation. Treatment of the biological rhythm is enabled by matching spades of various shapes and configurations to target the indicated domain size, e.g., 1440, 1450, or 1460.

Figure 15A:
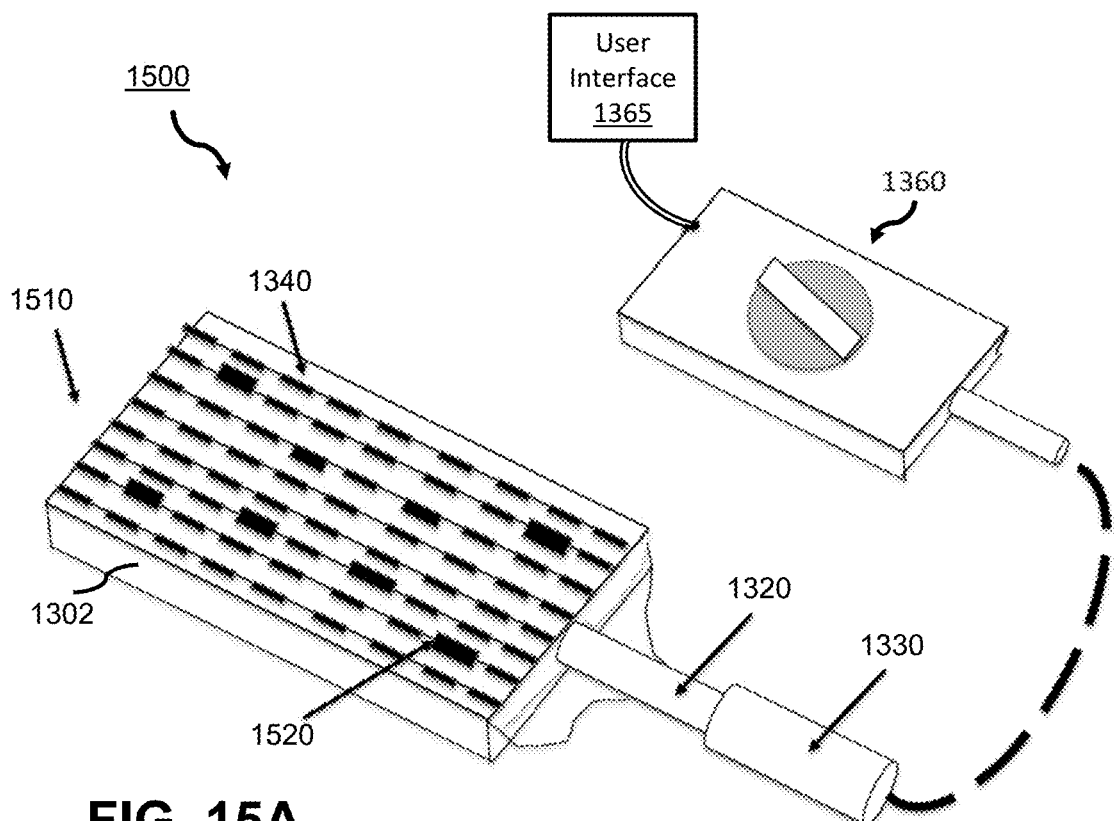
FIGS. 15A and 15B are perspective and cross-sectional views, respectively, of an embodiment of an ablation catheter configured to deliver electromagnetic energy to tissue.
Figure 15B:
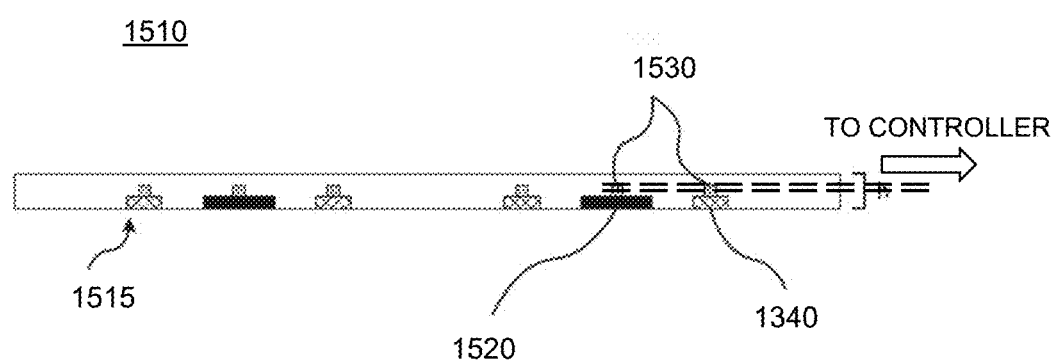

FIGS. 15A and 15B illustrate an embodiment of the inventive ablation catheter configured to apply electromagnetic energy to modify tissue at a target region. Ablation catheter 1500 includes a plurality of ablation electrodes 1520 that have a larger area than the small high-resolution sensing electrodes 1340 to allow delivery of electromagnetic energy for electroporation. The spacing between ablation electrodes 1520 can be small enough to ensure substantially contiguous tissue lesions. The ablation electrodes 1520 may be interspersed among the sensing electrodes 1340 as shown, or other patterns may be used. Ablation electrodes 1520 can be activated en masse, or they can be activated in one or more subregions, e.g., by dividing the electrodes into quadrants. The ablation electrodes 1520 may further be configured to deliver energy in a variety of energy signal shapes (waveforms).

As is known in the art, a waveform describes the electrical energy signal generated by the ablation electrodes and with a combination of variable parameters such as voltage, current, frequency, wave shape, duration, phase or other wave properties. For example, one waveform may be a sine wave having a specified amplitude and frequency that is applied for a specified duration, e.g., a few milliseconds. One example of ablating with varying waveforms may involve the controller causing a first ablation electrode to emit a sine wave having a first specified amplitude, shape, frequency, and duration, and causing a second ablation electrode to emit a sawtooth wave having a second specified amplitude, shape, frequency, and duration. Various combinations and sequences of waveforms may be employed.

The widthwise cross-sectional view of spade 1510 shown in FIG. 15B illustrates a single layer of the spade body 1302 with sensing electrodes 1340 and ablation electrodes 1520 positioned with their outer surfaces flush with contact surface 1515. Each electrode (sensing electrode 1340 and ablation electrode 1520) is connected via a corresponding wire 1530 that extends out of the spade body and continues through shaft 1320 to controller 1360.

Figure 16A:
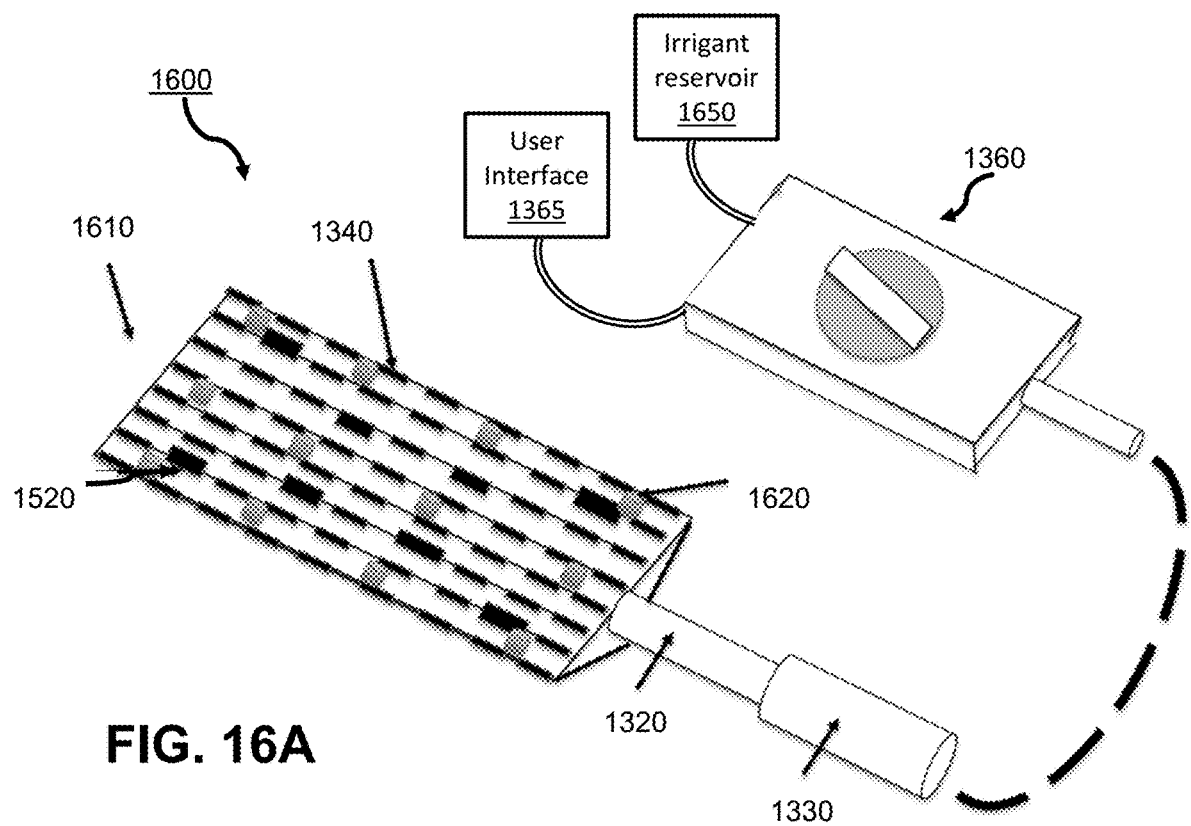
FIGS. 16A and 16B are perspective and cross-sectional views, respectively, of an embodiment of an ablation catheter configured to provide irrigant to the tissue.
Figure 16B:
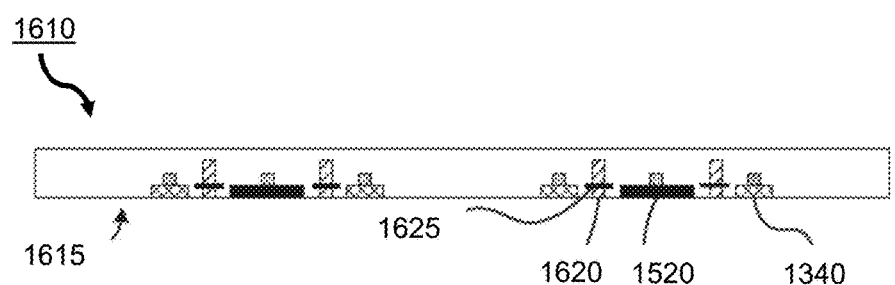

FIGS. 16A and 16B illustrate an embodiment of an ablation catheter configured to provide an irrigant, e.g., normal saline or a chemical buffer, to the tissue via one or more irrigation pores 1620. The irrigant cools the tissue surface to avoid overheating and possible power shut-down of the ablation electrode tip, allowing deeper energy delivery. Irrigation pores 1620 are shown evenly dispersed throughout a spade 1610, however, different arrangements may also be used. For example, irrigation pores 1620 may be concentrated in the proximity of ablation electrodes 1520. One or more irrigant channels extend through shaft 1320 (as part of bundle 1322) to connect the irrigation pores to an irrigant reservoir 1650 associated with and/or controlled by controller 1360, which controls the feeding of irrigant to the pores.

The widthwise (transverse) cross-sectional view of spade 1610 in FIG. 16B shows a single flexible layer with sensing electrodes 1340, ablation electrodes 1520, and irrigation pores 1620 arranged on contact surface 1615. In some implementations, each irrigation pore may further be controlled by a pore gate 1625 to mechanically gate flow from the irrigant channels to irrigation pore 1620. The pore gate(s) 1625 may further be controlled by controller 1360. In some embodiments, multiple irrigation pores 1620 may be controlled by a single pore gate 1625. The pore gate 1625 may further be controlled to release irrigant at different flow rates, e.g., periodically releasing 5 mL of irrigant every few minutes.

Figure 17A:
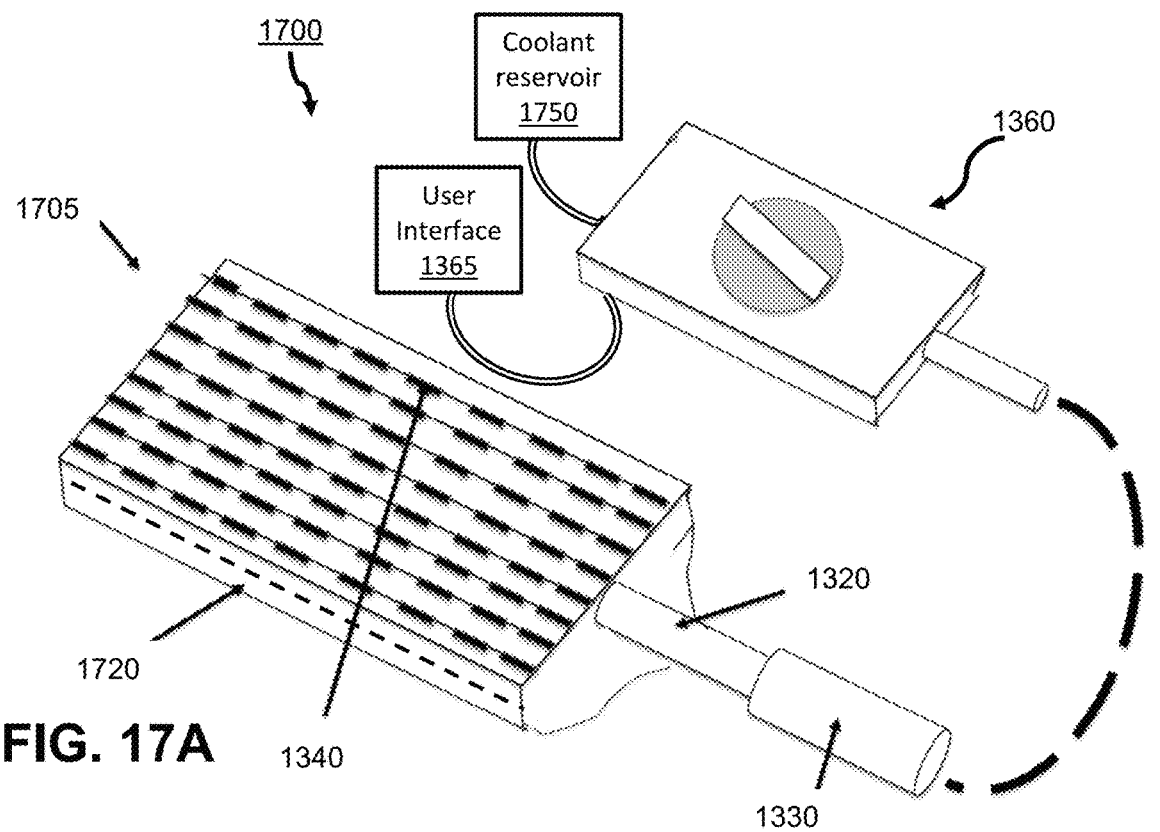
FIGS. 17A-17C are perspective and alternative cross-sectional views, respectively, of an embodiment of an ablation catheter with one or more cryoablation components configured to apply freezing energy.
Figure 17B:
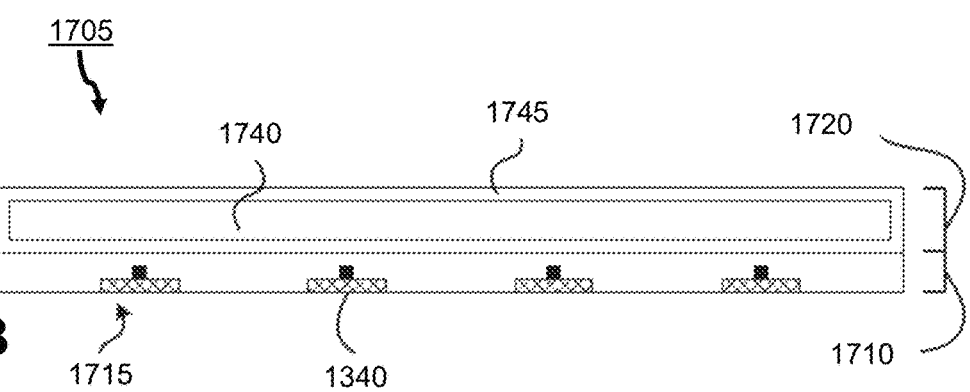
Figure 17C:
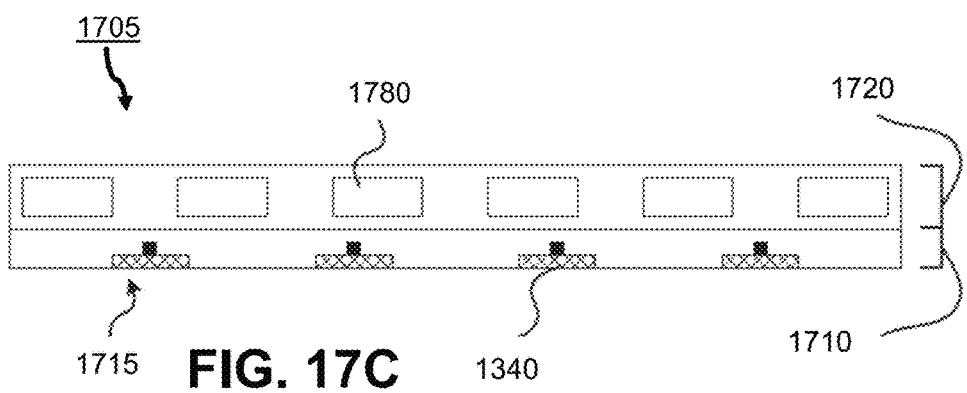

FIGS. 17A-17C illustrate variations of an embodiment of the inventive ablation catheter configured for delivering freezing energy to modify tissue at a source or other target region. The ablation catheter 1700 includes a sealed coolant layer 1720 incorporated into the body of spade 1705. The coolant layer 1720 may be a single coolant chamber 1740 (FIG. 17B), one or more coolant splines 1780 (FIG. 17C), other configurations of coolant chambers, etc. The coolant layer 1720 is configured to hold a coolant that rapidly cools some or all of the spade 1705. The cooled spade 1705 is useful for providing freezing energy to the tissue surface. The coolant chamber 1720 is coupled to controller 1360 via one or more coolant channels extending through shaft 1320.

The transverse cross-sectional view of spade 1705 shown in FIG. 17B illustrates the two layer structure of this embodiment, in which a first layer 1710 retains sensing electrodes 1340 arranged within contact surface 1715. The second layer 1720 is defined by a coolant chamber 1740 enclosed within chamber wall 1745. The material of which chamber wall 1745 is formed should have sufficient durability retain its seal after multiple exposures to the coolant as well as sufficiently thin and flexible to inflate with coolant. When chamber 1740 is deflated, the combined first and second layers must be sufficiently flexible to allow spade 1705 to collapse/fold into sheath 1330. The coolant chamber 1740 is connected to the coolant channels that extend through shaft 1320. One or more coolant channels extend through shaft 1320 (as part of bundle 1322) to connect the coolant chambers 1740 to a coolant reservoir 1750 associated with and/or controlled by controller 1360, which controls the feeding of coolant to the chambers (via a pump, not shown). A thermally conductive material may be embedded within or otherwise incorporated into first layer 1710 to enhance thermal transfer of freezing energy from the coolant chamber 1740 to contact surface 1715.

FIG. 17C illustrates an alternative transverse cross-sectional view of a spade 1705 in which second layer 1720 includes one or more coolant splines 1780 rather than the single coolant chamber 1740 of FIG. 17B. Sensing electrodes 1340 are arranged within contact surface 1715 of first layer 1710. Coolant splines 1780 are configured to fill with coolant to rapidly cool portions of contact surface 1715 corresponding to the spline. In some embodiments, coolant splines 1780 may be of a similar size and shape. As illustrated in FIG. 17C, coolant splines 1780 extend longitudinally within spade 1705, however, different configurations, e.g., sizes and shapes, may be used. Controller 1360 may separately deliver freezing energy to selected splines to target regions of the tissue to be treated. For example, the middle two coolant splines may be filled with coolant to cooling only the middle third portion of the spade. As described above, first layer 1710 may incorporate a thermally conductive material.

Figure 18A:
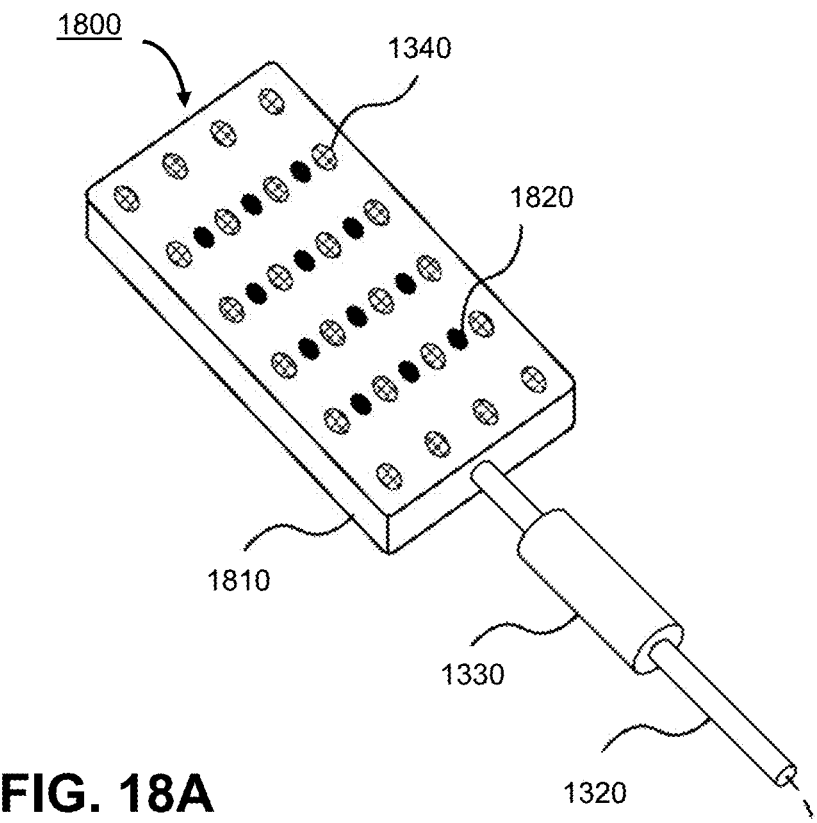
FIGS. 18A-18B are perspective and cross-sectional views, respectively, of an embodiment of an ablation catheter with one or more cryoablation components configured to apply freezing energy.
Figure 18A:
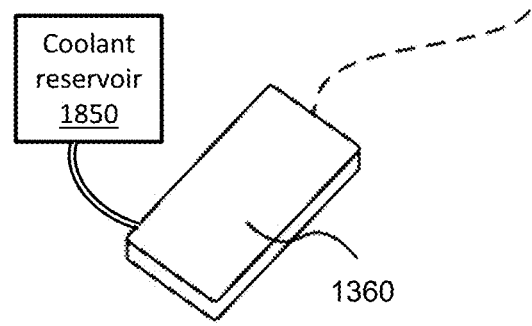
Figure 18B:
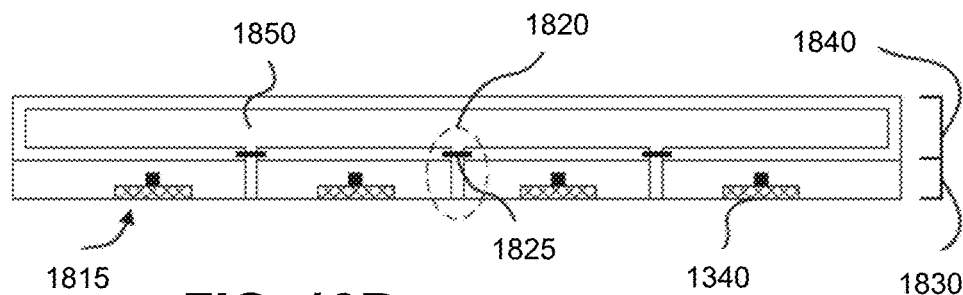

FIGS. 18A and 18B illustrate another embodiment of the inventive ablation catheter for effecting cryoablation. Ablation catheter 1800 comprises a spade 1810 with sensing electrodes 1340 and one or more cryoablation loci 1820 located on contact surface 1815 to deliver freezing energy to a tissue surface.

The widthwise cross-sectional view shown in FIG. 18B illustrates the two layer configuration of spade 1810. First layer 1830 that supports sensing electrodes 1340 and cryoablation loci 1820 within contact surface 1815. Second layer 1840 encloses coolant chamber 1850, which is similar in construction to coolant chamber 1740 of spade 1705. The cryoablation loci 1820 are channels that extend partially through first layer 1830 and connect to coolant chamber 1850. These channels are sealed at contact surface 1815 such that coolant is not released from the device. The cryoablation loci 1820 are configured to be filled with coolant from the coolant chamber 1850. When filled with coolant, the area on contact surface 1815 corresponding to the cryoablation loci 1820 are rapidly cooled to provide the freezing energy to the adjacent tissue. In some embodiments, a cryoablation loci 1820 has a locus gate 1825 to selectively allow coolant to flow from coolant chamber 1850 to the cryoablation locus 1820. The locus gate 1825 may be controlled by controller 1360. In other embodiments, the cryoablation loci 1820 may be connected directly to a coolant channel without a coolant chamber 1850. The tradeoff being that having the coolant chamber 1850 increases a maximum amount of freezing energy, i.e., affecting a speed of cooling, but sacrificing on thickness of the spade 1810. One or more coolant channels extend through shaft 1320 (as part of bundle 1322) to connect the coolant loci 1820 to a coolant reservoir 1850 associated with and/or controlled by controller 1360, which controls the feeding of coolant to the loci (via a pump, not shown).

Figure 19:
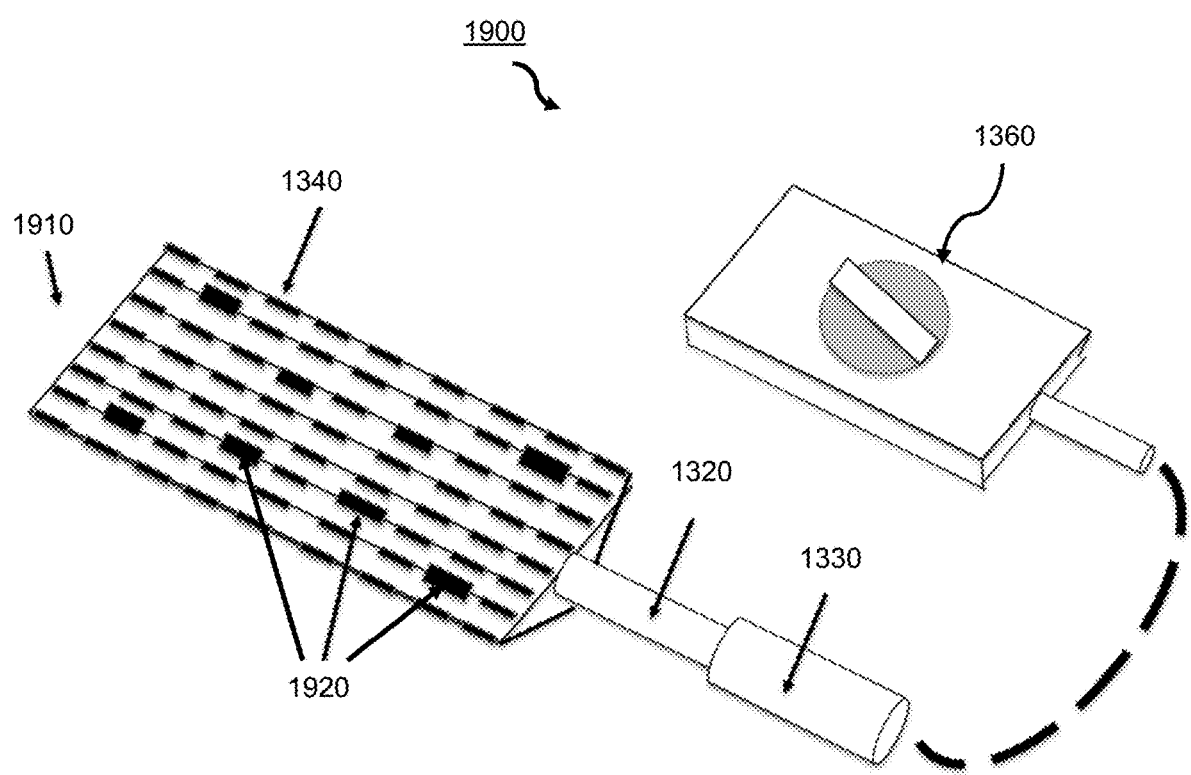
FIG. 19 is a perspective view of an embodiment of an ablation catheter with targeting fiducials.

FIG. 19 illustrates yet another embodiment of the inventive ablation catheter in which targeting fiducials are included to facilitate treatment via external energy sources. Ablation catheter 1900 includes a plurality of targeting fiducials 1920 positioned within spade 1910 for guiding delivery of ablation energy from one or more external ablation components. The targeting fiducials 1920 can be visualized using X-ray fluoroscopy or detected by other techniques as are known in the art. Once a treatment target for a heart rhythm is detected in this embodiment, energy can be delivered from an external source of X-rays or other electromagnetic radiation, or proton beams. Such energy sources may be similar to those used for radiotherapy for tumors. The spacing between targeting fiducials 1920 is small enough to ensure contiguous tissue lesions. Fiducials can be targeted en masse, or they can be targeted in subregions corresponding to sensor quadrants.

Figure 20:
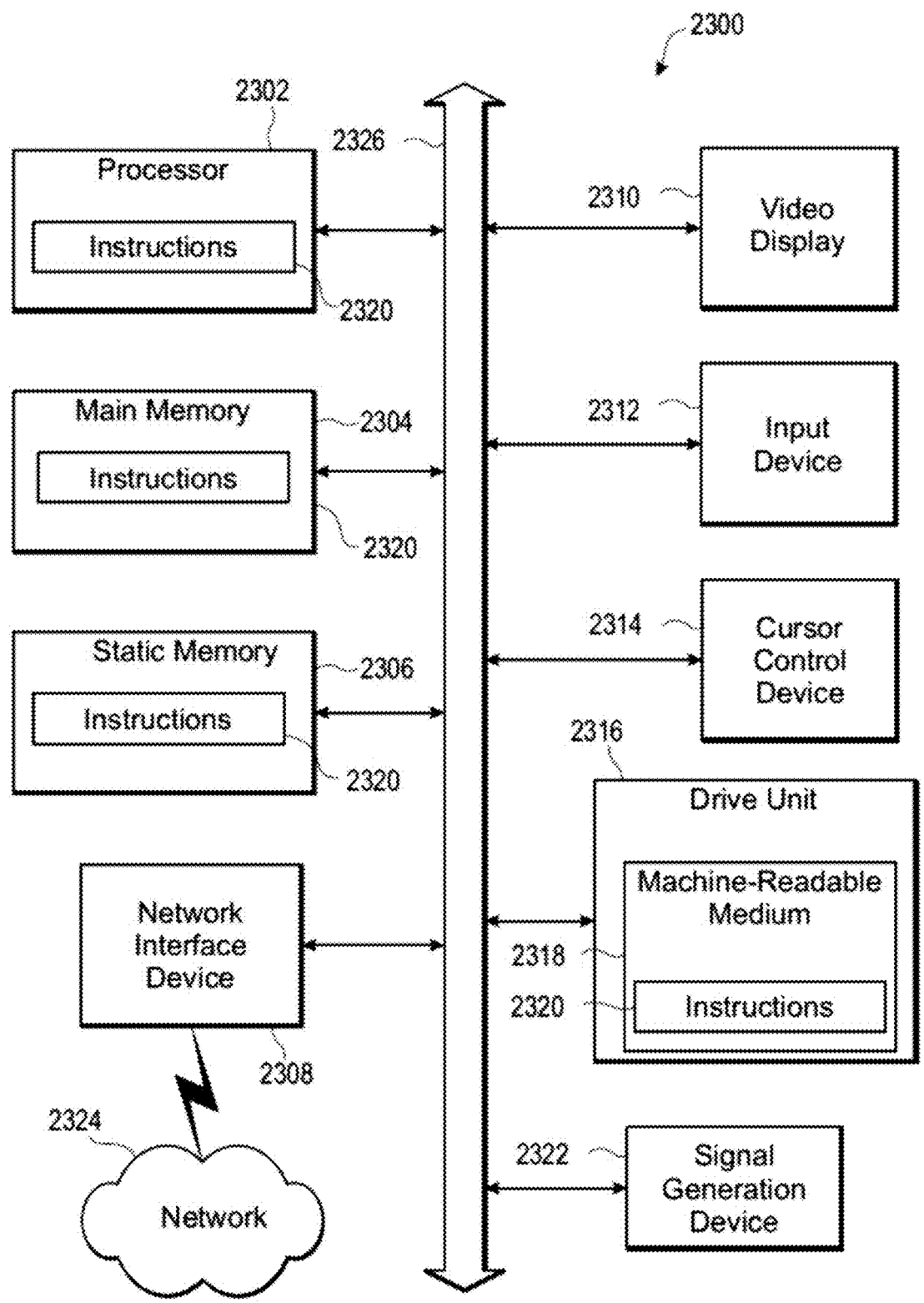
FIG. 20 is a block diagram of an exemplary computing environment for implementing embodiments of the invention.

FIG. 20 diagrammatically illustrates a computer system that can be used to implement the inventive method, as may be incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computer system 2300 is illustrated, the term "system" should also be taken to include any collection of systems or sub-systems that can individually or jointly execute a set, or multiple sets, of instructions to perform one or more computing functions.

As illustrated in FIG. 20, the computer system 2300 may include a computer processor 2302, e.g., a central processing unit (CPU), a graphics-processing unit (GPU), or both. The computer system may include a main memory 2304 and a static memory 2306 that can communicate with each other via a bus 2326. As shown, the computer system 2300 may further include a video display unit 2310, such as a liquid crystal display (LCD), an organic light emitting diode (OLED), a flat panel display, a solid state display, or a cathode ray tube (CRT). Additionally, the computer system 2300 may include an input device 2312, such as a keyboard, and a cursor control device 2314, such as a mouse. The computer system 2300 can also include a drive unit 2316, a signal generation device 2322, such as a speaker or remote control, and a network interface device 2308.

In some embodiments, the drive unit 2316 may include a computer-readable medium 2318 in which one or more sets of instructions 2320, e.g., software, are stored. The drive unit 2316 may be a disk drive, a thumb drive (USB flash drive), or other storage device. Further, the instructions 2320 may embody one or more of the methods or logic as described herein. In a particular embodiment, the instructions 2320 may reside completely, or at least partially, within the main memory 2304, the static memory 2306, and/or within the processor 2302 during execution by the computer system 2300. The main memory 2304 and the processor 2302 also may include computer-readable media.

In an alternative embodiment, dedicated hardware implementations, such as application specific integrated circuits (ASICs), programmable logic arrays (PLAs) and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments, the methods described herein may be implemented by software programs tangibly embodied in a processor-readable medium and may be executed by a processor. Further, in an exemplary, non-limited embodiment, implementations can include distributed processing, component/object distributed processing, and parallel processing. Alternatively, virtual computer system processing can be constructed to implement one or more of the methods or functionality as described herein.

It is also contemplated that a computer-readable medium includes instructions 2320 or receives and executes instructions 2320 responsive to a propagated signal, so that a device connected to a network 2324 can communicate voice, video or data over the network 2324. Further, the instructions 2320 may be transmitted or received over the network 2324 via the network interface device 2308.

The foregoing describes embodiments of a system and method to create personalized digital phenotypes of disease, which are compared to digital taxonomies to personalize therapy. Although specific example embodiments have been described, it will be evident that various modifications and changes may be made to these embodiments without departing from the broader scope of the invention. Accordingly, the detailed description is not to be taken in a limiting sense, and the scope of various embodiments is defined only by the appended claims, along with the full range of equivalents to which such claims are entitled.

The invention claimed is:

1. A system for treating a heart rhythm disorder, the system comprising:
   a catheter having a proximal end and a distal end, the catheter comprising:
      a flexible body disposed at the distal end of the catheter, the flexible body having a contact surface configured to substantially conform to a tissue surface within a target region;
      an array of sensor electrodes arranged within the flexible body, each sensor electrode having a conductive surface substantially flush with the contact surface, each sensor electrode configured to detect electrical signals from corresponding regions of the tissue surface in contact with the contact surface; and
      one or more treatment elements disposed within the flexible body configured to deliver energy to the tissue surface;
   an elongated hollow shaft having a length configured to retain a plurality of conductors, each conductor having a distal end connected to one of a sensor electrode and the one or more treatment elements within the flexible body; and
   a controller disposed at a proximal end of the catheter, the controller in communication with the plurality of conductors and a processor configured to:
      receive the detected electrical signals;
      determine from the detected electrical signals a location of a treatment target within the target region associated with the heart rhythm disorder;
      determine from the detected signals whether the one or more treatment elements overlies the treatment target, and, if not overlying the treatment target, to compute directionality to the treatment target and generate instructions to navigate the catheter toward the treatment target; and
      after determining that the one or more treatment elements is at least partially overlying the treatment target, generate treatment signals to activate the one or more treatment elements to modify tissue in the target region.

2. The system of claim 1, wherein the flexible body is planar and has a shape selected from a group consisting of a rectangle, an ellipse, and an annulus.

3. The system of claim 1, further comprising irrigant pores formed in the flexible body, the irrigant pores in fluid communication with an irrigant source associated with the controller, wherein the irrigant source is configured to deliver irrigant through the irrigant pores to tissue at the target region in conjunction with activation of the array of treatment elements.

4. The system of claim 1, wherein the array of sensor electrodes comprises at least four electrodes.

5. The system of claim 1, wherein the sensor electrodes are configured to deliver ablation energy so that the one or more treatment elements comprise the array of sensor electrodes.

6. The system of claim 1, wherein the one or more treatment elements comprises an array of cryoablation loci formed within the flexible body, and wherein the plurality of conductors comprises a subset of conductors configured to direct a coolant fluid from a coolant source to the cryoablation loci in response to treatment signals from the controller to deliver freezing energy to tissue at the target.

7. The system of claim 1, wherein the one or more treatment elements comprise an array of targeting fiducials distributed within the flexible body, the targeting fiducials configured for guiding delivery of ablation energy from one or more external ablation energy sources.

8. The system of claim 1, further comprising a contact sensor configured to determine whether the contact surface and the tissue surface are in adequate contact and, if not, to provide a signal to the controller to guide movement of the flexible body to provide improved contact.

9. The system of claim 1, wherein the processor is further configured to:
   determine a sequence of activation times from the detected electrical signals;
   determine activation fronts from the sequence of activation times; and
   using spatial gradients in a flow of activation fronts in time, infer a direction of one or more activation path toward a source of the heart rhythm disorder.

10. The system of claim 1, wherein the processor is further configured to:
   generate an array of electrograms in a pattern corresponding to positions of the sensor electrodes in the array of sensor electrodes; and
   determine an integrated direction of electrical flow over the array of sensor electrodes.

11. The system of claim 1, wherein the flexible body has a planar shape formed of an electrically-resistive polymer material, and wherein the array of sensor electrodes is arranged in a two-dimensional grid.

12. The system of claim 11, wherein the flexible body forms a planar volume, wherein the conductive elements of the array of sensor electrodes are disposed on the contact surface of the flexible body, and wherein the plurality of conductors is carried inside the planar volume of the flexible body.

13. The system of claim 1, further comprising an elongated hollow shaft having a distal end, a proximal end, and a length, wherein the catheter is disposed at the distal end, the controller is disposed at the proximal end, and the plurality of conductors is retained within and extends the length the shaft, wherein the distal end of the shaft is manipulable from the proximal end.

14. The system of claim 13, further comprising a shaft motor configured to steer the distal end of the shaft in response to movement instructions generated by the controller.

15. The system of claim 13, further comprising a sheath slidably disposed on the shaft, the sheath having an interior volume configured to retain the catheter in a folded condition until the catheter is deployed by sliding the sheath away from the distal end of the shaft.

16. The system of claim 1, wherein the one or more treatment elements comprise an array of ablation electrodes, and wherein a subset of the plurality of conductors connected to the one or more treatment elements are electrical conductors configured to deliver electromagnetic energy to each ablation electrode.

17. The system of claim 16, wherein the array of sensor electrodes and the array of ablation electrodes are uniformly distributed around the contact surface.

18. The system of claim 16, wherein ablation electrodes of the array of ablation electrodes are evenly interspersed among the array of sensor electrodes.

19. The system of claim 16, wherein the processor is further configured to:
   determine a size of the treatment target based on the detected electrical signals;
   identify one or more ablation electrodes of the array of ablation electrodes based on at least the size and the location of the treatment target; and
   activate the identified one or more ablation electrodes.

20. The system of claim 16, wherein each ablation electrode is configured to emit a distinct waveform.

21. The system of claim 1, wherein the processor computes directionality to the treatment target by:
   generating a directionality map of heart rhythms based on the detected electrical signals, the directionality map describing pathways of heart rhythms;
   generating a guidance direction in which to navigate the flexible body towards the treatment target, and
   integrating the directionality map to determine the location of the treatment target.

22. The system of claim 21, wherein the directionality map is generated by applying a trained machine learning model to the electrical signals, wherein the machine learning model is trained on training examples comprising electrical signals of a human heart and known target regions of the heart rhythm disorder.

23. The system of claim 20, wherein the controller is configured to separately address one or more subsets of ablation electrodes of the array, and wherein the treatment signals comprise a first signal to a first subset of ablation electrodes to emit a first waveform and a second signal to a second subset of ablation electrodes to emit a second waveform.

24. The system of claim 1, wherein the one or more treatment elements comprise one or more coolant chambers formed within the flexible body and configured for retaining a coolant, and wherein the plurality of conductors comprises a subset of conductors configured to direct a coolant fluid from a coolant source to the one or more coolant chambers to deliver freezing energy to tissue at the target.

25. The system of claim 24, wherein the flexible body has a thermally conductive material incorporated therein to enhance conduction of freezing energy to tissue in contact with the contact surface.

* * * * *